(12) United States Patent
Garcia et al.

(10) Patent No.: US 10,207,296 B2
(45) Date of Patent: Feb. 19, 2019

(54) MATERIAL SORTING SYSTEM

(71) Applicant: UHV Technologies, Inc., Fort Worth, TX (US)

(72) Inventors: Manuel Gerardo Garcia, Lexington, KY (US); Nalin Kumar, Fort Worth, TX (US); Subodh Das, Clayton, MO (US)

(73) Assignee: UHV Technologies, Inc., Fort Worth, TX (US)

( * ) Notice: Subject to any disclaimer, the term of this patent is extended or adjusted under 35 U.S.C. 154(b) by 0 days.

(21) Appl. No.: 15/213,129

(22) Filed: Jul. 18, 2016

(65) Prior Publication Data
US 2017/0014868 A1 Jan. 19, 2017

Related U.S. Application Data

(60) Provisional application No. 62/193,332, filed on Jul. 16, 2015.

(51) Int. Cl.
*B07C 5/34* (2006.01)
*B07C 5/10* (2006.01)
(Continued)

(52) U.S. Cl.
CPC .............. *B07C 5/3416* (2013.01); *B07C 5/10* (2013.01); *B07C 5/34* (2013.01); *B07C 5/346* (2013.01);
(Continued)

(58) Field of Classification Search
CPC .... B07C 5/04; B07C 5/10; B07C 5/34; B07C 5/346; B07C 5/3416; B07C 2501/0036;
(Continued)

(56) References Cited

U.S. PATENT DOCUMENTS

| | | |
|---|---|---|
| 2,194,381 A | 9/1937 | Cadman |
| 2,417,878 A | 2/1944 | Luzietti et al. |

(Continued)

FOREIGN PATENT DOCUMENTS

| | | |
|---|---|---|
| CA | 2893877 | 12/2015 |
| CN | 200953004 | 9/2007 |

(Continued)

OTHER PUBLICATIONS

B. Shaw, "Applicability of total reflection X-ray fluoresence (TXRF) as a screening platform for pharmaceutical inorganic impurity analysis," Journal of Pharmaceutical and Biomedical Analysis, vol. 63, 2012, pp. 151-159.

(Continued)

*Primary Examiner* — Joseph C Rodriguez
*Assistant Examiner* — Kalyanavenkateshware Kumar
(74) *Attorney, Agent, or Firm* — Matheson Keys & Kordzik PLLC; Kelly Kordzik

(57) ABSTRACT

A material sorting system sorts materials, such as scrap pieces composed of unknown metal alloys, as a function of their detected x-ray fluorescence. The x-ray fluorescence may be converted into an elemental composition signature that is then compared to an elemental composition signature of a reference material in order to identify and/or classify each of the materials, which are then sorted into separate groups based on such an identification/classification. The material sorting system may include an in-line x-ray tube having a plurality of separate x-ray sources, each of which can irradiate a separate stream of materials to be sorted.

24 Claims, 36 Drawing Sheets

(51) Int. Cl.
  *G01B 11/04* (2006.01)
  *G01N 23/223* (2006.01)
  *B07C 5/346* (2006.01)

(52) U.S. Cl.
  CPC ......... *G01B 11/043* (2013.01); *G01N 23/223* (2013.01); *G01N 2223/076* (2013.01); *G01N 2223/615* (2013.01); *G01N 2223/643* (2013.01)

(58) Field of Classification Search
  CPC ............... G01B 11/043; G01N 23/223; G01N 2223/076; G01N 2223/615
  USPC .............................. 209/576, 577, 586, 589
  See application file for complete search history.

(56) References Cited

U.S. PATENT DOCUMENTS

| | | |
|---|---|---|
| 2,942,792 A | 7/1957 | Anderson et al. |
| 2,953,554 A | 9/1960 | Miller et al. |
| 3,512,638 A | 5/1970 | Chengges et al. |
| 3,662,874 A | 5/1972 | Muller |
| 3,791,518 A | 2/1974 | Vanderhoof |
| 3,955,678 A | 5/1976 | Moyer |
| 3,973,736 A | 8/1976 | Nilsson |
| 3,974,909 A | 8/1976 | Johnson |
| 4,004,681 A | 1/1977 | Clewett et al. |
| 4,031,998 A | 6/1977 | Suzuki et al. |
| 4,044,897 A | 8/1977 | Maxted |
| 4,253,154 A * | 2/1981 | Russ ............... G01N 23/2251 250/311 |
| 4,317,521 A | 3/1982 | Clark et al. |
| 4,413,721 A | 11/1983 | Bonier |
| 4,488,610 A | 12/1984 | Yankloski |
| 4,572,735 A | 12/1986 | Poetzschke et al. |
| 4,726,464 A | 2/1988 | Canziani |
| 4,834,870 A | 5/1989 | Osterberg et al. |
| 4,848,590 A | 7/1989 | Kelly |
| 5,054,601 A | 10/1991 | Sjogren et al. |
| 5,114,230 A | 5/1992 | Pryor |
| 5,236,092 A | 8/1993 | Krotkov et al. |
| 5,260,576 A | 11/1993 | Sommer, Jr. et al. |
| 5,433,311 A | 7/1995 | Bonnet |
| 5,462,172 A | 10/1995 | Kumagai et al. |
| 5,570,773 A | 11/1996 | Bonnet |
| 5,663,997 A | 9/1997 | Willis et al. |
| 5,676,256 A | 10/1997 | Kumar et al. |
| 5,738,224 A | 4/1998 | Sommer, Jr. et al. |
| 5,836,436 A | 11/1998 | Fortenbery et al. |
| 5,911,327 A | 6/1999 | Tanaka et al. |
| 6,076,653 A | 6/2000 | Bonnet |
| 6,100,487 A | 8/2000 | Schultz et al. |
| 6,148,990 A | 11/2000 | Lapeyre et al. |
| 6,266,390 B1 | 7/2001 | Sommer, Jr. et al. |
| 6,273,268 B1 | 8/2001 | Axmann |
| 6,313,422 B1 | 11/2001 | Anibas |
| 6,412,642 B2 | 7/2002 | Charles et al. |
| 6,457,859 B1 | 10/2002 | Lu et al. |
| 6,519,315 B2 | 2/2003 | Sommer, Jr. et al. |
| 6,795,179 B2 | 9/2004 | Kumar |
| 6,888,917 B2 | 5/2005 | Sommer, Jr. et al. |
| 6,983,035 B2 | 1/2006 | Price et al. |
| 7,073,651 B2 | 7/2006 | Costanzo et al. |
| 7,099,433 B2 | 8/2006 | Sommer et al. |
| 7,200,200 B2 | 4/2007 | Laurila et al. |
| 7,341,154 B2 | 3/2008 | Boer |
| 7,564,943 B2 | 7/2009 | Sommer, Jr. et al. |
| 7,616,733 B2 | 11/2009 | Sommer et al. |
| 7,674,994 B1 | 3/2010 | Valerio |
| 7,763,820 B1 | 7/2010 | Sommer, Jr. et al. |
| 7,848,484 B2 | 12/2010 | Sommer, Jr. et al. |
| 7,886,915 B2 | 2/2011 | Shulman |
| 7,903,789 B2 | 3/2011 | Morton et al. |
| 7,978,814 B2 | 7/2011 | Sommer et al. |
| 7,991,109 B2 | 8/2011 | Golenhofen |
| 8,073,099 B2 | 12/2011 | Niu et al. |
| 8,144,831 B2 | 3/2012 | Sommer, Jr. et al. |
| 8,172,069 B2 | 5/2012 | Prakasam |
| 8,476,545 B2 | 7/2013 | Sommer et al. |
| 8,553,838 B2 | 10/2013 | Sommer et al. |
| 8,567,587 B2 | 10/2013 | Faist et al. |
| 8,576,988 B2 | 11/2013 | Lewalter et al. |
| 8,654,919 B2 | 2/2014 | Sabol et al. |
| 8,855,809 B2 | 10/2014 | Spencer et al. |
| 8,903,040 B2 | 12/2014 | Maeyama et al. |
| 2003/0038064 A1 | 2/2003 | Harbeck et al. |
| 2003/0147494 A1 | 8/2003 | Sommer, Jr. et al. |
| 2006/0239401 A1 | 10/2006 | Sommer, Jr. et al. |
| 2008/0029445 A1 | 2/2008 | Russcher et al. |
| 2010/0017020 A1 | 1/2010 | Hubbard-Nelson et al. |
| 2010/0195795 A1 | 8/2010 | Golenhofen |
| 2010/0264070 A1 | 10/2010 | Sommer, Jr. et al. |
| 2010/0282646 A1 | 11/2010 | Looy et al. |
| 2012/0148018 A1 | 6/2012 | Sommer, Jr. et al. |
| 2012/0288058 A1 | 11/2012 | Maeyama et al. |
| 2013/0079918 A1* | 3/2013 | Spencer ............... B07C 5/3416 700/223 |
| 2013/0092609 A1 | 4/2013 | Andersen |
| 2013/0264249 A1* | 10/2013 | Sommer, Jr. ............ B07C 5/346 209/589 |
| 2013/0304254 A1 | 11/2013 | Torek et al. |

FOREIGN PATENT DOCUMENTS

| | | |
|---|---|---|
| CN | 201440132 | 4/2010 |
| CN | 201464390 | 5/2010 |
| CN | 101776620 A | 7/2010 |
| CN | 201552461 | 7/2010 |
| CN | 103745901 | 4/2014 |
| CN | 10177620 B | 6/2014 |
| CN | 203688493 | 7/2014 |
| CN | 204359695 | 5/2015 |
| CN | 204495749 | 7/2015 |
| CN | 204537711 | 8/2015 |
| CN | 204575572 | 8/2015 |
| EP | 00111892 | 11/1983 |
| EP | 0074447 | 1/1987 |
| EP | 0433828 A2 | 12/1990 |
| EP | 0351778 B1 | 10/1993 |
| JP | 5083196 | 11/2012 |
| RU | 2004101401 | 2/2005 |
| RU | 2006136756 | 4/2008 |
| RU | 2339974 | 11/2008 |
| RU | 2361194 | 7/2009 |
| WO | 2001/022072 | 3/2001 |
| WO | 2011/159269 | 12/2011 |
| WO | 2012094568 A2 | 7/2012 |
| WO | 2013/03357 | 3/2013 |
| WO | WO 2013/180922 | 12/2013 |
| WO | 2015/195988 | 12/2015 |

OTHER PUBLICATIONS

Briefing Elemental Impurities—Limits, Revision Bulletin, The United States Pharmacopeial Convention, Feb. 1, 2013, 3 pages.
Chapter 6, Functional Description, S2 Picofox User Manual, 2008, pp. 45-64.
D. Bradley, "Pharmaceutical toxicity: AAS and other techniques measure pharma heavy metal," Ezine, May 15, 2011, 2 pages.
E. Margui et al., "Determination of metal residues in active pharmaceutical ingredients according to European current legislation by using X-ray fluorescence spectrometry," J. Anal. At. Spectrom., Jun. 16, 2009, vol. 24, pp, 1253-1257.
Elemental Impurity Analysis in Regulated Pharmaceutical Laboratories, A Primer, Agilent Technologies, Jul. 3, 2012. 43 pages.
Exova, X-ray fluorescence: a new dimension to elemental analysis, downloaded from www.exova.com on Jul. 26, 2016, 3 pages.
G. O'Neil, "Identification and Analysis of Heavy Metals in Solution. (Hg, Cu, Pb, Zn, Ni) by Use of in Situ Electrochemical X-ray Fluorescence," Analytical Chemistry, Feb. 2015, 22 pages.
Guideline for Elemental Impurities, Q3D, International Conference on Harmonisation of Technical Requirements for Registration of

(56) References Cited

OTHER PUBLICATIONS

Pharmaceuticals for Human Use, ICH Harmonised Guideline, Current Step 4 version, Dec. 16. 2014, 77 pages.
H. Rebiere et al., "Contribution of X-Ray Fluorescence Spectrometry for the Analysis of Falsified Products," ANSM, The French National Agency for Medicines and Health Products Safety, Laboratory Controlls Division, France, 1 page, (date unknown).
International Searching Authority, International Search Report and the Written Opinion, International Application No. PCT/US2016/42850, dated Sep. 28, 2016.
International Searching Authority, International Search Report and the Written Opinion of the International Searching Authority, International Application No. PCT/US2016/45349, dated Oct. 17, 2016.
J. McComb et al., "Rapid screening of heavy metals and trace elements in environmental samples using portable X-ray fluorescence spectrometer, A comparative study," Water Air Soil Pollut., Dec. 2014, vol. 225, No. 12, pp. 1-16.
J. Mondia, "Using X-ray fluoresence to measure inorganics in biopharmaceutical raw materials, " Anal. Methods, Mar. 18, 2015, vol. 7, pp. 3545-3550.
L. Goncalves, "Assesment of metal elements in final drug products by wavelength dispersive X-ray fluorescence spectrometry," Anal. Methods, May 19, 2011, vol. 3, pp. 1468-1470.
L. Hutton, "Electrochemical X-ray Fluorescence Spectroscopy for Trace Heavy Metal Analysis: Enhancing X-ray Fluorescence Detection Capabilities by Four Orders of Magnitude," Analytical Chemistry, Apr. 4, 2014, vol. 86, pp. 4566-4572.
L. Moens et al., Chapter 4, X-Ray Fluorescence, Modern Analytical Methods in Art and Archaeology, Chemical Analysis Series, vol. 155, pp. 55-79, copyright 2000.
M. Baudelet et al., "The first years of laser-induced breakdown spectroscopy," J. Anal. At. Spectrom., Mar. 27, 2013, 6 pages.
R. Sitko et al., "Quantification in X-ray Fluorescence Spectrometry," X-Ray Spectroscopy, Dr. Shatendra K Sharma (Ed.), ISMN: 978-953-307-967-7, InTech, 2012, pp. 137-163; Available from: http://www.intechopen.com/books/x-ray-spectroscopy/quantification-in-x-ray-fluorescence-spectrometry.
T. Miller et al., "Elemental Imaging for Pharmaceutical Tablet Formulations Analysis By Micro X-ray Fluorescence, " International Centre for Diffraction Data, 2005, Advances in X-ray Analysis, vol. 48, pp. 274-283.
T. Moriyama, "Pharmaceutical Analysis (5), Analysis of trace impurities in pharmaceutical products using polarized EDXRF spectrometer NEX CG," Rigaku Journal, vol. 29, No. 2, 2013, pp. 19-21.
U.S. Appl. No. 15/213,129, filed Jul. 18, 2016.
International Alloy Designations and Chemical Composition Limits for Wrought Aluminum and Wrought Aluminum Alloys, The Aluminum Association, Inc., revised Jan. 2015, 38 pages.
Scrap Specifications Circular, Institute of Scrap Recycling Industries, Inc., effective Jan. 21, 2016, 58 pages.
Schwoebel et al., "Studies of a prototype linear stationary x-ray source for tomosynthesis imaging," Phys. Med Biol. 59, pp. 2393-2413, Apr. 17, 2014.
The International Bureau of WIPO, International Preliminary Report on Patentability, International Application No. PCT/US2016/42850, dated Jan. 25, 2018.
European Patent Office; Supplemental Search Report for corresponding EP application No. 168253116; dated Sep. 26, 2018; 15 pages; Munich, DE.

\* cited by examiner

|  | Si | Fe | Cu | Mn | Mg | Cr | Ni | Zn | Ti | Ag | B | Others | | Al Remainder |
|---|---|---|---|---|---|---|---|---|---|---|---|---|---|---|
|  |  |  |  |  |  |  |  |  |  |  |  | Each | Total |  |
| 6013 | 0.6-1.0 | 0.5 | 0.6-1.1 | 0.20-0.8 | 0.8-1.2 | 0.1 | ... | 0.25 | 0.1 | ... | ... | 0.05 | 0.15 | Remainder |
| 6022 | 0.8-1.5 | 0.05-0.2 | 0.01-0.11 | 0.02-0.10 | 0.45-0.7 | 0.1 | ... | 0.25 | 0.15 | 0.25 | 0.15 | 0.05 | 0.15 | Remainder |
| 6061 | 0.4-0.8 | 0.7 | 0.15-0.4 | 0.15 | 0.8-1.2 | 0.04-0.35 | ... | 0.25 | 0.15 | 0.25 | 0.15 | 0.05 | 0.15 | Remainder |

| 6013 | Net Counts |
|---|---|
| Mg | 90 |
| Al | 20960 |
| Si | 81 |
| Ti | 272 |
| Cr | 0 |
| Mn | 5006 |
| Fe | 5998 |
| Cu | 18561 |
| Zn | 28 |

| 6013 | Normalized Vector |
|---|---|
| | 0.003096171 |
| | 0.72106393 |
| | 0.002786554 |
| | 0.009357318 |
| | 0 |
| | 0.172215937 |
| | 0.206342627 |
| | 0.63853376 |
| | 0.000963253 |

4060-001001

| Sample | ECS |
|--------|------|
| Mg | 0.00 |
| Al | 0.41 |
| Si | 0.00 |
| Ti | 0.01 |
| Cr | 0.00 |
| Mn | 0.10 |
| Fe | 0.12 |
| Cu | 0.36 |
| Zn | 0.00 |

| 6013 | ECS Signature | | |
|------|------|------|------|
| | ECS | +/− | Error |
| Mg | 0.00 | +/− | 0.03 |
| Al | 0.40 | +/− | 0.05 |
| Si | 0.00 | +/− | 0.03 |
| Ti | 0.01 | +/− | 0.03 |
| Cr | 0.00 | +/− | 0.03 |
| Mn | 0.09 | +/− | 0.05 |
| Fe | 0.11 | +/− | 0.05 |
| Cu | 0.35 | +/− | 0.05 |
| Zn | 0.00 | | 0 |

| 6022 | ECS Signature | | |
|------|------|------|------|
| | ECS | +/− | Error |
| Mg | 0.00 | +/− | 0.03 |
| Al | 0.78 | +/− | 0.05 |
| Si | 0.00 | +/− | 0.03 |
| Ti | 0.00 | +/− | 0.03 |
| Cr | 0.00 | +/− | 0.03 |
| Mn | 0.04 | +/− | 0.05 |
| Fe | 0.11 | +/− | 0.05 |
| Cu | 0.05 | +/− | 0.05 |
| Zn | 0.01 | | 0 |

| 5086 Normalized Vector | 5086 Normalized Vector | Multiplied Components |
|---|---|---|
| 0.002319058 | 0.002319058 | 5.37803E-06 |
| 0.892558928 | 0.892558928 | 0.79666144 |
| 0.000649336 | 0.000649336 | 4.21637E-07 |
| 0 | 0 | 0 |
| 0.035296058 | 0.035296058 | 0.001245812 |
| 0.33116144 | 0.33116144 | 0.109667899 |
| 0.287841442 | 0.287841442 | 0.082852696 |
| 0.075369375 | 0.075369375 | 0.005680543 |
| 0.062336271 | 0.062336271 | 0.003885811 |

Dot Product  1

| 5086 Normalized Vector | 5052 Normalized Vector | Multiplied Components |
|---|---|---|
| 0.002319058 | 0 | 0 |
| 0.892558928 | 0.968282127 | 0.864248857 |
| 0.000649336 | 0 | 0 |
| 0 | 0.002808847 | 0 |
| 0.035296058 | 0.127122989 | 0.00448694 |
| 0.33116144 | 0.069133885 | 0.022894477 |
| 0.287841442 | 0.200968489 | 0.05784706 |
| 0.075369375 | 0 | 0 |
| 0.062336271 | 0.033071911 | 0.00206158 |

Dot Product  0.951538914

| 5086 Normalized Vector | 5182 Normalized Vector | Multiplied Components |
|---|---|---|
| 0.002319058 | 0 | 0 |
| 0.892558928 | 0.910268527 | 0.8124683 |
| 0.000649336 | 0.00142185 | 9.23259E-07 |
| 0 | 0 | 0 |
| 0.035296058 | 0 | 0 |
| 0.33116144 | 0.306171753 | 0.101392278 |
| 0.287841442 | 0.271241632 | 0.078074582 |
| 0.075369375 | 0.007109251 | 0.00053582 |
| 0.062336271 | 0.06304101 | 0.003964842 |
| Dot Product | | 0.996436747 |

| 5086 Normalized Vector | 5454 Normalized Vector | Multiplied Components |
|---|---|---|
| 0.002319058 | 0.011960463 | 2.76075E-6 |
| 0.892558928 | 0.806218084 | 0.719597149 |
| 0.000649336 | 0004899213 | 3.18124E-6 |
| 0 | 0.00293037 | 0 |
| 0.035296058 | 0.020466804 | 0.000722398 |
| 0.33116144 | 0.489097091 | 0.161970097 |
| 0.287841442 | 0.328064094 | 0.094430442 |
| 0.075369375 | 0.028937405 | 0.002180994 |
| 0.062336271 | 0.043360321 | 0.002702921 |
| Dot Product | | 0.981609942 |

| 5052 | Net Counts | ECS |
|---|---|---|
| Mg | 0 | 0.00 |
| Al | 21373 | 0.69 |
| Si | 0 | 0.00 |
| Ti | 62 | 0.00 |
| Cr | 2806 | 0.09 |
| Mn | 1526 | 0.05 |
| Fe | 4436 | 0.14 |
| Cu | 0 | 0.00 |
| Zn | 730 | 0.02 |

| 5086 | Net Counts | ECS |
|---|---|---|
| Mg | 50 | 0.00 |
| Al | 19244 | 0.53 |
| Si | 14 | 0.00 |
| Ti | 0 | 0.00 |
| Cr | 761 | 0.02 |
| Mn | 7140 | 0.20 |
| Fe | 6206 | 0.17 |
| Cu | 1625 | 0.04 |
| Zn | 1344 | 0.04 |

| 5182 | Net Counts | ECS |
|---|---|---|
| Mg | 0 | 0.00 |
| Al | 19206 | 0.58 |
| Si | 30 | 0.00 |
| Ti | 0 | 0.00 |
| Cr | 0 | 0.00 |
| Mn | 6460 | 0.20 |
| Fe | 5723 | 0.17 |
| Cu | 150 | 0.00 |
| Zn | 1342 | 0.04 |

| 5454 | Net Counts | ECS |
|---|---|---|
| Mg | 26 | 0.00 |
| Al | 17608 | 0.47 |
| Si | 107 | 0.00 |
| Ti | 64 | 0.00 |
| Cr | 447 | 0.01 |
| Mn | 10682 | 0.28 |
| Fe | 7165 | 0.19 |
| Cu | 632 | 0.02 |
| Zn | 947 | 0.03 |

| ECS 5052 | | | | ECS 5086 | | | | ECS 5182 | | | | ECS 5454 | | | |
|---|---|---|---|---|---|---|---|---|---|---|---|---|---|---|---|
| | Value | | Error | | Value | | Error | | Value | | Error | | Value | | Error |
| Mg | 0.00 | ±1 | 0.02 | Mg | 0.00 | ±1 | 0.02 | Mg | 0.00 | ±1 | 0.02 | Mg | 0.00 | ±1 | 0.02 |
| Al | 0.69 | ±1 | 0.02 | Al | 0.53 | ±1 | 0.02 | Al | 0.58 | ±1 | 0.02 | Al | 0.47 | ±1 | 0.02 |
| Si | 0.00 | ±1 | 0.02 | Si | 0.00 | ±1 | 0.02 | Si | 0.00 | ±1 | 0.02 | Si | 0.00 | ±1 | 0.02 |
| Ti | 0.00 | ±1 | 0.02 | Ti | 0.00 | ±1 | 0.02 | Ti | 0.00 | ±1 | 0.02 | Ti | 0.00 | ±1 | 0.02 |
| Cr | 0.09 | ±1 | 0.02 | Cr | 0.02 | ±1 | 0.02 | Cr | 0.00 | ±1 | 0.02 | Cr | 0.01 | ±1 | 0.02 |
| Mn | 0.05 | ±1 | 0.02 | Mn | 0.20 | ±1 | 0.02 | Mn | 0.20 | ±1 | 0.02 | Mn | 0.28 | ±1 | 0.02 |
| Fe | 0.14 | ±1 | 0.02 | Fe | 0.17 | ±1 | 0.02 | Fe | 0.17 | ±1 | 0.02 | Fe | 0.19 | ±1 | 0.02 |
| Cu | 0.00 | ±1 | 0.01 | Cu | 0.04 | ±1 | 0.01 | Cu | 0.00 | ±1 | 0.01 | Cu | 0.02 | ±1 | 0.01 |
| Zn | 0.02 | ±1 | 0.02 | Zn | 0.04 | ±1 | 0.02 | Zn | 0.04 | ±1 | 0.02 | Zn | 0.03 | ±1 | 0.02 |

FIG. 33

MATERIAL SORTING SYSTEM

This patent application claims priority to U.S. provisional patent application Ser. No. 62/193,332, which is incorporated by reference herein.

GOVERNMENT LICENSE RIGHTS

This invention was made with U.S. government support under Grant No. DE-AR0000422 awarded by the U.S. Department of Energy. The U.S. government may have certain rights in this invention.

TECHNOLOGY FIELD

The present disclosure relates in general to the sorting of materials, such as scrap metals, and in particular, to the sorting of pieces of materials (by composition) in a stream of materials moving along a conveyor system.

BACKGROUND INFORMATION

This section is intended to introduce various aspects of the art, which may be associated with exemplary embodiments of the present disclosure. This discussion is believed to assist in providing a framework to facilitate a better understanding of particular aspects of the present disclosure. Accordingly, it should be understood that this section should be read in this light, and not necessarily as admissions of prior art.

Typically, the sorting of pieces of materials has involved determining a physical property or properties of each piece, and grouping together pieces sharing a common property or properties. Such properties may include color, hue, texture, weight, density, transmissivity to light, sound, or other signals, in reaction to stimuli such as various fields.

Scrap metals are often shredded, and thus require sorting to facilitate reuse of the metals. By sorting the scrap metals, metal is reused that may otherwise go to a landfill. Additionally, use of sorted scrap metal leads to reduced pollution and emissions in comparison to refining virgin feedstock from ore. Scrap metals may be used in place of virgin feedstock by manufacturers if the quality of the sorted metal meets certain standards. The scrap metals may include types of ferrous and nonferrous metals, heavy metals, high value metals such as nickel or titanium, cast or wrought metals, and other various alloys.

The recycling of nonferrous metals from shredded end-of-life equipment, such as cars or domestic appliances, is steadily increasing in importance, as many raw materials, such as copper or aluminum, can be recovered in this manner. However, for this to be possible, these fractions must be extracted to a high degree of purity. Therefore, an effective, efficient, and economical sorting process can add value because the market value of refined individual non-ferrous fractions is significantly higher than that of unsorted ferrous mixtures.

The recycling of aluminum scrap is a very attractive proposition in that up to 95% of the energy costs can be saved when compared with the laborious extraction of the more costly primary aluminum. Primary aluminum is defined as aluminum originating from aluminum-enriched ore, such as bauxite. At the same time, the demand for aluminum is steadily increasing in markets, such as car manufacturing, because of its lightweight properties. Correspondingly, it is particularly desirable to efficiently separate aluminum scrap metals into alloy families, since mixed aluminum scrap of the same alloy family is worth much more than that of indiscriminately mixed alloys. For example, in the blending methods used to recycle aluminum, any quantity of scrap composed of similar, or the same, alloys and of consistent quality, has more value than scrap consisting of mixed aluminum alloys.

Wrought scrap contains a mixture of wrought alloys. The mixed wrought scrap has limited value because the mixture, due to its combined chemical composition, must be diluted if used to produce a new wrought alloy. The reason this is so is due to the more stringent compositional tolerances of wrought alloys, which are required to meet the performance requirements of wrought products. The high value scrap should have a high absorption back into the recycled product. High absorption means that a substantial portion of the final product is composed of scrap. To increase the value of the wrought scrap requires the separation of wrought product into alloy grades or similar constituted materials to maximize absorption. Mixed alloy scrap presents some difficult problems in separability due to its poor absorption into high quality wrought alloys. Mixed alloy scrap has poor absorption into high quality wrought alloys, and as a result, only limited amounts of mixed scrap can be used for recycling into wrought products. Absorption is defined as the percentage of an alloy or mixture that can be used to produce an ingot of another desired composition without exceeding the specified alloy composition limits. Within such aluminum alloys, aluminum will always be the bulk of the material. However, constituents such as copper, magnesium, silicon, iron, chromium, zinc, manganese, and other alloy elements provide a range of properties to alloyed aluminum and provide a means to distinguish one wrought alloy from the other.

The Aluminum Association is the authority which defines the allowable limits for aluminum alloy chemical composition. The data for the alloy chemical compositions is published by the Aluminum Association in "International Alloy Designations and Chemical Composition Limits for Wrought Aluminum and Wrought Aluminum Alloys," which was updated in January 2015, and which is incorporated by reference herein. The Aluminum Association also has a similar document for cast alloys. In general, according to the Aluminum Association, the 1000 series of aluminum alloys is composed essentially of pure aluminum with a minimum 99% aluminum content by weight; the 2000 series is aluminum principally alloyed with copper; the 3000 series is aluminum principally alloyed with manganese; the 4000 series is aluminum alloyed with silicon; the 5000 series is aluminum primarily alloyed with magnesium; the 6000 series is aluminum alloyed with magnesium and silicon; the 7000 series is aluminum primarily alloyed with zinc; and the 8000 series is a miscellaneous category.

While it would therefore be beneficial to be able to sort a mass or body of aluminum sheet scrap containing a heterogeneous mixture of pieces of different alloys, to separate the different alloy compositions or at least different alloy families before re-melting for recycling, scrap pieces of different aluminum alloy compositions are not ordinarily visually distinguishable from each other. Optically indistinguishable metals are difficult to sort and, therefore, might be lost. For example, it is not easy to manually separate and identify small pieces of cast from wrought aluminum or to spot zinc or steel attachments encapsulated in aluminum. There also is the problem that color sorting is nearly impossible for identically colored materials, such as the all-gray metals of aluminum alloys, zinc, and lead.

Furthermore, the presence of commingled pieces of different alloys in a body of scrap limits the ability of the scrap to be usefully recycled, unless the different alloys (or, at least, alloys belonging to different compositional families such as those designated by the Aluminum Association series 1000, 2000, 3000, etc.) can be separated prior to re-melting. This is because, when commingled scrap of plural different alloy compositions or composition families is re-melted, the resultant molten mixture contains proportions of the principle alloy and elements (or the different compositions) that are too high to satisfy the compositional limitations of any particular commercial alloy.

Moreover, as evidenced by the production and sale of the 2015 Ford F-150 pickup having a considerable increase in its body and frame parts consisting of aluminum instead of steel, it is additionally desirable to recycle sheet metal scrap, including that generated in the manufacture of automotive components from sheet aluminum. Recycling of the scrap involves re-melting the scrap to provide a body of molten metal that can be cast and/or rolled into useful aluminum parts for further production of such vehicles. However, automotive manufacturing scrap (and metal scrap from other sources such as airplanes and commercial and household appliances) often includes a mixture of scrap pieces of two or more aluminum alloys differing substantially from each other in composition. A specific example of mixed manufacturing scrap of aluminum sheet, generated in certain present-day automotive manufacturing operations, is a mixture of pieces of one or more alloys of the Aluminum Association 5000 series and pieces of one or more alloys of the Aluminum Association 6000 series. Thus, those skilled in the aluminum alloy art will appreciate the difficulties in this art of separating aluminum alloys, especially alloys that have been worked such as forged, extruded, rolled, and generally wrought alloys, into a reusable or recyclable worked product. These alloys for the most part are indistinguishable upon visual inspection or by other conventional scrap sorting techniques such as density and/or eddy-currents. Therefore, it is a difficult task to separate for example, 2000, 3000, 5000, 6000, and 7000 series alloys; moreover, the ability to sort between aluminum alloys within the same Aluminum Association series has not been accomplished in the prior art.

As a result, there are certain economies available to the aluminum industry by developing a well-planned yet simple recycling plan or system. The use of recycled material would be a less expensive metal resource than a primary source of aluminum. As the amount of aluminum sold to the automotive industry (and other industries) increases, it will become increasingly necessary to use recycled aluminum to supplement the availability of primary aluminum.

BRIEF DESCRIPTION OF THE DRAWINGS

FIG. 23 shows elemental compositions for aluminum alloys 6013, 6022, and 6013 as defined by the Aluminum Association.

FIG. 29 shows a comparison of the normalized ECS of FIG. 28 for the exemplary material to normalized standard reference ECS's.

FIGS. 30-31 show an example of classifying aluminum alloys utilizing a dot product method.

FIG. 32 shows ECS values for four exemplary aluminum alloys.

FIG. 33 shows the ECS values of FIG. 33 with error range values.

DETAILED DESCRIPTION

Figure 1:
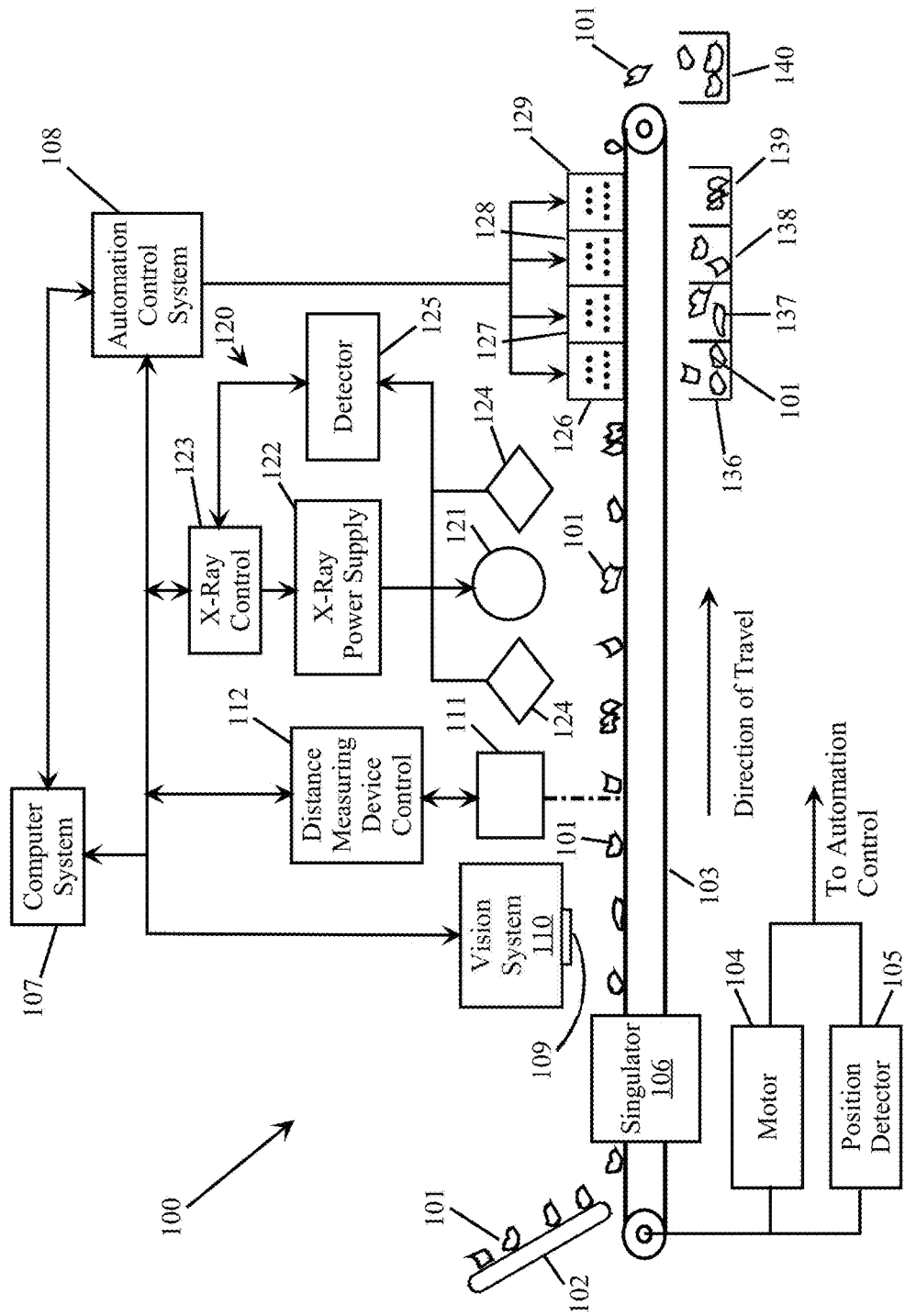
FIG. 1 illustrates a schematic of a sorting system configured in accordance with various embodiments of the present invention.

Detailed embodiments of the present invention are disclosed herein. However, it is to be understood that the disclosed embodiments are merely exemplary of the invention, which may embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

As used herein, a "material" may be a chemical element, a compound or mixture of chemical elements, or a compound or mixture of a compound or mixture of chemical elements, wherein the complexity of a compound or mixture may range from being simple to complex. Materials may include metals (ferrous and nonferrous), metal alloys, plastics, rubber, glass, ceramics, etc. As used herein, "element" means a chemical element of the periodic table of elements, including elements that may be discovered after the filing date of this application. As used herein, the term "aluminum" refers to aluminum metal and aluminum-based alloys, viz., alloys containing more than 50% by weight aluminum (including those classified by the Aluminum Association). As used herein, the terms "scrap" and "scrap pieces" refer to pieces of metal in solid as distinguished from molten state.

As defined within the Guidelines for Nonferrous Scrap promulgated by the Institute Of Scrap Recycling Industries, Inc., the term "Zorba" is the collective term for shredded nonferrous metals, most usually originating from end-of-life vehicles ("ELVs") or waste electronic and electrical equipment ("WEEE"). The Institute Of Scrap Recycling Industries, Inc. ("ISRI") in the United States established the specifications for Zorba. ISRI defines Zorba as "shredded mixed nonferrous metals consisting primarily of aluminum generated by eddy-current separator or other segregation techniques." In Zorba, each metal scrap piece may be made up of a combination of the nonferrous metals: aluminum, copper, lead, magnesium, stainless steel, nickel, tin, and zinc, in elemental or alloyed (solid) form. Furthermore, the term "Twitch" shall mean floated fragmentizer aluminum scrap (from automobile shredders).

In embodiments of the present invention, x-ray fluorescence ("XRF") is described as utilized for determining the compositions of materials (e.g., elements) within samples, such as pieces of scrap (e.g., metal scrap pieces, Zorba, Twitch, etc.). However, embodiments of the present invention may sort samples of materials differing in chemical composition by a number of known processes in which one or more streams of singulated materials is moved passed a radiant source and are irradiated, and the reflected radiation is measured and used to identify or classify the kinds of materials (e.g., metal scrap pieces). For example, instead of the utilization of x-rays emitted from an x-ray tube, isotope radiation may be utilized and the reflected radiation is measured and used for identification/classification.

As used herein, the terms "identify" and "classify," and the terms "identification" and "classification," may be utilized interchangeably. Within embodiments of the present invention, x-ray fluorescence detected from a material may be utilized to identify some or all of the elements present within the material, including the quantities or relative quantities of such elements. Embodiments of the present invention may then utilize the identification of such elements to identify the type of metal alloy (e.g., aluminum alloy) pertaining to the detected fluoresced x-rays. Furthermore, embodiments of the present invention may utilize the identification of the elements within the material in order to classify the material according to a predetermined standard. For example, in accordance with embodiments of the present invention, x-ray fluorescence detected from an aluminum alloy material (e.g., an aluminum alloy scrap piece) may be utilized to assign an aluminum alloy classification to the material (including in accordance with the aluminum alloy classifications designated by the Aluminum Association).

Within x-ray fluorescence spectroscopy, the use of characteristic x-rays emitted under excitation provides a method for identification of elements and their relative amounts present in different materials. The energy of emitted x-rays depends on the atomic number of the fluorescing elements. Energy-resolving detectors are then used to detect the different energy levels at which x-rays are fluoresced, and generate an x-ray signal from the detected x-rays. This x-ray signal may then be used to build an energy spectrum of the detected x-rays, and from the information, the element or elements that produced the x-rays may be identified. Fluorescent x-rays are emitted isotopically from an irradiated element, and the detected radiation depends on the solid angle subtended by the detector and any absorption of this radiation prior to the radiation reaching the detector. The lower the energy of an x-ray, the shorter the distance it will travel before being absorbed by air. Thus, when detecting x-rays, the amount of x-rays detected is a function of the quantity of x-rays emitted, the energy level of the emitted x-rays, the emitted x-rays absorbed in the transmission medium (e.g., air and/or a non-vacuumed environment, or a vacuumed environment), the angles between the detected x-rays and the detector, and the distance between the detector and the irradiated material.

These x-rays cause each piece of material to fluoresce x-rays at various energy levels, depending on the elements contained in the piece. The fluoresced x-rays are detected, and the piece of material is then classified based on the fluoresced x-rays and sorted in accordance with this classification.

Elements or materials with low atomic numbers (such as present within aluminum alloys) do not lend themselves well to x-ray fluorescence analysis, since x-ray photons fluoresced from such low atomic number materials are at a low yield and are low energy (~1-2 keV). Because they are low energy, they are easily absorbed in the air before reaching the detection system. This method also, by nature of the detection system, requires a significant time interval to build and analyze spectral information for each piece of material analyzed. Consequently, systems that operate according to this method are limited in throughput rate of materials. For high throughput rates, it is desired to have a faster acting analysis system in order to process materials faster and at greater volumes. As will be described herein, embodiments of the present invention are able to classify aluminum alloys from each other at a high throughput rate.

Though all embodiments of the present invention may be utilized to sort any type of material as defined herein, embodiments of the present invention are hereinafter described for sorting pieces of metal alloy scrap (also referred to as "metal alloy scrap pieces"), including aluminum alloy scrap pieces.

The material sorting systems described herein according to embodiments of the present invention receive a heterogeneous mix of a plurality of metal alloy scrap pieces, wherein at least one metal alloy scrap piece within this heterogeneous mix includes a composition of elements (e.g., an aluminum alloy) different from one or more other metal alloy scrap pieces, and the sorting system is configured to sort this one metal alloy scrap piece into a group separate from such other metal alloy scrap piece(s).

Embodiments of the present invention will be described herein as sorting metal alloy scrap pieces into such separate groups by physically depositing (e.g., ejecting) the metal alloy scrap pieces into separate receptacles or bins as a function of user-defined groupings (e.g., metal alloy classifications). As an example, within embodiments of the present invention, metal alloy scrap pieces may be sorted into separate bins in order to separate metal scrap pieces composed of a particular metal alloy composition, or compositions, from other metal alloy scrap pieces composed of a different metal alloy composition. Moreover, embodiments of the present invention may sort aluminum alloy scrap pieces into separate bins so that substantially all of the aluminum alloy scrap pieces having a composition falling within one of the aluminum alloy series published by the Aluminum Association are sorted into a single bin (for example, a bin may correspond to one or more particular aluminum alloy series (e.g., 1000, 2000, 3000, 4000, 5000, 6000, 7000, 8000)).

Furthermore, as will be described herein, embodiments of the present invention may be configured to sort aluminum alloy scrap pieces into separate bins as a function of a classification of their alloy composition even if such alloy compositions falls within the same Aluminum Association series. As a result, the sorting system in accordance with embodiments of the present invention can classify and sort aluminum alloy scrap pieces having compositions that would all classify them into a single aluminum alloy series (e.g., the 5000 series or the 6000 series) into separate bins as a function of their aluminum alloy composition. For example, embodiments of the present invention can classify and sort into separate bins aluminum alloy scrap pieces classified as aluminum alloy 5086 separate from aluminum alloy scrap pieces classified as aluminum alloy 5022. Such an ability to sort scrap pieces of aluminum alloys from each other within a particular aluminum alloy series has never been accomplished before in the prior art.

It should be noted that the materials to be sorted may have irregular sizes and shapes. For example, with respect to the sorting of Zorba and Twitch, such material may have been previously run through some sort of shredding mechanism that chops up the scrap metal into such irregularly shaped and sized pieces, which are then fed onto the conveyor system.

FIG. 1 illustrates an example of a material sorting system 100 configured in accordance with embodiments of the present invention. A conveyor system 103 may be implemented to convey one or more streams of metal alloy scrap pieces 101 through the sorting system 100 so that each of the individual metal alloy scrap pieces 101 can be tracked, classified, and sorted into predetermined desired groups. Such a conveyor system 103 may be implemented with one or more conveyor belts on which the metal alloy scrap pieces 101 travel, typically at a predetermined constant speed. However, embodiments of the present invention may be implemented with other types of conveyor systems, including a system in which the metal alloy scrap pieces free fall past the various components of the sorting system. Hereinafter the conveyor system 103 will simply be referred to as the conveyor belt 103.

Furthermore, though FIG. 1 illustrates a single stream of metal alloy scrap pieces 101 on a conveyor belt 103, embodiments of the present invention may be implemented in which there are a plurality of such streams of metal alloy scrap pieces passing by the various components of the sorting system 100 in parallel with each other. For example, as will be further described herein (e.g., see FIG. 3), the metal alloy scrap pieces may be distributed into two or more parallel singulated streams travelling on a single conveyor belt, or a set of parallel conveyor belts. As such, embodiments of the present invention are capable of simultaneously tracking, classifying, and sorting a plurality of such parallel travelling streams of metal alloy scrap pieces.

Some sort of suitable feeder mechanism may be utilized to feed the metal alloy scrap pieces 101 onto the conveyor belt 103, whereby the conveyor belt 103 conveys the metal alloy scrap pieces 101 past various components within the sorting system 100. Within embodiments of the present invention, the conveyor belt 103 is operated to travel at a predetermined speed by a conveyor belt motor 104. This predetermined speed may be programmable and adjustable by the user in any well-known manner. Monitoring of the predetermined speed of the conveyor belt 103 may alternatively be performed with a position detector 105. Within embodiments of the present invention, control of the conveyor belt motor 104 and/or the position detector 105 may be performed by an automation control system 108. Such an automation control system 108 may be operated under the control of a computer system 107, or the functions for performing the automation control may be implemented in software within the computer system 107.

The conveyor belt 103 may be a conventional endless belt conveyor employing a conventional drive motor 104 suitable to move the conveyor belt at the predetermined speeds. The position detector 105 may be a conventional encoder, operatively connected to the conveyor belt 103 and the automation control system 108, to provide continuous information corresponding to the movement of the conveyor belt 103. Thus, as will be further described herein, through the utilization of the controls to the conveyor belt motor 104 and the automation control system 108 (and alternatively including the position detector 105), as each of the metal alloy scrap pieces 101 travelling on the conveyor belt 103 are identified, they then can be tracked by location and time so that the various components of the sorting system 100 can be activated/deactivated as each metal alloy scrap piece 101 passes within their vicinity. As a result, the automation control system 108 is able to track the position of each of the metal alloy scrap pieces 101 while they travel along the conveyor belt 103.

After the metal alloy scrap pieces 101 are received by the conveyor belt 103, they may be positioned into one or more singulated (i.e., single file) streams. This may be performed by an active or passive singulator 106. Furthermore, as described herein, the sorting system 100 may be configured to mechanically position each of the metal alloy scrap pieces 101 within a singulated stream at a relatively constant distance from each other.

Figure 2:
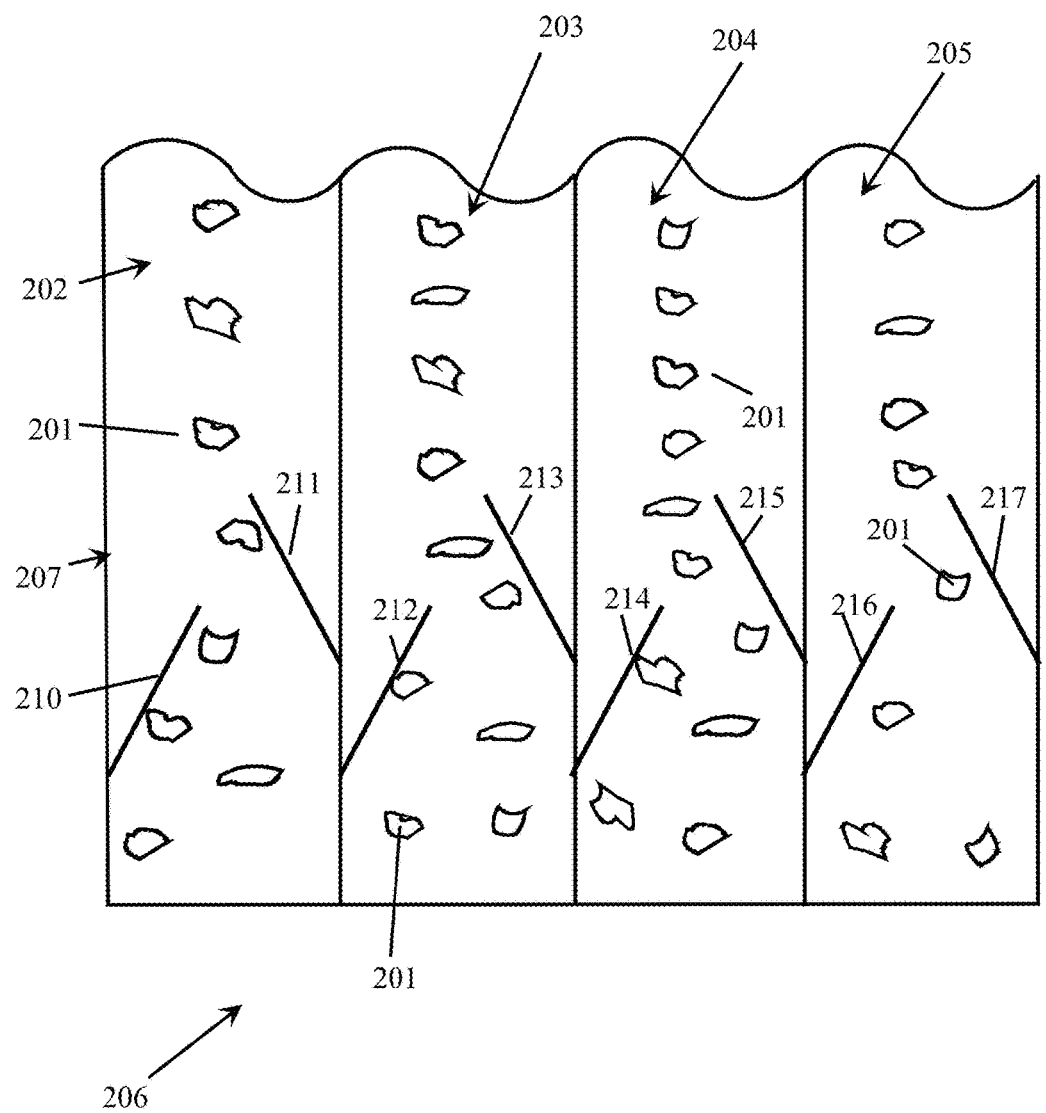
FIG. 2 illustrates a schematic of a device for passively singulating one or more streams of materials.

An example of a passive singulator 206 is illustrated in FIG. 2, which schematically shows how static alignment rods or bars 210 . . . 217 align the individual metal alloy scrap pieces 201 into one or more singulated streams on a conveyor belt. Though the example of FIG. 2 is not limiting, it does illustrate how the metal alloy scrap pieces 201 can be singulated into four separate singulated streams 202 . . . 205 of metal alloy scrap pieces 201 on a conveyor belt 207. Within embodiments of the present invention, a single conveyor belt may transport such a plurality of singulated streams, or a plurality of individually driven conveyor belts may be utilized whereby each of the conveyor belts conveys one of the separate singulated streams (e.g., 202 . . . 205) of metal alloy scrap pieces 201.

Referring again to FIG. 1, embodiments of the present invention may utilize a vision system 110 and/or a distance measuring device 111 as a means to begin tracking each of the metal alloy scrap pieces 101 as they travel on the conveyor belt 103. The vision system 110 may utilize one or more still or live action cameras 109 to note the position (i.e., location and timing) of each of the metal alloy scrap pieces 101 on the moving conveyor belt 103. Such a vision system 110 may be further configured to perform certain types of identification of all or a portion of the metal alloy scrap pieces 101. For example, such a vision system 110 may be utilized to acquire additional information about each of the metal alloy scrap pieces 101, including information that the x-ray fluorescence ("XRF") system 120 cannot gather alone. For example, the vision system 110 may be configured to collect information about color, size, shape, and/or uniformity of the metal alloy scrap pieces 101, which can aid in the identification of the compositions of such metal alloy scrap pieces 101. Additionally, such a vision system 110 can be configured to identify which of the metal alloy scrap pieces 101 are not of the kind to be sorted by the sorting system 100, and send a signal to reject such pieces before they reach the XRF system 120. In such a configuration, such identified pieces 101 may be ejected utilizing one of the mechanisms as described hereinafter for physically moving sorted metal alloy scrap pieces into individual bins. Alternatively, both the vision system 110 and the XRF system 120 may be used to classify the metal alloy scrap pieces 101 with a higher degree of reliability than can be performed by the vision or XRF systems alone. This can include classifying various metal (e.g., aluminum) alloys relative to each other.

A distance measuring device 111 and control system 112 may be utilized and configured to measure the sizes and/or shapes of each of the metal alloy scrap pieces 101 as they pass within proximity of the distance measuring device 111, along with the position (i.e., location and timing) of each of the metal alloy scrap pieces 101 on the moving conveyor belt 103. An exemplary operation of such a distance measuring device 111 and control system 112 is described herein with respect to FIG. 5. Such a distance measuring device 111 may be implemented with a well-known laser light system, which continuously measures a distance the laser light travels before being reflected back into a detector of the laser light system. As such, as each of the metal alloy scrap pieces 101 passes within proximity of the device 111, it outputs a signal to the distance measuring device control system 112 indicating such distance measurements. Therefore, such a signal may substantially represent an intermittent series of pulses whereby the baseline of the signal is produced as a result of a measurement of the distance between the distance measuring device 111 and the conveyor belt 103 during those moments when a scrap piece is not in the proximity of the device 111, while each pulse provides a measurement of the distance between the distance measuring device 111 and a metal alloy scrap piece 101 passing by on the conveyor belt 103. Since the metal alloy scrap pieces 101 may have irregular shapes, such a pulse signal may also occasionally have an irregular height. Nevertheless, each pulse signal generated by the distance measuring device 111 provides the height of portions of each of the metal alloy scrap pieces 101 as they pass by on the conveyor belt 103. The length of each of such pulses also provides a measurement of a length of each of the metal alloy scrap pieces 101 measured along a line substantially parallel to the direction of travel of the conveyor belt 103. It is this length measurement (corresponding to the time stamp of process block 506 of FIG. 5) (and alternatively the height measurements) that may be utilized within embodiments of the present invention to determine when to activate and deactivate the acquisition of detected fluorescence (i.e., the XRF spectrum) of each of the metal alloy scrap pieces 101 by the XRF system 120.

Each of the embodiments of the present invention may solely utilize a vision system, or systems, solely utilize a distance measurement device, or a combination thereof.

The XRF system 120 is configured to identify the composition, or relative compositions, of each of the metal alloy scrap pieces 101 as they pass within proximity of the XRF system 120. An exemplary operation of such an XRF system 120 is described herein with respect to FIG. 6. The XRF system 120 includes an x-ray source 121, which may be powered by an x-ray power supply 122.

Within embodiments of the present invention, the x-ray source 121 may include any well-known commercially available x-ray tube, or commercially available x-ray sources using radioactive isotopes. Though such isotope-based sources do not typically produce x-rays at the intensity that can be produced by a commercially available x-ray tube, embodiments of the present invention are capable of sufficiently classifying metal alloys, including aluminum alloys (even within the same aluminum alloy series) for sorting into separate bins, utilizing such isotope-based sources. Since when an x-ray source producing less intense x-rays results in less x-rays being fluoresced from the metal alloy scrap pieces, the sorting system may be preprogrammed to decrease the speed of the conveyor belt to allow fluoresced x-rays to be detected by the one or more detectors from the metal alloy scrap pieces for a longer period of time so that an XRF spectrum with a strong enough image, i.e., a recognizable spectral pattern, may be determined.

As will be described herein with respect to FIGS. 9-13, the x-ray source may include an in-line x-ray fluorescence ("IL-XRF") tube. Such an IL-XRF tube may include a separate x-ray source dedicated for one or more of the singulated streams of conveyed metal alloy scrap pieces. Likewise, one or more XRF detectors may be implemented to detect fluoresced x-rays from metal alloy scrap pieces within each of the singulated streams.

Figure 22:
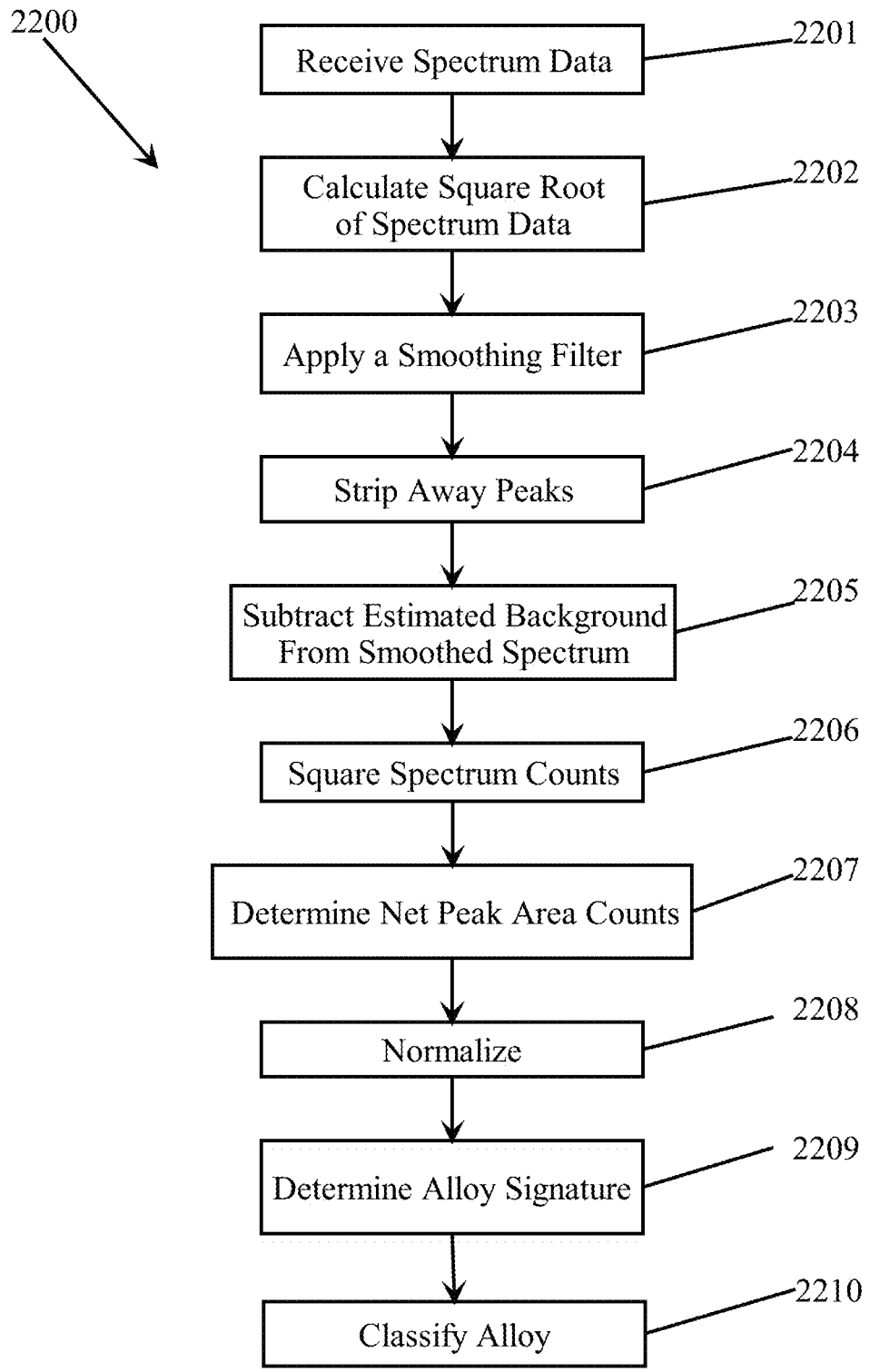
FIG. 22 illustrates a flowchart diagram, configured in accordance with embodiments of the present invention, of a system and process for classifying materials using x-ray fluorescence.

As each metal alloy scrap piece 101 passes within proximity to the x-ray source 121, it is irradiated with x-rays from the x-ray source 121 resulting in an x-ray fluorescence spectrum emanating from the irradiated metal alloy scrap piece 101. One or more XRF detectors 124 (e.g., see FIG. 16) are positioned and configured for detecting the x-ray fluorescence emanated from the metal alloy scrap piece 101. The one or more detectors 124 and the associated detector electronics 125 capture this received XRF spectrum to perform signal processing thereon and produce digitized information representing the captured XRF spectrum, which is then analyzed in accordance with embodiments of the present invention in order to identify/classify each of the metal alloy scrap pieces 101 (e.g., see FIGS. 7 and 22). This classification, which may be performed within the computer system 107, may then be utilized by the automation control system 108 to activate one of the N (N≥1) sorting devices 126 . . . 129 for sorting (e.g., ejecting) the metal alloy scrap pieces 101 into one or more N (N≥1) sorting bins 136 . . . 139 according to the determined classifications (e.g., see FIG. 8). Four sorting devices 126 . . . 129 and four sorting bins 136 . . . 139 associated with the sorting devices are illustrated in FIG. 1 as merely a non-limiting example.

The sorting devices may include any well-known mechanisms for ejecting the metal alloy scrap pieces from the conveyor belt system into the plurality of sorting bins. For example, a sorting device may utilize air jets, with each of the air jets assigned to one or more of the classifications. When one of the air jets (e.g., 127) receives a signal from the automation control system 108, that air jet emits a stream of air that causes a metal alloy scrap piece 101 to be ejected from the conveyor belt 103 into a sorting bin (e.g., 137) corresponding to that air jet. High speed air valves from Mac Industries may be used, for example, to supply the air jets with air pressure configured to eject the metal alloy scrap pieces 101 from the conveyor belt 103.

Figure 3:
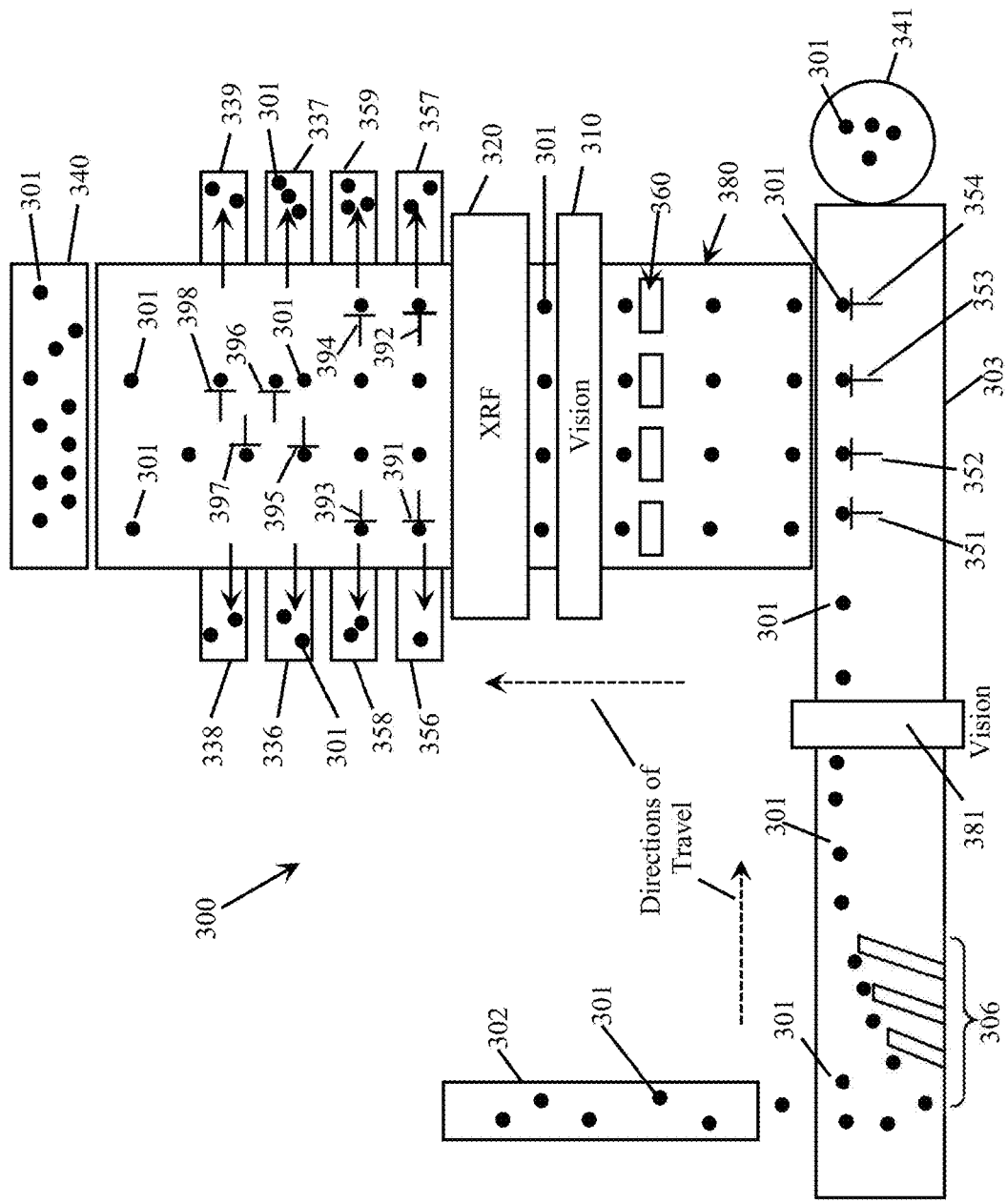
FIG. 3 illustrates a schematic of a sorting system configured in accordance with embodiments of the present invention.

Although the example illustrated in FIG. 1 uses air jets to eject metal alloy scrap pieces, other mechanisms may be used to eject the metal alloy scrap pieces, such as robotically removing the metal alloy scrap pieces from the conveyor belt, pushing the metal alloy scrap pieces from the conveyor belt (e.g., with paint brush type plungers), or causing an opening (e.g., a trap door) in the conveyor belt 103 from which a metal alloy scrap piece may drop. As an example, FIG. 3 shows an exemplary embodiment in which plungers are utilized to eject the metal alloy scrap pieces from a conveyor belt.

In addition to the N sorting bins 136 . . . 139 into which metal alloy scrap pieces 101 are ejected, the system 100 may also include a receptacle or bin 140 that receives metal alloy scrap pieces 101 not ejected from the conveyor belt 103 into any of the aforementioned sorting bins 136 . . . 139. For example, a metal alloy scrap piece 101 may not be ejected from the conveyor belt 103 into one of the N sorting bins 136 . . . 139 when the classification of the metal alloy scrap piece 101 is not determined (or simply because the sorting devices failed to adequately eject a piece). Thus, the bin 140 may serve as a default receptacle into which unclassified metal alloy scrap pieces are dumped. Alternatively, the bin 140 may be used to receive one or more classifications of metal alloy scrap pieces that have deliberately not been assigned to any of the N sorting bins 136 . . . 139.

Depending upon the variety of classifications of metal alloy scrap pieces desired, multiple classifications may be mapped to a single sorting device and associated sorting bin. In other words, there need not be a one-to-one correlation between classifications and sorting bins. For example, it may be desired by the user to sort certain classifications of metal alloys (e.g., aluminum alloys) into the same sorting bin. To accomplish this sort, when a metal alloy scrap piece 101 is classified as a metal alloy falling into a predetermined grouping of metal alloy classifications, the same sorting device may be activated to sort these into the same sorting bin. Such combination sorting may be applied to produce any desired combination of sorted metal alloy scrap pieces and element distribution. The mapping of classifications may be programmed by the user (e.g., using the sorting algorithm (e.g., see FIGS. 7 and 22) operated by the computer system 107) to produce such desired combinations. Additionally, the classifications of metal alloy scrap pieces are user-definable, and not limited to any particular known classification of metal alloy scrap pieces.

Although the conveyor belt 103 may be made of some sort of rubberized material, the intensity of the x-rays generated from the x-ray source 121 may cause even elements present in the conveyor belt 103 to fluoresce x-rays. As a result, within embodiments of the present invention, the conveyor belt 103 may be made of a material that will not fluoresce x-rays at energy levels that fall within a range of the energy spectrum being detected, thereby interfering with the detected energy spectrum. The energy levels of the fluoresced x-rays depend on the energy levels at which the elements present in the metal alloy scrap pieces 101 fluoresce. The energy levels at which an element fluoresces is proportional to its atomic number. For example, elements of low atomic numbers fluoresce x-rays at lower energy levels. Thus, the materials for the conveyor belt 103 may be chosen such that the belt 103 includes elements of certain atomic numbers that do not fluoresce x-rays within a certain energy range.

Within embodiments of the present invention, the x-ray source 121 may be located above the detection area (i.e., above the conveyor belt 103); however, embodiments of the present invention may locate the x-ray source 121 and/or detectors 124 in other positions that still produce acceptable detected XRF spectra. Moreover, the detector electronics 125 may include well-known amplifiers for amplifying one or more of the received energy levels of the fluoresced x-rays, whereby such amplified energy levels are then processed within the detector electronics 125 to be normalized with other energy levels not similarly amplified.

Signals representing the detected XFR spectrum may be converted into a discrete energy histogram such as on a per-channel (i.e., element) basis, as further described herein. Such a conversion process may be implemented within the x-ray control system 123, or the computer system 107. Within embodiments of the present invention, such an x-ray control system 123 or computer system 107 may include a commercially available spectrum acquisition module, such as the commercially available Amptech MCA 5000 acquisition card and software programmed to operate the card. Such a spectrum acquisition module, or other software implemented within the sorting system 100 may be configured to implement a plurality of channels for dispersing x-rays into a discrete energy spectrum (i.e., histogram) with such a plurality of energy levels, whereby each energy level corresponds to an element that the sorting system 100 has been configured to detect. The system 100 may be configured so that there are sufficient channels corresponding to certain elements within the chemical periodic table, which are important for distinguishing between different metal (e.g., aluminum) alloys. The energy counts for each energy level may be stored in a separate collection storage register. The computer system 107 then reads each collection register to determine the number of counts for each energy level during the collection interval, and build the energy histogram. As will be described in more detail herein, a sorting algorithm configured in accordance with embodiments of the present invention may then utilize this collected histogram of energy levels to classify each of the metal alloy scrap pieces 101 (e.g., see FIGS. 7,17-22, 24-29, and 32-33).

The conveyor belt 103 may include a circular conveyor (not shown) so that unclassified metal alloy scrap pieces are returned to the beginning of the sorting system 100 to be singulated by the singulator 106 and run through the system 100 again. Moreover, because the system 100 is able to specifically track each metal alloy scrap piece 101 as it travels on the conveyor system 103, some sort of sorting device (e.g., 129) may be implemented to eject a metal alloy scrap piece 101 that the system 100 has failed to classify after a predetermined number of cycles through the sorting system 100 (or the metal alloy scrap piece 101 is collected in bin 140).

Within embodiments of the present invention, the conveyor belt 103 may be divided into multiple belts configured in series such as, for example, two belts, where a first belt conveys the metal alloy scrap pieces pass the XRF system, and a second belt conveys the metal alloy scrap pieces from the XRF system to the sorting devices. Moreover, such a second conveyor belt may be at a lower height than the first conveyor belt, such that the metal alloy scrap pieces fall from the first belt onto the second belt.

Referring now to FIG. 3, there is illustrated further exemplary embodiments of the present invention in which various alternative and optional aspects of a sorting system 300 are depicted. It should be noted that one of ordinary skill in the art would be able to configure a sorting system similar to those illustrated in FIG. 1 or 3, or a different sorting system that combines various aspects and components from each of these two depicted exemplary sorting systems.

Referring to FIG. 3, the metal alloy scrap pieces 301 are deposited onto a conveyor system, such as via a ramp or chute 302 so that the metal alloy scrap pieces 301 land onto a feeder conveyor belt 303 travelling in the noted direction of travel. In order for the metal alloy scrap pieces to move in a singulated stream within proximity to the XRF system, the metal alloy scrap pieces 301 may be separated and then positioned into a line. A first optional step may include the use of a mechanism, such as a tumbler or a vibrator (not shown), to separate individual pieces from a collection of pieces. Aspects of the present disclosure may include the use of a multiple belt (e.g., 2 or more) conveyor system with gates (e.g., pneumatic) and sensors (e.g., electronic) in order to align the metal alloy scrap pieces into one or more singulated streams for alloy classification. For example, a passive singulator (e.g., static alignment rods or bars) 306 (or one similar to the singulator 206 of FIG. 2) may then be utilized to force the metal alloy scrap pieces 301 into one or more singulated streams on the feeder conveyor belt 303. A vision, or optical recognition, system 381 may be optionally implemented in order to begin the identification, tracking, and/or classification of the metal alloy scrap pieces 301, as has been described herein with respect to the vision system 110 of FIG. 1.

As the singulated stream of metal alloy scrap pieces 301 travels further down along (downstream) the conveyor belt 303, they then may be pushed by a robotic mechanism (such as N (N≥1) pneumatically actuated paint brush type plungers 351 . . . 354) onto another conveyor belt (or plurality of conveyor belts) 380 to form N (N≥1) singulated streams of metal alloy scrap pieces 301 for travelling along the second conveyor belt 380. For purposes of illustration of embodiments of the present invention, a non-limiting example of four singulated streams is illustrated in FIG. 3. A collector receptacle 341 may be positioned at the end of the first conveyor belt 303 to collect any metal alloy scrap pieces 301 that are not ejected onto the second conveyor belt 380. Alternatively, the first conveyor belt 303 may be a circular conveyor belt (not shown) whereby such metal alloy scrap pieces 301 are returned to the beginning of the first conveyor belt 303 for again being singulated by the singulation device 306. As discussed herein with respect to FIG. 1, one or both of the conveyor belts 303, 380 may be motorized by a conveyor belt motor (e.g., see FIG. 1) to run at one or more predetermined speeds as controlled by the sorting system 300. Additionally, each of these one or more conveyor belts 303, 380 may also be configured to include a position detector (e.g., see FIG. 1) to assist in tracking of each of the metal alloy scrap pieces 301 as they travel along the second conveyor belt system 380.

Accordingly, each piece 301 may be tracked by a process, such as implemented within a computer system, with the use of the vision system 381 and/or the vision system 310, or other detectors (not shown). For example, different types of detectors or sensors may be used in order to detect the location of each piece 301 on the conveyor belts 303, 380 (e.g., UV, IR, laser, sound). Each piece 301 may be detected in order to assign a location of that piece 301 for a given time. Based on that time/location measurement, the rest of the processes performed along the conveyor system are calculated so that different actions by the different components in the sorting system 300 take place at the appropriate time. For example, on the conveyor belt 380, there may be sensors that are placed at the beginning of the conveyor belt 380 to track the time and location of each piece 301. The system 300 then anticipates when each piece will reach the vision system 310. In this fashion, the tracking process can relate the vision information to that unique piece 301. The vision information is then added to that piece 301, and the time to XRF analysis 320 is determined. After the piece 301 leaves the XRF analysis region 320, the tracking process is then able to associate the XRF information pertaining to the piece to the vision information. The system 300 can then identify the piece 301 and then decide which pneumatic 391 . . . 398 to use to push (eject) the piece 301 off the conveyor belt 380. The system 300 knows when to eject each piece 301 because the system 300 has tracked this piece 301 in both location and time. As such, the sorting process uses tracking in order to maintain the location and unique identity of each piece 301 throughout all stages of the sorting process.

As the N singulated streams of metal alloy scrap pieces 301 begin travelling on the second conveyor belt 380, an optional mechanically operated gating mechanism 360 may be utilized to evenly space the metal alloy scrap pieces 301 from each other within each of the singulated streams. Optionally, the vision, or optical recognition, system 310 may be utilized to assist in such a spacing process and/or to identify, track, and/or classify each of the metal alloy scrap pieces 301 within each of the singulated streams, as described herein. Note that embodiments of the present invention do not require that the plurality of singulated streams have the metal alloy scrap pieces 301 evenly spaced from each other within each stream.

Each of the singulated streams of metal alloy scrap pieces 301 then pass within the proximity of the XRF system 320. One or more x-ray sources as described herein may be implemented to irradiate each of the metal alloy scrap pieces 301 within each of the singulated streams. In embodiments of the present invention, each singulated stream of metal alloy scrap pieces 301 may be irradiated by a separately controlled x-ray source. As will be described herein with respect to FIGS. 9-13, the x-ray source may include an in-line x-ray fluorescence ("IL-XRF") tube. Such an IL-XRF tube may include a separate x-ray source dedicated for each of the singulated streams of conveyed metal alloy scrap pieces, or may utilize M (M≥1) x-ray sources to irradiate the N streams. Likewise, one or more XRF detectors may be implemented to detect fluoresced x-rays from metal alloy scrap pieces within each of the singulated streams. Detector electronics (e.g., see FIG. 1) may then be coupled to each of these XRF detectors to receive the signals corresponding to the detected x-ray fluorescence from each of the metal alloy scrap pieces 301, which are then transmitted in a manner as described herein to an XRF processing module and/or a computer system (e.g., see FIG. 1) implementing a classification module for classifying each of the metal alloy scrap pieces 301 within each of the singulated streams (e.g., see FIGS. 7 and 22).

In embodiments of the present invention, N (N≥1) sorting devices may be configured (e.g., see FIG. 8) to eject classified metal alloy scrap pieces 301 into corresponding sorting bins from the conveyor belt 380. Again, any type of well-known sorting device may be utilized (e.g., air jets, paint brush type plungers, robotic or pneumatic pistons, etc.). In the non-limiting example of FIG. 3, N sorting devices 391 . . . 394 may be utilized to eject classified metal alloy scrap pieces 301 into corresponding sorting bins 356 . . . 359 from the two outside singulated streams while the singulated streams lying within the center portion of the conveyor belt 380 continue to travel along the conveyor belt 380 to additional N sorting devices 395 . . . 398 where metal alloy scrap pieces 301 travelling along these inner singulated streams are ejected into corresponding sorting bins 336 . . . 339 in accordance with their determined classification by the sorting algorithm.

Within embodiments of the present invention, any metal alloy scrap pieces 301 not ejected from the conveyor belt 380 by these two sets of sorting devices may then be collected by the receptacle 340, or may be returned for processing through another cycle through the sorting system, by either travelling along a circular conveyor system (not shown) or by the receptacle 340 being physically moved to the beginning of the sorting system 300 for distribution of such metal alloy scrap pieces 301 onto the first conveyor belt 303.

It should be appreciated that embodiments of the present invention may be implemented so that any number of N (N≥1) singulated streams of metal alloy scrap pieces 301 may be sorted by such a sorting system 300. For example, if four alloys are to be separated, then four sorting devices may be required to push each alloy into one of four bins. In order to increase the rate of separation, multiple rows of sorting devices can be used. For example, if four rows of sorting devices were used, with four sorting devices per line, 16 total sorting devices would be positioned over the conveyor belt 380 in order to sort four alloys into 16 total bins. The singulated lines could be placed parallel to each other, and follow a sequential pattern to sort the pieces 301, where the outer two lines are sorted first, then the following inner lines are sorted. This method for using multiples lines for sorting is not limited to four lines but can increase to larger numbers of lines.

Figure 4:
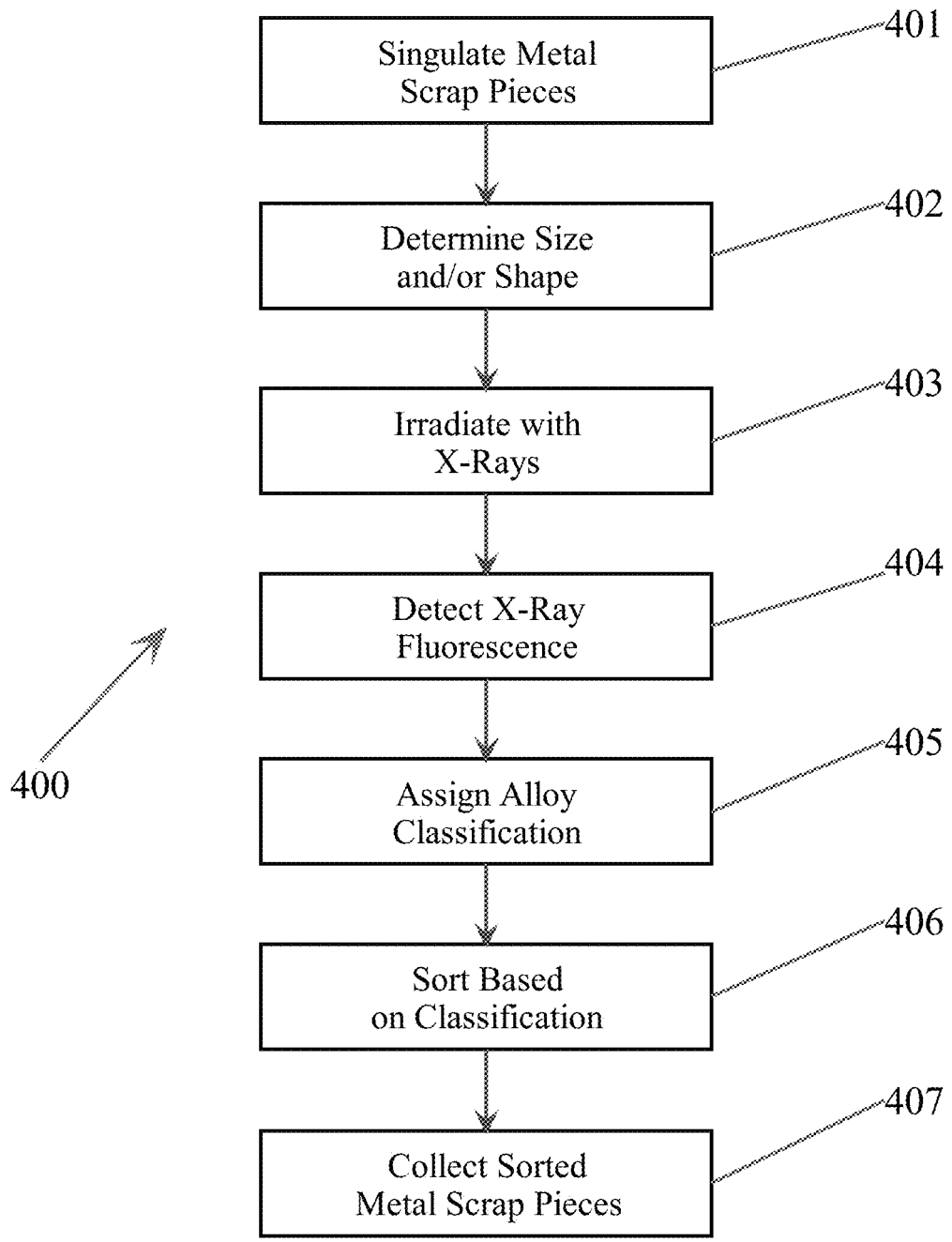
FIG. 4 illustrates a flowchart diagram configured in accordance with embodiments of the present invention.

FIG. 4 illustrates a flowchart diagram depicting exemplary embodiments of a process 400 of sorting metal alloy scrap pieces in accordance with embodiments of the present invention. The process 400 may be configured to operate within any of the embodiments of the present invention described herein, including the sorting system 100 of FIG. 1 and the sorting system 300 of FIG. 3. Operation of the process 400 may be performed by hardware and/or software, including within a computer system (e.g., computer system 3400 of FIG. 34) controlling the sorting system (e.g., the computer system 107 of FIG. 1). In process block 401, the metal alloy scrap pieces may be manipulated into one or more singulated streams onto a conveyor belt. Next, in process block 402, the metal alloy scrap pieces may be conveyed along the conveyor belt within proximity of a distance measuring device and/or a vision system in order to determine a size and/or shape of the metal alloy scrap pieces (e.g., see FIG. 5). In process block 403, when a metal alloy scrap piece has traveled in proximity of the XRF system, the metal alloy scrap piece is irradiated with x-rays. The exposure to the x-rays from the x-ray source causes the metal alloy scrap piece to fluoresce x-rays at various energy levels, producing an XRF spectrum, which has counts dependent upon the various elements present within the metal alloy scrap piece. In process block 404, this XRF fluorescence spectrum is detected by the one or more x-ray detectors (e.g., see FIG. 6). In process block 405, for each metal alloy scrap piece, the metal alloy is identified/classified based on the detected XRF spectrum (e.g., see FIGS. 7 and 22).

Figure 8:
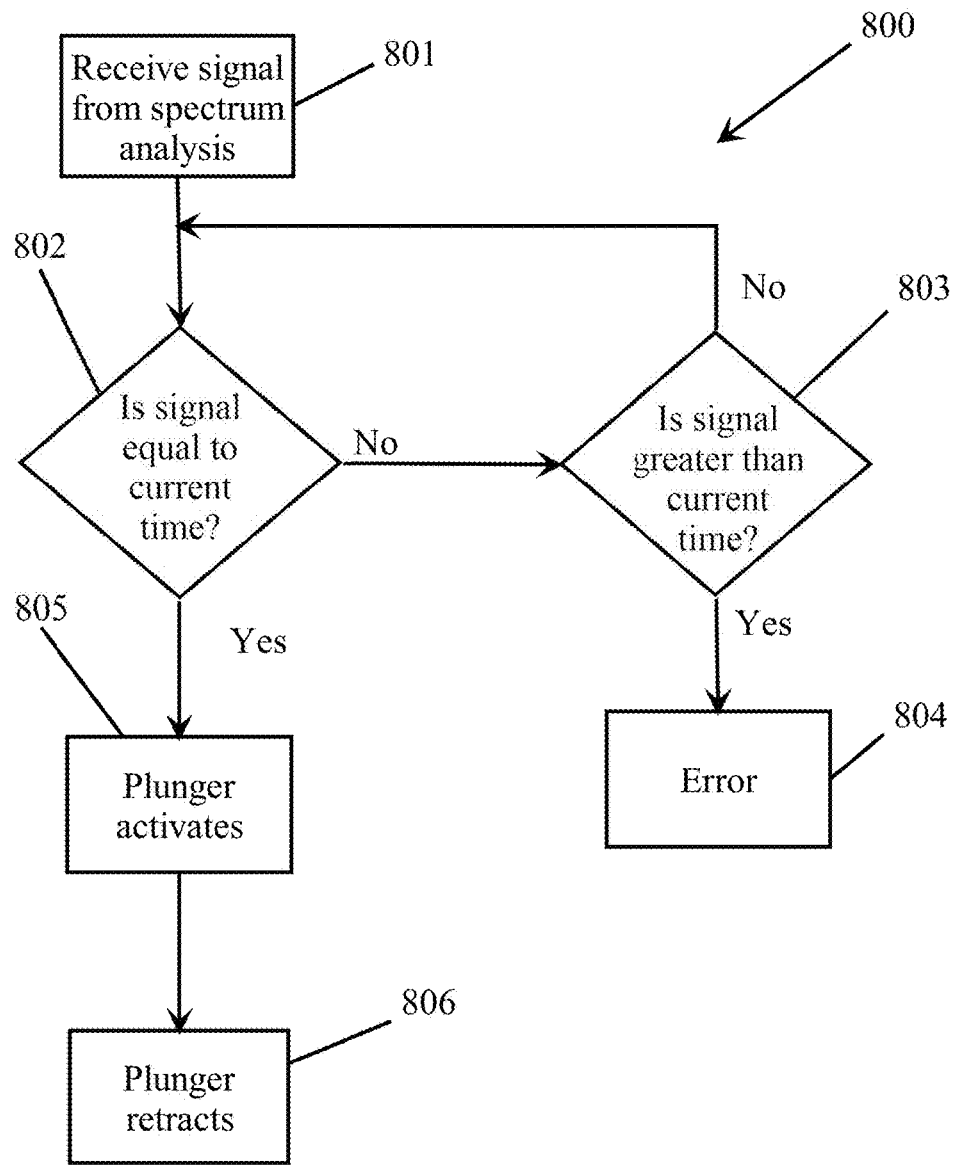
FIG. 8 illustrates a flowchart diagram of an operation of a sorting device configured in accordance with embodiments of the present invention.

Next, in process block 406, a sorting device corresponding to the classification, or classifications, of the metal alloy scrap piece is activated (e.g., see FIG. 8). Between the time at which the metal alloy scrap piece was irradiated and the time at which the sorting device is activated, the metal alloy scrap piece has moved from the proximity of the XRF system to a location downstream on the conveyor belt, at the rate of conveying of the conveyor belt. In embodiments of the present invention, the activation of the sorting device is timed such that as the metal alloy scrap piece passes the sorting device mapped to the classification of the metal alloy scrap piece, the sorting device is activated, and the metal alloy scrap piece is ejected from the conveyor belt into its associated sorting bin. Within embodiments of the present invention, the activation of a sorting device may be timed by a respective position detector that detects when a metal alloy scrap piece is passing before the sorting device and sends a signal to enable the activation of the sorting device. In step 407, the sorting bin corresponding to the sorting device that was activated receives the ejected metal alloy scrap piece.

Figure 16:
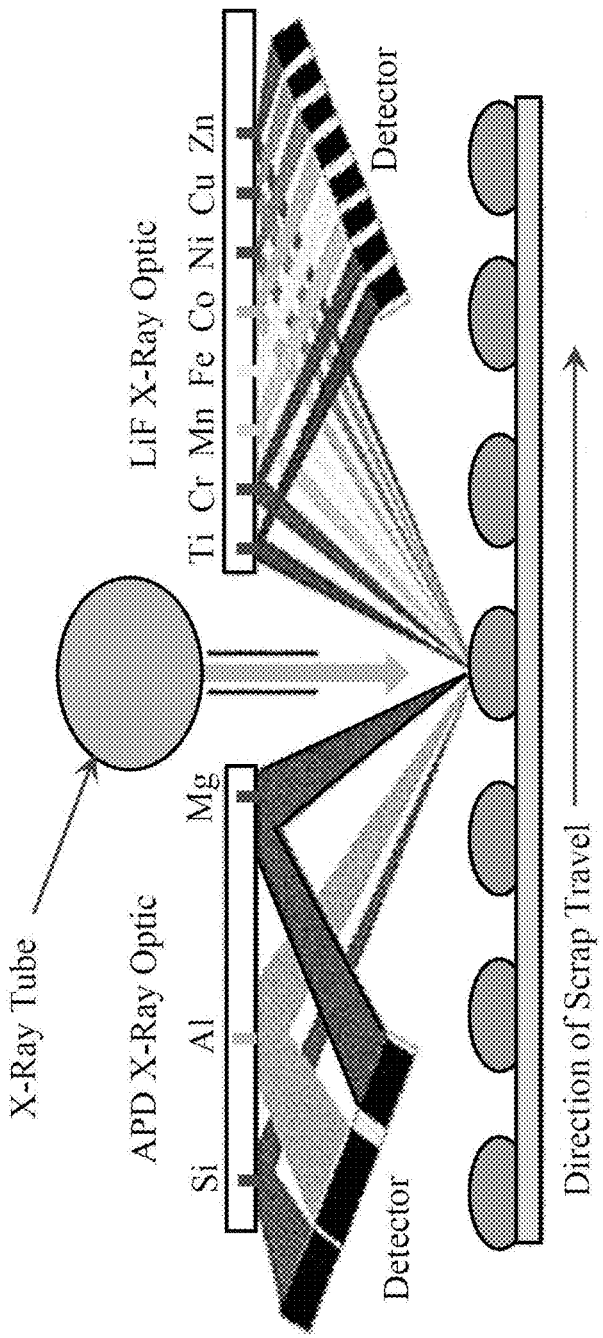
FIG. 16 schematically illustrates an exemplary XRF detector configured in accordance with embodiments of the present invention.

As has been described herein, embodiments of the present invention may utilize one or more detectors (e.g., see detectors 124 of FIG. 1) for detecting the fluoresced x-rays from the irradiated metal alloy scrap pieces. Any well-known commercially available x-ray detector may be utilized. Furthermore, two or more such detectors may be implemented that each detect fluoresced x-rays for the same number of elements to be detected within the metal alloy scrap pieces. Alternatively, as illustrated in the exemplary depiction of FIG. 16, one of the detectors may be configured to detect fluoresced x-rays for one or more predetermined elements while another detector is configured to detect fluoresced x-rays for other elements. The example depicted schematically in FIG. 16 shows one of the detectors configured to detect fluoresced x-rays for the elements silicon, aluminum, and magnesium, while the other detector is configured to detect fluoresced x-rays for the elements titanium, chromium, manganese, iron, cobalt, nickel, copper, and zinc. However, embodiments of the present invention should not be limited to the particular configuration illustrated in FIG. 16. Within embodiments of the present invention, the x-ray detectors may utilize a collimator (not shown) in which an aperture of the collimator is configured such that the detector directly receives fluoresced x-rays from the metal alloy scrap piece while extraneous x-rays including x-rays irradiated from the x-ray source and incidental x-rays from other objects within the vicinity of the detector(s) are inhibited by the collimator from reaching the detector(s), thereby reducing detection of these extraneous x-rays.

Figure 5:
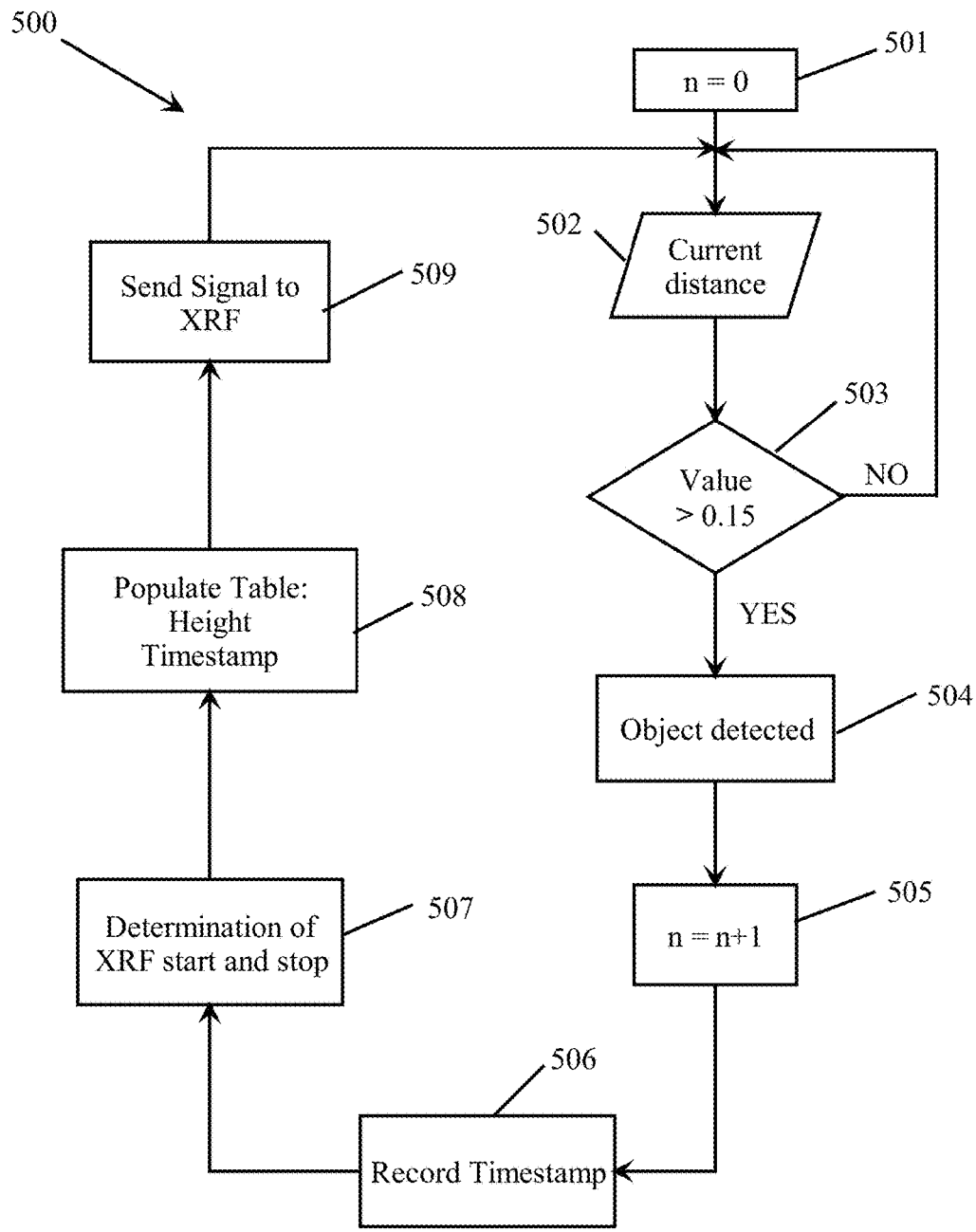
FIG. 5 illustrates a flowchart diagram of an operation of a distance measurement system configured in accordance with embodiments of the present invention.

Referring next to FIG. 5, there is illustrated a flowchart diagram of an exemplary system and process 500 for determining the approximate sizes and/or shapes of each metal alloy scrap piece. Such a system and process 500 may be implemented within any of the vision/optical recognition systems and/or a distance measuring device described herein, such as the distance measuring device illustrated in FIG. 1. In process block 501, the distance measuring device may be initialized at n=0 whereby n represents a condition whereby the first metal alloy scrap piece to be conveyed along the conveyor system has yet to be measured. As previously described, such a distance measuring device may establish a baseline signal representing the distance between the distance measuring device and the conveyor belt absent any presence of an object (i.e., a metal alloy scrap piece) carried thereon. In process block 502, the distance measuring device produces a continuous, or substantially continuous, measurement of distance. Process block 503 represents a decision within the distance measuring device whether the detected distance has changed to be greater than a predetermined threshold amount. Recall that once a sorting system has been initiated, at some point in time, a metal alloy scrap piece will travel along the conveyor system in sufficient proximity to the distance measuring device as to be detected by the employed mechanism by which distances are measured. In embodiments of the present invention, this may occur when a travelling metal alloy scrap piece passes within the line of a laser light utilized for measuring distances. Once an object, such as a metal alloy scrap piece, begins to be detected by the distance measuring device (e.g., a laser light), the distance measured by the distance measuring device will change from its baseline value. The distance measuring device may be predetermined to only detect the presence of a metal alloy scrap piece passing within its proximity if a height of any portion of the metal alloy scrap piece is greater than the predetermined threshold distance value. FIG. 5 shows an example whereby such a threshold value is 0.15 (e.g., representing 0.15 mm), though embodiments of the present invention should not be limited to any particular value.

The system and process 500 will continue (i.e., repeat process blocks 502-503) to measure the current distance as long as this threshold distance value has not been reached. Once a measured height greater than the threshold value has been detected, the process will proceed to process block 504 to record that an object passing within proximity of the distance measuring device has been detected on the conveyor system. Thereafter, in process block 505, the variable n may be incremented to indicate to the sorting system that another object has been detected on the conveyor system. This variable n may be utilized in assisting with tracking of each of the metal alloy scrap pieces within each stream. In process block 506, a time stamp is recorded for the detected object, which may be utilized by the sorting system to track the specific location and timing of a detected metal alloy scrap piece as it travels on the conveyor system, while also representing a length of the detected metal alloy scrap piece. In process block 507, this recorded time stamp may then be utilized for determining when to activate (start) and deactivate (stop) the acquisition of an x-ray fluorescence spectrum from a metal alloy scrap piece associated with the time stamp. The start and stop times of the time stamp may correspond to the aforementioned pulse signal produced by the distance measuring device. In process block 508, this time stamp along with the recorded height of the metal alloy scrap piece may be recorded within a table utilized by the sorting system to keep track of each of the metal alloy scrap pieces and their resultant classification by the XRF system.

Thereafter, in process block 509, signals are then sent to the XRF system indicating the time period in which to activate/deactivate the acquisition of an x-ray fluorescence spectrum from the metal alloy scrap piece, which may include the start and stop times corresponding to the length of the metal alloy scrap piece determined by the distance measuring device. Embodiments of the present invention are able to accomplish such a task because of the time stamp and known predetermined speed of the conveyor system received from the distance measuring device indicating when a leading edge of the metal alloy scrap piece will pass by the x-ray beam from the x-ray source, and when the trailing edge of the metal alloy scrap piece will thereafter pass by the x-ray beam.

The system and process 500 for distance measuring of each of the metal alloy scrap pieces travelling along the conveyor system is then repeated for each passing metal alloy scrap piece.

Figure 6:
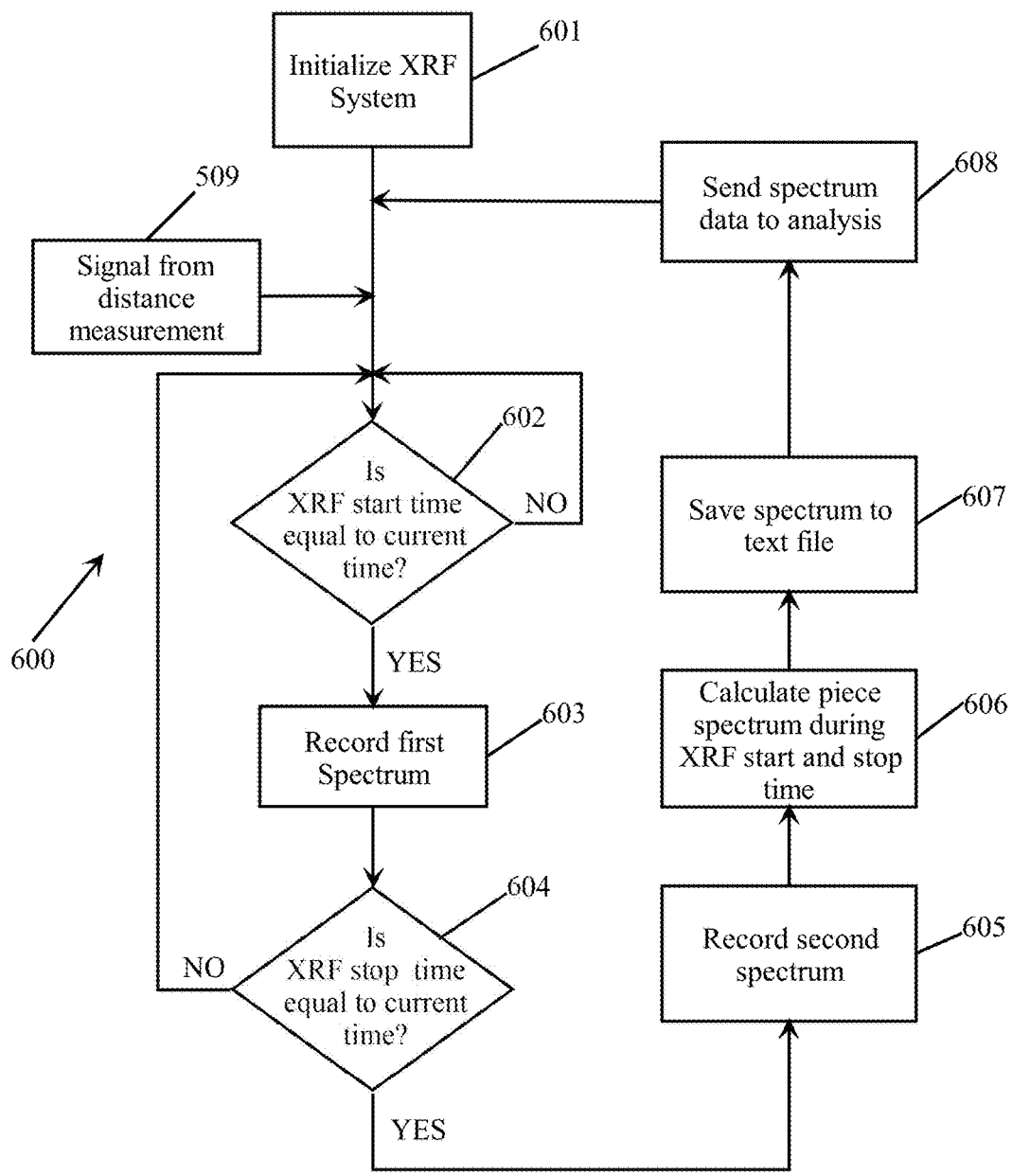
FIG. 6 illustrates a flowchart diagram of an operation of an x-ray fluorescence ("XRF") system configured in accordance with embodiments of the present invention.

Referring next to FIG. 6, there is illustrated a system and process 600 for acquiring an x-ray fluorescence spectrum from each of the metal alloy scrap pieces in accordance with embodiments of the present invention. Such a system and process 600 may be implemented within any of the XRF systems described herein. At the start-up of the sorting system, the XRF system may be initialized in process block 601, which may include powering up the x-ray source. The aforementioned signals generated by the process block 509 of FIG. 5 may then be received on a substantially continuous basis. Since the sorting system may be configured to coordinate the timing (e.g., from the aforementioned time stamp and XRF start and stop timers) generated by the distance measuring device with the timing of the XRF system (utilizing the predetermined speed of the conveyor system) these signals can then be utilized by the XRF system for activation and deactivation of the acquisition of fluoresced signals for classification of each of the metal alloy scrap pieces.

As the XRF system receives the timing signals 509, it will determine whether an XRF start time in the signals is equal to the current time. In other words, the sorting system has determined from the distance measuring device the time in which the previously detected metal alloy scrap piece will be passing within the proximity of the target location along the conveyor system to which the x-ray beam from the x-ray source is directed. The XRF system will continue to wait (by recycling through process block 602) until it has determined that the previously detected metal alloy scrap piece is expected to pass the target location of the x-ray beam. In process block 603, when the XRF start time is equal to the current time, the detected XRF spectrum (e.g., the counts for each channel (corresponding to an element)) of the fluoresced x-rays is recorded by the XRF system, representing the total per-channel energy counts detected by the detector at the moment just before the x-ray beam begins to irradiate the leading edge of the metal alloy scrap piece. This will continue (by recycling through process blocks 602 . . . 604) until the XRF stop time is determined to be equal to the current time. Thus, the per-channel counts are accumulated while the metal alloy scrap piece is being irradiated by the x-ray beam. Once this has occurred, in process block 605, a second (e.g., final) XRF spectrum is recorded, representing the final total per-channel counts for the metal alloy scrap piece. As with the XRF start time, when the sorting system has determined that the trailing edge of the metal alloy scrap piece is expected to pass by the x-ray beam, the accumulation of detector counts is stopped.

Within embodiments of the present invention, it may be important to only acquire and analyze the XRF spectra of the metal alloy scrap pieces, and not any XRF emitted from the conveyor belt, since such conveyor belts may contain certain percentages of the elements that are important for distinguishing between the compositions of the various metal alloy scraps. Such elements may be present in the belt from when it was manufactured. More particularly, since aluminum alloys have low energy elements, fluorescence from the conveyor belt may prevent the sorting system from distinguishing between certain aluminum alloys. Additionally, in embodiments of the present invention, the per-channel counts acquired for each metal alloy scrap piece are accumulated in the system as total running counts for a plurality of irradiated scrap pieces, and not reset for each scrap piece, in order to save on processing time by the system. As a result, it may be important within certain embodiments of the present invention to only acquire XRF spectra during time periods defined by the aforementioned XRF start and stop times.

In process block 606, the total counts for each channel for the metal alloy scrap piece as determined by the XRF start and stop times is determined (for example, by subtracting the total counts acquired at the XRF start time from the total counts acquired at the XRF stop time), which are then saved to a file (e.g., text file) in process block 607. In process block 608, the XRF system then sends this saved data file to the sorting system for analysis and classification of the metal alloy scrap piece.

Alternatively, the system and process 600 may be utilized in order to calibrate the system, including to input data pertaining to standard reference materials and their classifications, which are then used to identify/classify unknown scrap pieces.

Figure 7:
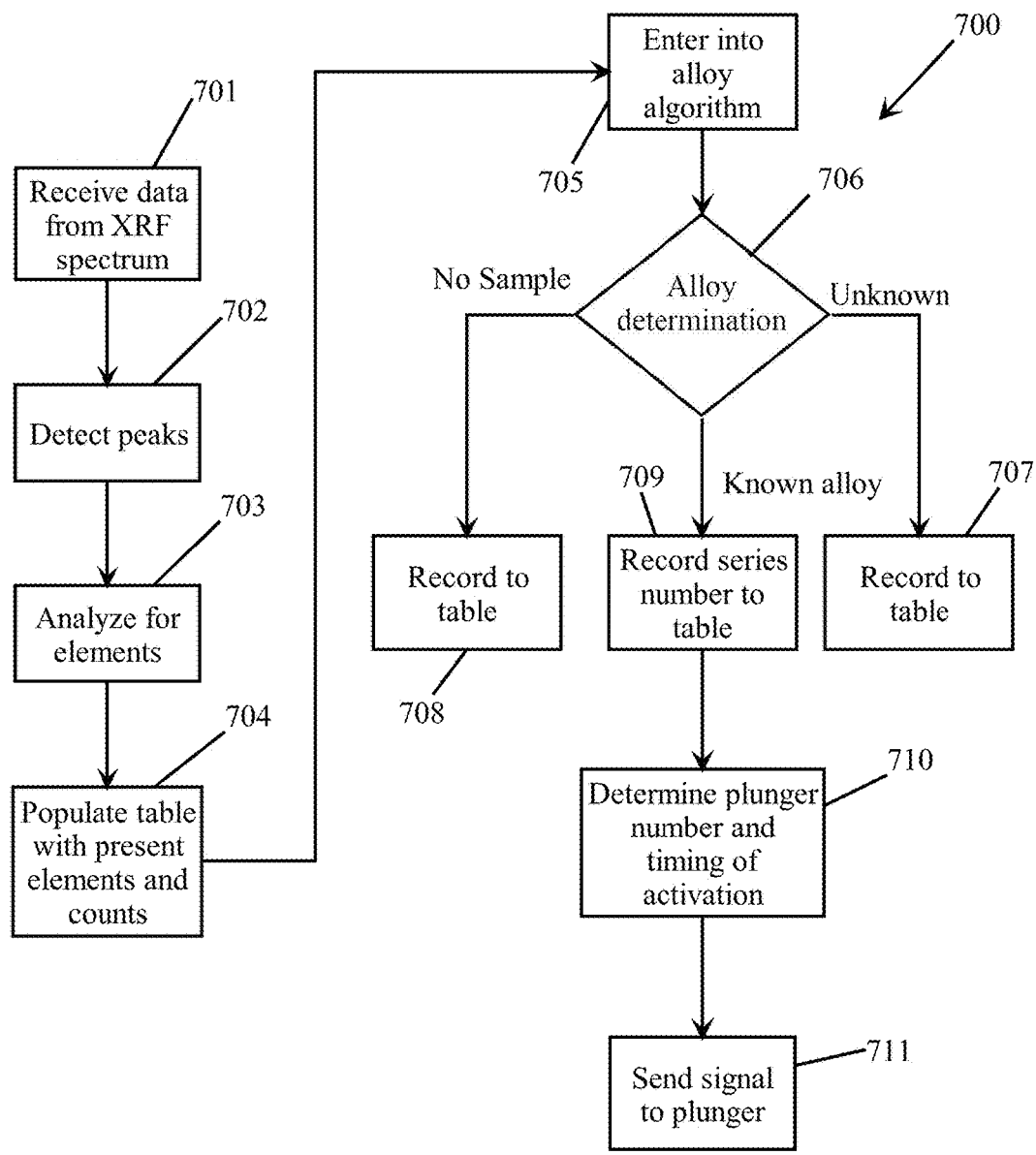
FIG. 7 illustrates a flowchart diagram of a system and method for classifying materials in accordance with embodiments of the present invention.

Referring next to FIG. 7, there is illustrated a system and process 700 for classification of the metal alloy scrap pieces as a function of the detected XRF spectrum resulting from the system and process 600 previously described with respect to FIG. 6. The system and process 700 may be implemented with respect to any of the sorting system embodiments described herein. In process block 701, the XRF spectrum data (representing the accumulated total counts for each channel pertaining to the irradiated metal alloy scrap piece) is received (e.g., from process block 608). In process block 702, the peaks (e.g., the per-channel counts) of the spectrum are detected, and then in process block 703, they are analyzed for associating with their various elements detected within the metal alloy scrap piece. In process block 704, the aforementioned table entry corresponding to the metal alloy scrap piece may be populated with the determined elements and their respective counts, which is then entered in process block 705 into an alloy classification algorithm, such as described in further detail herein (e.g., see FIGS. 17-22, 25-29, and 32-33).

In process block 706, the system and process 700 makes a determination whether the composition of the metal alloy scrap piece is known as a result of the implementation of the alloy classification algorithm. If the classification of the metal alloy scrap piece is unknown, or if there is insufficient data to determine that a sample was even detected, these may be recorded into a table (process blocks 707 and 708, respectively). If the metal alloy scrap piece classification has been determined by an alloy classification algorithm, then in process block 709 the classification may be recorded in a table corresponding to the metal alloy scrap piece; the classification may include a particular alloy series number corresponding to the determined classification. In process block 710, a sorting device (e.g., air jet, plunger, paint brush type plunger, etc.) positioned along the singulated stream in which the metal alloy scrap piece is travelling, and associated with the determined alloy classification, is identified along with the time period during which the metal alloy scrap piece will pass by this sorting device. In process block 711, signals pertaining to the identified time period are sent to the particular sorting device (or to a device controlling the sorting device, (e.g., see the automation control system 108 of FIG. 1)).

Referring next to FIG. 8, there is illustrated a system and process 800 for activation of each one of the sorting devices for ejecting a classified metal alloy scrap piece into a sorting bin. Such a system and process 800 may be implemented within the automation control system 108 previously described with respect to FIG. 1, or within an overall computer system (e.g., the computer system 107) controlling the sorting system. In process block 801, the aforementioned signal generated in process block 711 of FIG. 7 is received. In process block 802, a determination is made whether the timing associated with this signal is equal to the current time. As with the previously described timing for activation and deactivation of the XRF system for each of the metal alloy scrap pieces passing along the conveyor system, the system and process 800 determines whether the timing associated with the classified metal alloy scrap piece corresponds to the expected time in which the classified metal alloy scrap piece is passing within the proximity of the particular sorting device (e.g., air jet, pneumatic plunger, paint brush type plunger, etc.) associated with the classification pertaining to the classified metal alloy scrap piece. If the timing signals do not correspond, a determination is made in process block 803 whether the signal is greater than the current time. If yes, the system may return an error signal. In such an instance, the system may not be able to eject the piece into the appropriate bin. Once the system and process 800 determines that a classified metal alloy scrap piece is passing within the vicinity of a sorting device associated with that classification, it will activate that sorting device in process block 805 in order to eject the classified metal alloy scrap piece into the sorting bin associated with that classification. This may be performed by activating a pneumatic plunger, paint brush type plunger, air jet, etc. In process block 806, the selected sorting device is then deactivated.

Referring to FIGS. 9-13, embodiments of the present invention may be configured to utilize a novel in-line x-ray fluorescence ("IL-XRF") system, such as for the XRF system 120 of FIG. 1 and the XRF system 320 of FIG. 3. Such an IL-XRF system utilizes a novel linear x-ray tube 900, which may be configured with N (N≥1) separate x-ray sources, wherein the linear x-ray tube 900 is configured so that each of the N x-ray sources separately irradiates metal alloy scrap pieces travelling along one or more of the singulated streams. For example, referring to FIGS. 3 and 9, if the linear x-ray tube 900 was utilized in the XRF system 320, it could be configured and positioned over the conveyor belt 380 so that the x-ray source 910 would irradiate metal alloy scrap pieces travelling in the left-most singulated stream initiated by the plunger 351, the x-ray source 911 would irradiate metal alloy scrap pieces travelling in the second from the left-most singulated stream initiated by the plunger 352, the x-ray source 912 would irradiate metal alloy scrap pieces travelling in the third from the left-most singulated stream initiated by the plunger 353, and the x-ray source 913 would irradiate metal alloy scrap pieces travelling in the right-most stream initiated by the plunger 354. Though the linear x-ray tube 900 is described herein having four x-ray sources, such a linear x-ray tube may be configured with any number N (N≥1) of such x-ray sources.

Furthermore, the linear x-ray tube 900 may be configured so that any of its separate x-ray sources irradiates metal alloy scrap pieces travelling in multiple parallel streams. Note that a linear x-ray tube similar to the linear x-ray tube 900, but having any other number N of in-line arranged x-ray sources may be utilized in any sorting system as described herein, or any other sorting system known in the art, or yet to be developed. Such an IL-XRF system provides a linear x-ray tube having multiple sources instead of one each operable at a relatively low power, which significantly reduces the cost and power requirements versus having to utilize multiple separately powered x-ray sources for sorting multiple streams of materials.

Referring to FIGS. 9-12, a linear x-ray tube 900 includes an anode assembly 960, N cathode materials 990, and a grid assembly 939, positioned inside of a vacuum package 901.

The anode assembly 960 may be composed of a conductive (e.g., copper) bar mechanically attached to a high voltage feed-through 921. This bar may substantially span a length of the x-ray tube 901. Alternatively, the anode assembly 960 may be a plurality (e.g., N) of separate conductive bars connected in series. Several different coatings may be added to the copper bar 960, including, molybdenum, tungsten, silver, or any metal. This metal or combinations of metals can then be brazed onto the copper bar 960 in order to provide a layer that will generate the desired x-ray spectrum. Different metals will generate different output spectra from the x-ray tube. In addition to brazing, these metals may be mechanically attached to the bar 960. The bar 960 may also be composed of any metal other than copper. The high voltage feed-through 921 transfers a high voltage from the external environment (e.g., see the x-ray power supply 122 of FIG. 1) of the x-ray tube to the inside of the x-ray tube 100. The anode 960 and all the materials it comes into contact may be held at this high voltage (e.g., 0-50 kV).

Figure 9:
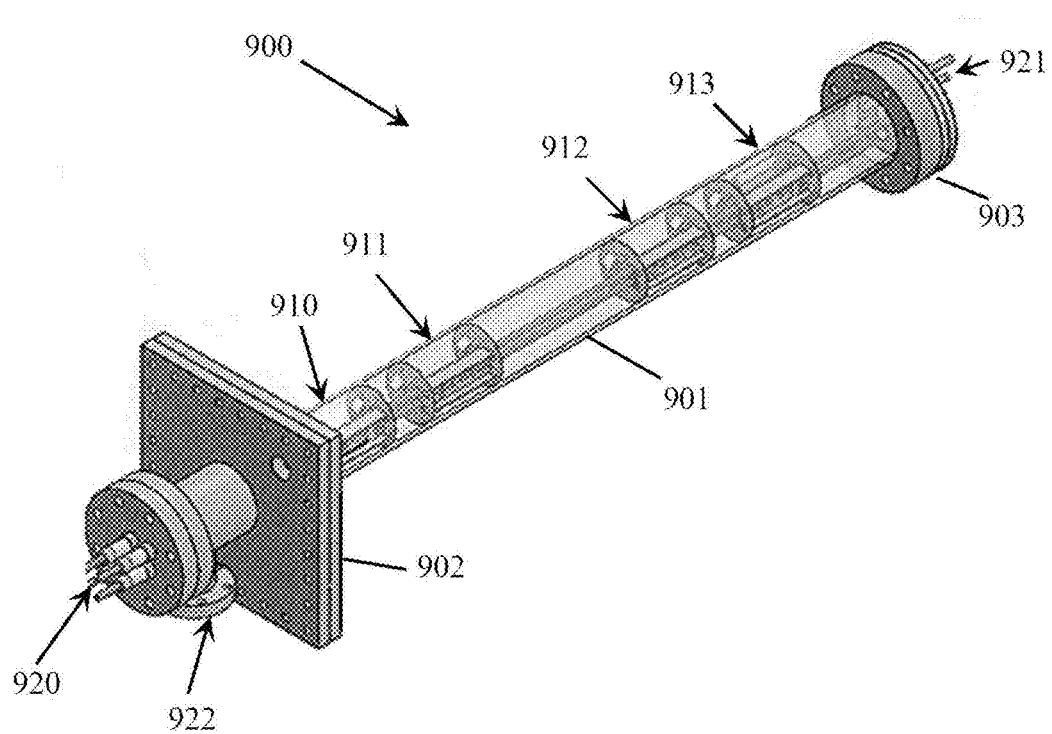
FIGS. 9-13 illustrate an exemplary in-line x-ray fluorescence ("IL-XRF") source configured in accordance with embodiments of the present invention.
Figure 10:
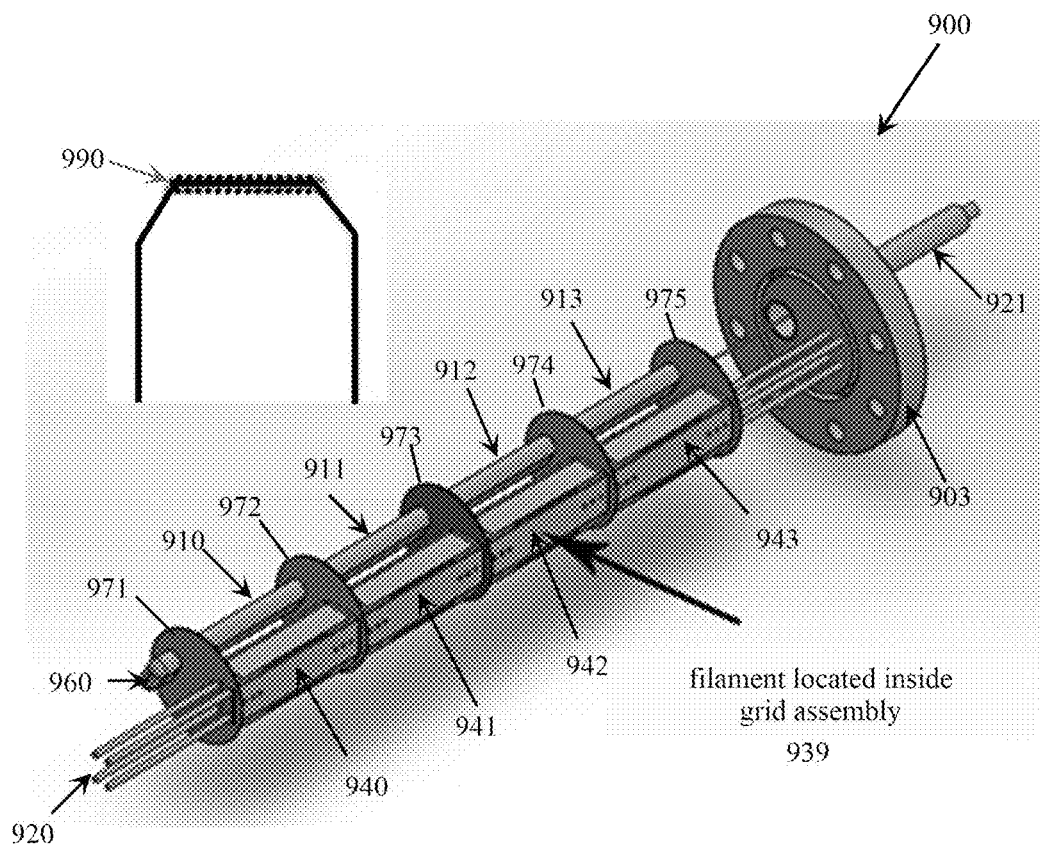

A purpose of the cathode material 990 (see inset) is to emit electrons. The cathode material 990 may be made of tungsten, but may also be thoriated tungsten, an oxide cathode, a cold cathode, or any electron emitter. The tungsten filaments may be wound into a spiral shape in order to increase the electron emission density for the volume of the spiral section of the filament shape. The two ends of the filament 990 may be held at a DC voltage, e.g., 0-15 volts with respect to ground. Application of the DC voltage causes the filaments 990 to heat to a very high temperature. When the temperature is sufficiently high, electrons are released (e-beam) from the filaments 990. A single cathode 990 produces an electron beam (e-beam) that is then focused onto a section of the anode assembly 960. The linear x-ray tube 900 may utilize an array of N (N≥1) cathodes 990 linearly arranged in order to produce multiple electron beams (e-beams), which impact the anode 960 in different sections along the length of the anode assembly 960. The cathodes may be connected to one or more feed-throughs 920 that transfer a voltage from outside the x-ray tube 900 to the filaments 990 inside the x-ray tube 900. As illustrated in FIGS. 9-10, a linear x-ray tube 900 having N x-ray sources may separately control activation and deactivation of each of the N x-ray sources by connecting each of the N cathode filaments 990 to a separate feed-through 920.

Figure 11:
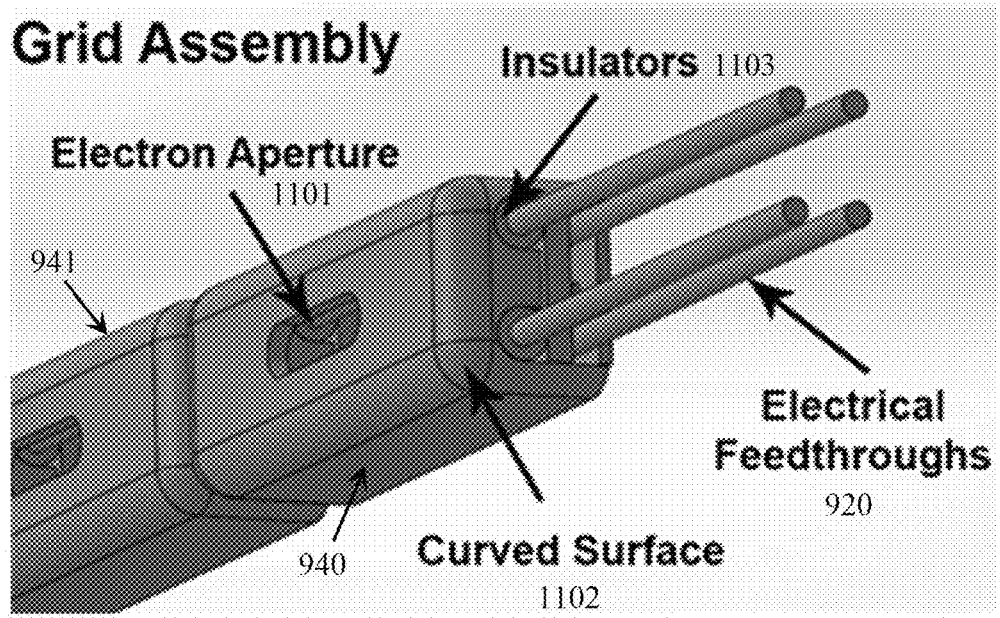
Figure 12:
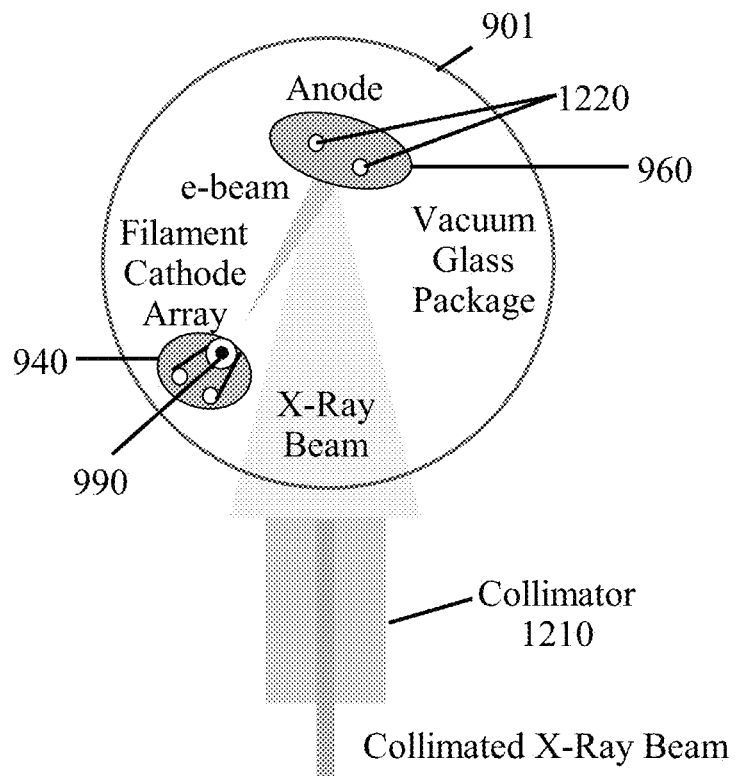

Each grid 940 . . . 943 within the grid assembly 939 may be a conductive (e.g., copper) block, which functions to isolate each of the N electron beams (e-beams) along specific paths inside the x-ray tube 900. Without the grid, electrons might scatter all around inside the x-ray tube 900 causing arcing and/or premature failure of the x-ray tube 900. The electrons that are not emitted along the intended path towards the anode 960 are collected into the grid assembly where there are electrically removed through the grid circuit. Referring to FIGS. 10-12, each of the grids 940 . . . 943 may be configured to hold a voltage used to control the flow of electrons through an aperture 1101 in the grid. Changing the voltage from a negative value to a relatively more positive value will focus the e-beam to a desired shape as the e-beam travels to the anode 960. Each grid may also be shaped to have curved surfaces, which function to generate a uniform electric field distribution in order to mitigate high voltage stress, thus helping to prevent arcs and premature failure of the x-ray tube 900. Each grid may also have a multitude of feed-throughs to allow conductive rods (e.g., copper) of differing voltages to pass through the grid assembly 939. Insulators (e.g., made of a ceramic) may be clamped to each grid to insulate these copper rods. The entire grid assembly 939 may be demountable, allowing the change of a filament 990 when it needs to be replaced.

Insulators (e.g., made of a ceramic) 971 . . . 975 may be used as high-voltage standoffs. These standoffs 971 . . . 975 may be spaced in between the grids 940 . . . 943 and in between the anode assembly 960 and cathode assembly 939. The insulators 971 . . . 975 may be utilized to mechanically hold the anode assembly 960 in place, and also serve to separate the high voltage from the low voltages. These insulators 971 . . . 975 may also have special cutouts (not shown) to increase the rate of vacuum conduction within the tube package.

A demountable vacuum package configured for implementing a linear x-ray source may include a glass tube 901, O-rings, flanges 902, 903, a gated vacuum valve 922, a turbo pump (not shown), and a rough pump (not shown). The rough pump and turbo pump pull a vacuum on the tube to a high vacuum. The long glass tube 901 holds the x-ray components. The vacuum package 901 may be demountable (e.g., by removing one of the flanges 902, 903) to allow x-ray tube components to be replaced (e.g., when they have reached their end of life). The flanges and O-rings may be used to create a reusable vacuum seal.

The linear x-ray tube 900 may include an integrated cooling system (e.g., water) (not shown). For example, water may be passed through a feed-through 1220 into the vacuum package 901 and into a cavity within the anode 960. There may be also a water feed-through (not shown) for water cooling into the grid assembly to cool the cathodes.

As shown in FIG. 12, the linear x-ray tube 901 may further include a collimator 1210 associated with each of the x-ray sources. The collimator 1210 may have an aperture that is aimed at a detection area where a particular metal alloy scrap piece is to be irradiated. As used herein, a "collimator" is a device having an aperture that limits the transmission of x-rays of an x-ray beam such that the x-rays move in the same, or nearly the same, direction. Within embodiments of the present invention, such collimators may be made from a series of closely spaced parallel metal plates utilized to direct the x-ray beam. These direct and incidental x-rays are referred to herein as background noise. Background noise may include x-rays fluoresced or reflected from objects other than the metal alloy scrap pieces, including any interior surfaces of an x-ray device chamber, the conveyor belt, or any other objects within the vicinity of the XRF system. Such background noise may be caused by the irradiating x-rays and fluoresced x-rays impacting other objects in proximity to the detector(s) and causing secondary fluorescence. Within embodiments of the present invention, the choice of resolution of an XRF spectrum may be a function of the resolution desired and the resolution capability of the one or more x-ray detectors. X-ray optics (not shown) may be used to focus a divergent primary x-ray beam into a convergent beam. X-ray optics may take the forms of crystals, capillaries, plastics, metals, or glass. The effect of the optics may reduce the amount of power needed by the x-ray tube and also increase the count rate of the spectrum as seen by the detector. Overall, this can reduce the analysis time for the XRF measurement.

Figure 13:
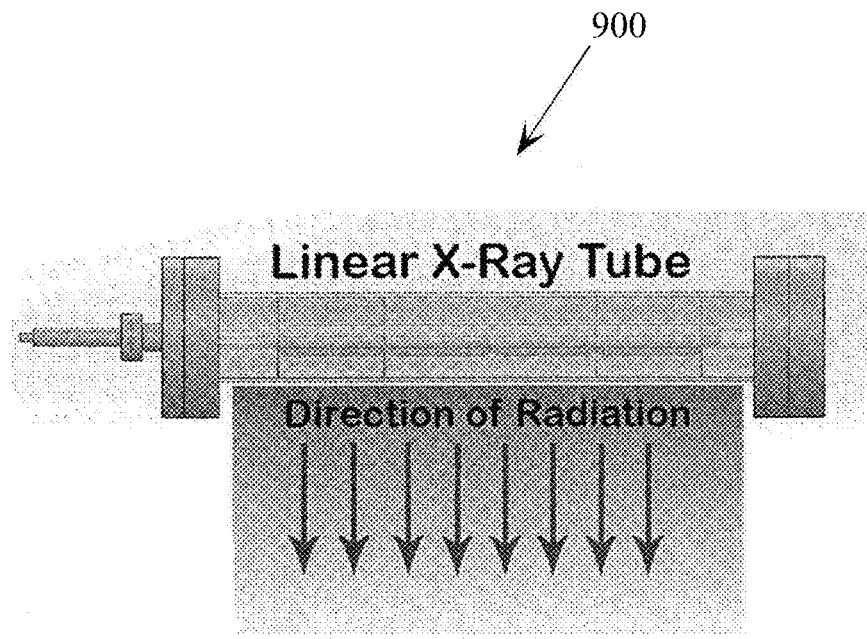
Figure 14:
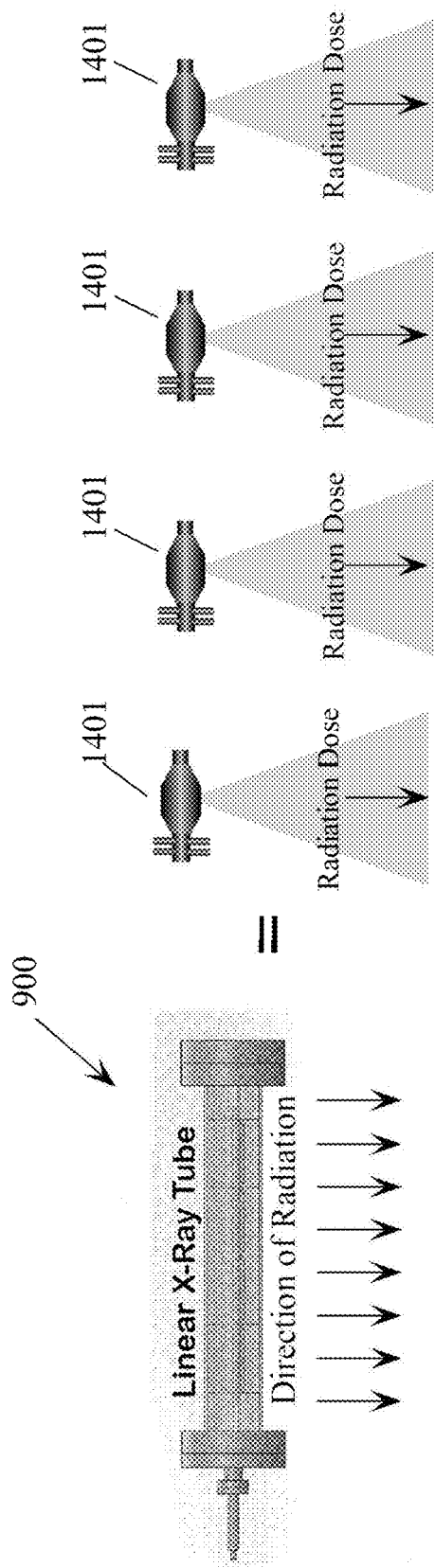
FIGS. 14-15 illustrate a comparison of an IL-XRF source to a prior art XRF source.
Figure 15:
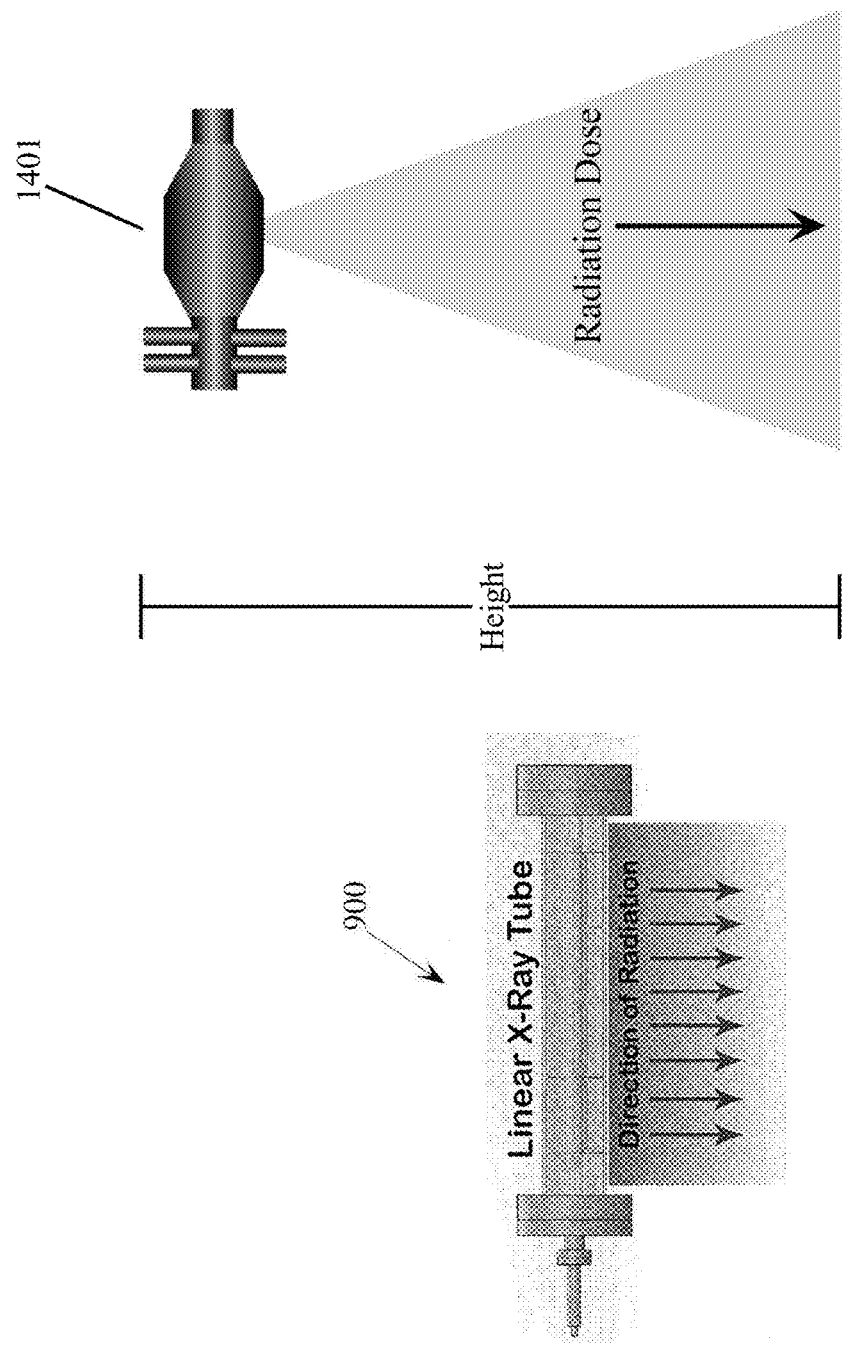

As depicted in FIGS. 13-14, the linear x-ray tube 900 delivers a linear radiation flux outside of the tube 901, which can then be utilized to irradiate along a line generally transverse to the travelling direction of the conveyor system. Conventional x-ray sources 1401 have one spot on their anode that coincides with the electron beam size. As depicted in FIGS. 14-15, the linear x-ray tube 900 is distinguished from a traditional x-ray source 1401 by having the ability to generate radiation in a linear and not a conical fashion. The generation of x-ray flux is dependent on this electron beam spot size. The linear x-ray tube 900 in accordance with aspects of the present disclosure has N electron beam spots arranged in a linear array, and therefore produces a directed x-ray flux with a linear component.

A standard x-ray source 1401 only delivers conical radiation and cannot deliver linear radiation. The cost of one linear x-ray tube 900 is much less than the cost of an equivalent number of standard x-ray sources 1401, which would be needed to deliver the equivalent linear radiation of the linear x-ray tube 900 (as depicted in FIG. 14). For example, compared to one linear x-ray tube 900 with ten cathodes in one linear array, it would take ten standard x-ray sources 1401 to generate an equivalent radiation dose. The cost of ten standard x-ray sources is at least ten times the cost of one linear x-ray tube 900.

The attenuation rate of x-rays is proportional to the inverse square of the distance between the x-ray source and the sample. In other words, radiation intensity decreases exponentially as it travels through air. In order for a standard x-ray source 1401 with a conical x-ray beam to cover a large area of radiation, the power level must be very high. As depicted in FIG. 15, a linear x-ray device 900 configured in accordance with aspects of the present disclosure, because it can be positioned closer to the sample, does not suffer from as much air attenuation as does a standard x-ray source 1401. In order for a standard x-ray source 1401 to cover the same radiation level as a linear x-ray tube 900, it would have to generate an exponentially larger amount of power. Note that in embodiments of the present invention, except for a vacuum created within the immediate vicinity of the x-ray tube 900, the emitted x-rays travel through ambient air towards the metal alloy scrap pieces.

Current x-ray sources 1401 use a tungsten anode and typically operate at 160 kV and 6 kW of power. They require this exponentially larger power because they cannot be positioned close to the sample and still maintain a sufficiently large surface area of coverage (see FIG. 15). When a linear x-ray tube 900 configured in accordance with aspects of the present disclosure is placed closer to the sample, it can thus operate at a lower power (e.g, 15 kV and 15 watts) because there is less attenuation of the radiation through the air.

Standard x-ray sources 1401 with a conical beam shape whose radiation covers a large area operate at 160 kV in order to minimize the attenuation of the primary radiation beam through air. The primary radiation strikes the sample and scatters back into the detector. The scattered radiation entering the detector ranges from 0-160 kV and fills the detector with so many counts that the detector saturates. The detector when saturated is unable to accurately detect smaller numbers of photons (such as within aluminum alloys). When the detector is saturated, the characteristic fluorescence photons that are generated from the sample are not counted by the detector. Therefore, if the primary beam is operated at 160 kV, the detector will not be able to collect the characteristic fluorescence from the sample in a satisfactory manner in order to classify the material.

In order to view a characteristic radiation for lighter elements such as those within aluminum alloys (which are generally all less than 10 kV), an x-ray tube voltage much lower than 160 kV should be used. The inventors have determined that a voltage of approximately 12 kV-15 kV can be used for exciting an aluminum alloy piece and subsequently measuring the characteristic fluorescent photons at the detector in order to successfully classify the aluminum alloys.

As noted, x-ray radiation attenuates in air. Moreover, x-ray radiation attenuates in air as a function of its energy level. Therefore, a photon with an energy of 1 keV will absorb in air in less than 0.25 inches. A photon with an energy of 20 keV will travel several feet before it absorbs into air. The x-ray fluorescence from various metal alloys (e.g., aluminum alloys) cover a range from approximately 1.4 kV-10 keV. This means that the lower energy photons will attenuate at a faster rate than the higher energy photons. For example, if a metal alloy (e.g., aluminum alloy) has magnesium and zinc, it will fluoresce magnesium photons with an energy of 1.25 keV and zinc photons at 8.6 keV. If the fluorescence detector is positioned about 0.1 inches away from the sample (e.g., a metal alloy scrap piece), both of the magnesium and zinc photons will be detected. However, if the detector is positioned further away (e.g., about 2 inches) from the sample, the magnesium photons will not be detected, because they will have been absorbed into the intervening air. Only the zinc photons will be detected. If the detector is positioned about 0.2 inches away from the detector, however, the same metal alloy would produce the same fluorescence, but the detector would measure less magnesium and the same amount of zinc.

Within alternative aspects of the present disclosure, in order to account for the attenuation of photons in air, the detector (e.g., the detectors 124, or the entire x-ray system 120 of FIG. 1) may be automatically moved relative (i.e., closer and farther) to the sample, with the distance between the sample and the detector measured and retrieved. Based on the distance between the sample and detector, aspects of the present disclosure (which may be implemented within a computer-operated process) would calculate the attenuation for each energy for each type of alloy. A process would then determine the original XRF spectrum from the sample, minus the attenuation from air. This new XRF spectrum could then be utilized as input into a classification algorithm (e.g., see FIGS. 7 and 22) in order to classify the alloy.

Within the detector electronics (e.g., the detector electronics 125 of FIG. 1), a wavelength dispersive x-ray fluorescence ("WD-XRF") analysis or an energy dispersive x-ray fluorescence ("ED-XRF") analysis may be utilized. WD-XRF can be used to simultaneously determine the elemental concentrations of a sample. WD-XRF detectors use crystals and Bragg diffraction to split the fluorescence radiation from the sample into different paths. The location for each path is determined by the energy of fluorescence. Because the fluorescence is split into a fan beam where each location on the beam corresponds to a unique energy level, low cost detectors can be used to detect this location dependent fluorescence. For example, a linear array of a pulse counter, SiPN, or MPPC detector(s) could be used instead of SDD, SiLi, or Ge detectors. The use of pulse counters or SiPN diodes are less expensive and bring down the overall cost of the detection system.

WD-XRF differs from energy dispersive x-ray fluorescence ("ED-XRF") analysis by the use of the detectors. ED-XRF systems use a single detector operating in an energy dispersive mode. ED detectors, such as the SiLi and SDD, detect all energies of the fluorescent radiation and then electronically separate them all into bins in order to generate the spectrum.

Monochromators, filters, and optics may be used in an XRF system configured in accordance with embodiments of the present invention in order to enhance the signal-to-noise ("SNR") or peak-to-background ("P/B") ratio. The primary beam of radiation that exits the x-ray tube is polychromatic and divergent. The polychromatic nature of the primary x-ray beam includes Bremsstrahlung radiation, which contributes to background of the spectrum, reducing the quality of the spectrum. As this background value is reduced, the P/B ratio increases, allowing a more desirable high quality spectrum to be produced. Also, the divergence of the primary beam causes less primary radiation directed to the target. This is undesirable because the amount of fluorescence generated is proportional to the amount of primary radiation that strikes the target. Increasing the amount of primary radiation to the target increases the fluorescent radiation and increases the peak in the P/B ratio, resulting in a more desirable and higher quality spectrum.

Monochromators may be used to filter the primary beam to a desired energy range, reducing the Bremsstrahlung generated in the x-ray tube. Reducing the Bremsstrahlung will result in reducing the background of the spectrum, producing a larger P/B ratio. Monochromators can take many forms, such as a multilayer mirror, a crystal, or a filter. A filter can be a single element, or a combination of elements, through which the primary beam passes.

Embodiments of the present disclosure are further illustrated by the following examples, which are set forth to illustrate the presently disclosed subject matter and are not to be construed as limiting.

As has been previously explained, x-ray fluorescence ("XRF") is the emission of characteristic "secondary" (or fluorescent) x-rays from a material that has been excited by irradiating it with x-rays or gamma rays. XRF is based on the principal that individual atoms, when excited by an external energy source, emit x-ray photons of a characteristic energy or wavelength. By counting the number of photons of each energy emitted from a sample, the elements present in the sample may be identified and quantitated. The counting of these photons is then performed on an element-by-element basis. As used herein, the term "counts" refers to the number of photons counted for each element, with the number of counts representing the relative quantities by weight of each of the elements within the irradiated material.

With XRF, quantitative analysis is possible as the net peak area for an element in an acquired XRF spectrum is directly proportional to the mass of the sample. For example, for an acquired XRF spectrum from a sample (e.g., a metal alloy scrap piece), if an aluminum peak having an area of 10,000 counts represents 10 grams of aluminum, then a peak of 20,000 counts would represent 20 grams of aluminum, and a peak of 30,000 counts would represent 30 grams of aluminum. This linear methodology can be used to quantitatively determine both the type and quantity of various elements in a sample.

The XRF spectra utilized within the following examples were acquired from the irradiation of actual samples of such aluminum alloys with the indicated aluminum alloy classifications. Samples of such aluminum alloys can be commercially obtained from various aluminum companies such as ALCOA. Such standard materials are sold with a certification sheet that shows the elemental composition in a percentage form. Alternatively, such XRF spectrum of standard reference aluminum alloys can be commercially obtained from such aluminum companies as ALCOA.

Aspects of the present disclosure differ from traditional quantitative methodologies because they do not seek to determine the linear quantitative relationship for determining mass. The qualitative relationship is still present in order to determine the elements that are present in the sample. However, the matrix effect brought on from large bulk masses of samples does not allow for accurate use of linear quantitative methods. The matrix effects are, however, consistent and not a random event. Therefore, all alloys of a particular type will yield nearly identical spectrums as defined by their elemental composition. Aspects of the present disclosure define the spectrum for one alloy as a signature. Each alloy has a unique signature, which is utilized by aspects of the present disclosure for identifying/classifying metal alloys. For example, three different aluminum alloys, such as aluminum alloys 2024, 3003, and 5051, have three unique spectra. But, all alloys for 5051 have nearly identical spectra.

With respect to aluminum alloys, XRF has the ability to measure each element (e.g., any desired combination of Si, Al, Fe, Cu, Mn, Mg, Cr, Ni, An, Ti, Ag, and B) in each of these alloys. XRF is both a qualitative and quantitative form of spectroscopy; therefore, the spectrums generated by XRF directly correlate to the elemental chemical compositions defined by previously noted Aluminum Association. A system can then be calibrated to measure the elemental concentration of an unknown aluminum alloy sample. Once the system calculates the concentration of each element, it can then compare that data to a standard, or reference, set in order to identify/classify the unknown aluminum alloy of the sample.

Figure 24A:
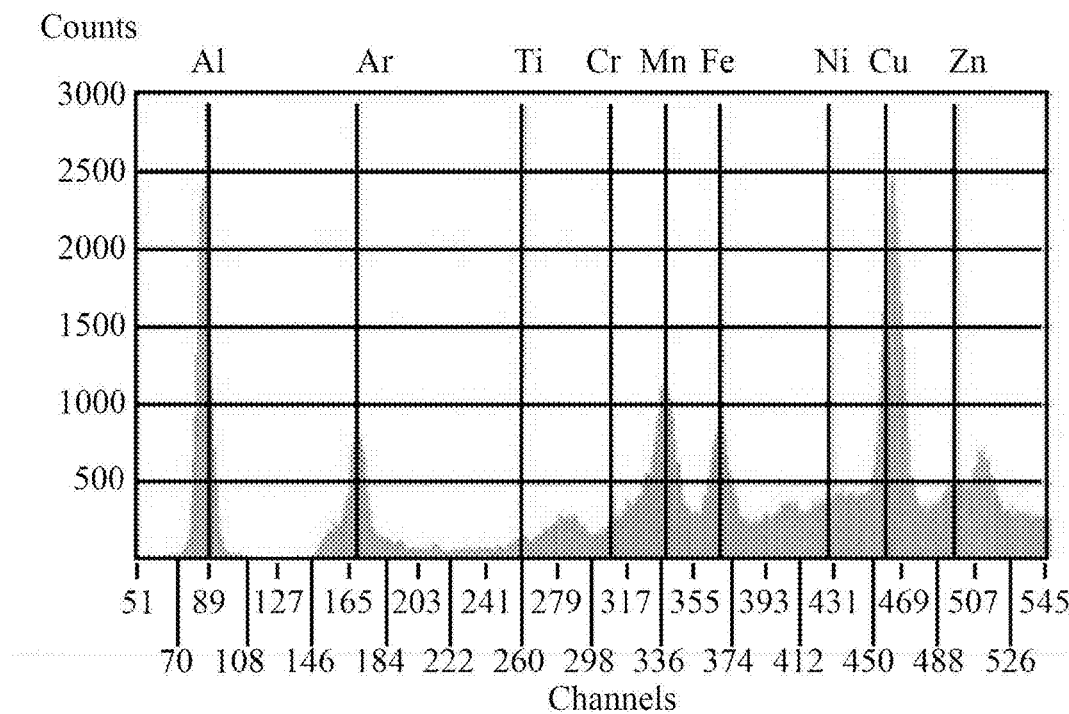
FIGS. 24A-24C show the XRF spectra for the aluminum alloy classifications 6013 (FIG. 24A), 6022 (FIG. 24B), and 6061 (FIG. 24C).
Figure 24B:
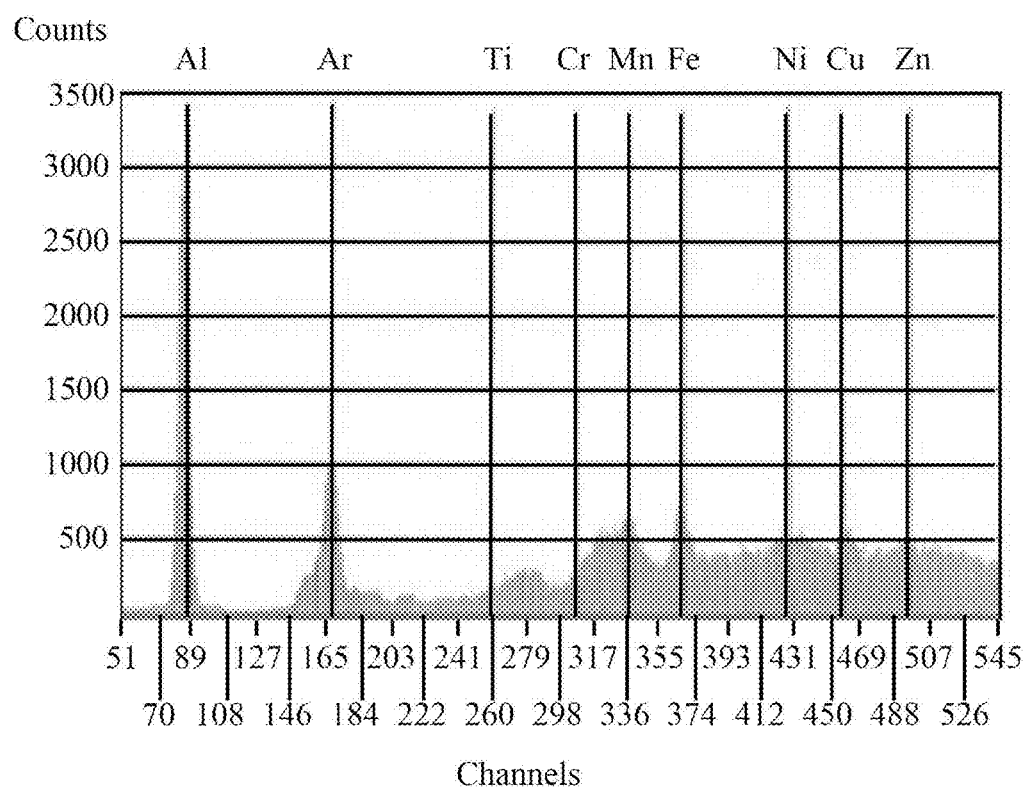
Figure 24C:
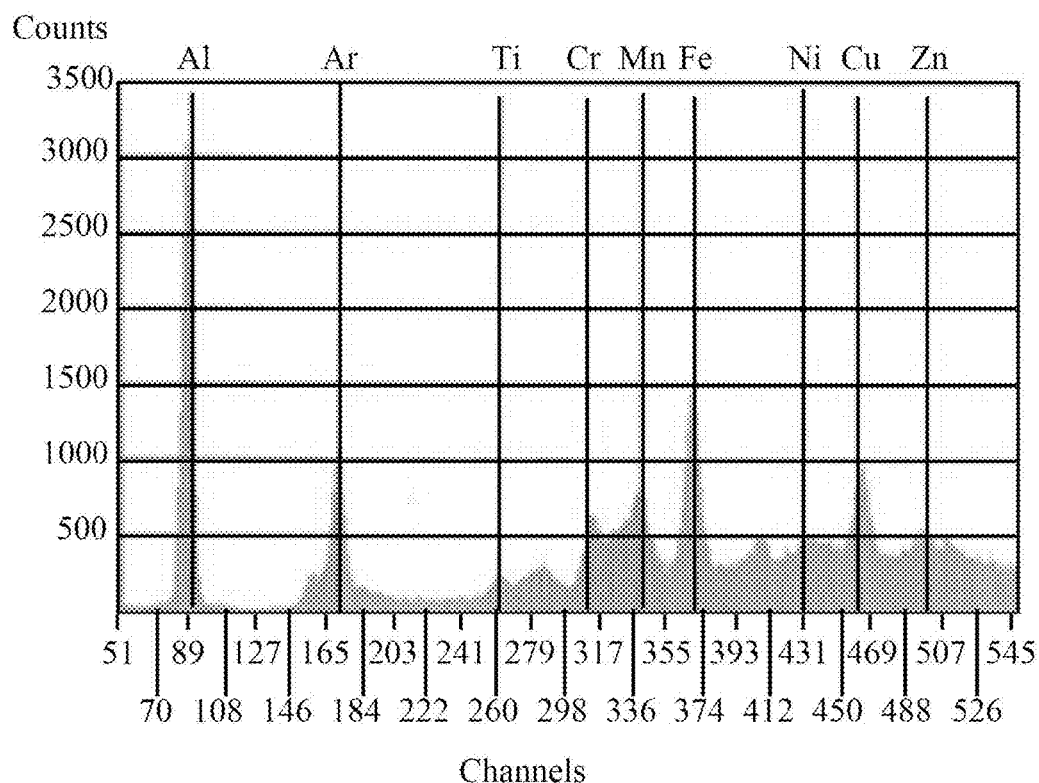

For example, as defined by the Aluminum Association, the published allowable chemical composition limits for aluminum alloy classifications 6013, 6002, and 6061 are shown in FIG. 23. FIGS. 24A-24C show the XRF spectra for the aluminum alloy classifications 6013 (FIG. 24A), 6022 (FIG. 24B), and 6061 (FIG. 24C). The spectrum illustrated in FIG. 24A shows the raw XRF data detected from a sample of an aluminum alloy 6013. The spectrum illustrated in FIG. 24B shows the raw XRF data detected from a sample of an aluminum alloy 6022. The spectrum illustrated in FIG. 24C shows the raw XRF data detected from a sample of an aluminum alloy 6061. These spectrums can be am placed side by side for a quick comparison of their respective spectra. These alloys each contain the alloying elements Si, Fe, Cu, Mn, Mg, Cr, Zn, and Ti; however, the spectrums clearly highlight different peak heights for each of these elements. These peak heights directly correlate to elemental concentrations in the alloy; the larger the peak, the larger the element concentration in the alloy.

Referring to FIG. 23, it can be seen that the iron concentrations for aluminum alloys 6013, 6022, and 6061 are 0.5, 0.05-0.20, and 0.7, respectively. Aluminum alloy 6022 has the least amount of iron, aluminum alloy 6061 has the most amount of iron, and aluminum alloy 6013 is in the middle. The concentrations for each element in the Aluminum Association publication are easily and directly observable by the XRF spectra in FIGS. 24A-24C For example, by looking closely at the spectra in FIGS. 24A-24C, the size of the iron peak directly correlates to those concentration values defined by the Aluminum Association. Just as the Aluminum Association has defined a unique set of data to define each alloy, XRF can be used to measure that unique set of data through spectroscopy.

Referring to the spectrum in FIG. 24A of the aluminum ("Al") alloy 6013, shown are peaks for such alloying elements as Al, Ti, Cr, Mn, Fe, Ni, Cu, and Zn. The channels in which these peaks are positioned within the spectrum correspond to detected XRF energy levels (net counts) for each of these elements. This XRF spectrum contains peaks and a background. The peaks are what contain the valuable information from the spectrum. The net peak area for each channel is a number that equals the peak counts minus the background counts (referred to herein as the "net counts" or the "net peak counts"). The net peak area of one peak therefore conveys quantitative information about the concentration of that alloying element in the sample. The larger the peak, the more of that element is found in the sample; the smaller the peak, the less of that element is found in the sample. Also, the location of the peak contains qualitative information about which element is in the sample. For example, in the spectrum of FIG. 24A, the peak at channel 370 corresponds to an energy level of 6.4 keV; therefore, that peak represents the fluorescence detected from iron in the sample. The XRF spectrum therefore contains qualitative and quantitative information about the sample, which is why it is useful in alloy identification/classification.

Table 1 shows the net peak counts determined from the XRF spectrum of FIG. 24A. One can easily see the correlations between peak size and net peak counts.

TABLE 1

| Al Alloy 6013 | Net Counts |
|---|---|
| Mg | 0 |
| Al | 20960 |
| Si | 0 |
| Ti | 272 |
| Cr | 0 |
| Mn | 5006 |
| Fe | 5998 |
| Cu | 18561 |
| Zn | 28 |

Various techniques and methodologies can be utilized to attempt to identify/classify materials, such as aluminum alloys for implementation into a sorting system, such as those disclosed herein. The following provides an example of the use of a dot product method for classifying materials, which is then compared to identification/classification techniques utilized within embodiments of the present invention.

The dot product has been used extensively in geometry regarding vector analysis. In the definition of the dot product, what is important to note is that the result is a single scalar. In other words, the result is typically an integer or decimal value, such as 27, or 36.53.

The data contained in Table 1, which is a summary of the useful information of an exemplary XRF spectrum of a material, is a one-dimensional array, which can also be referred to as a vector. In this example, Table 1 provides the net counts of aluminum alloy 6013.

Figure 25:
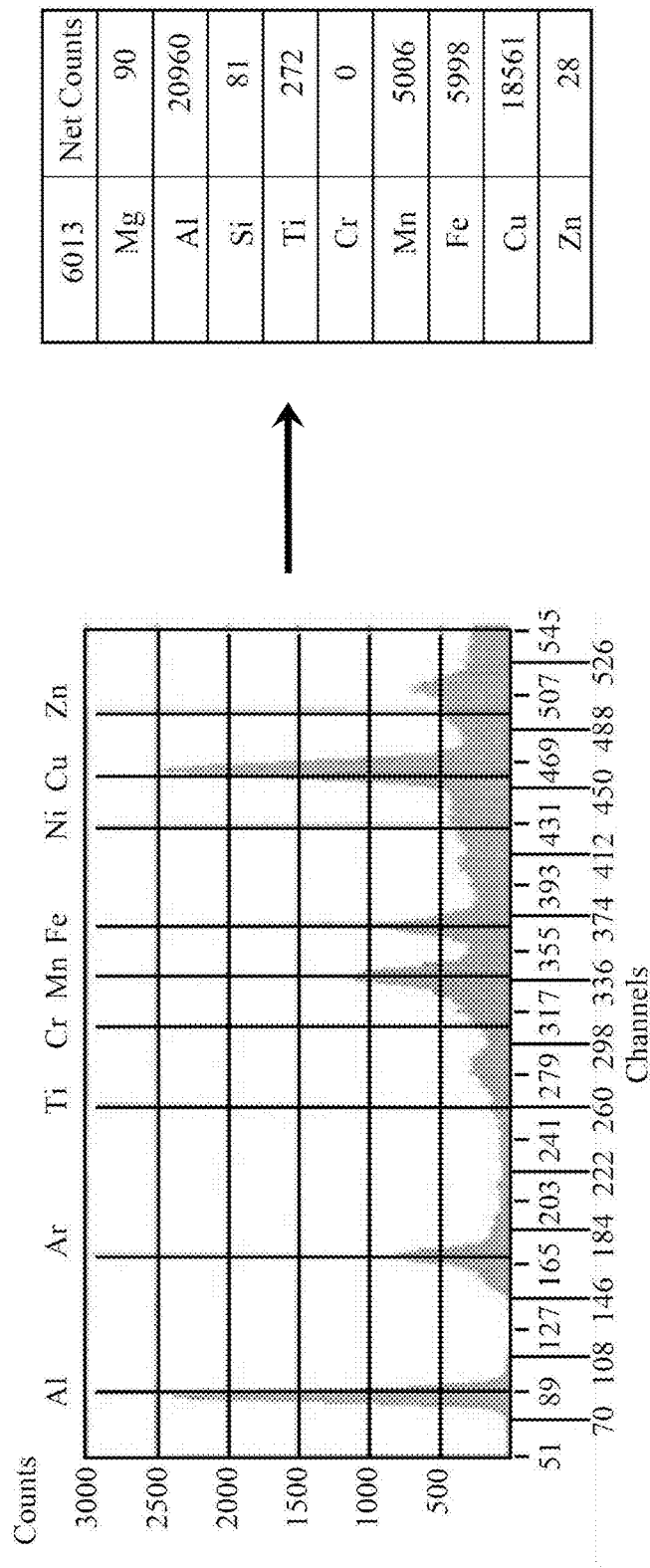
FIG. 25 shows a process for converting a spectrum into a vector of net counts for a material.
Figure 26:
FIG. 26 shows a process for normalizing the vector of FIG. 25.

Referring to FIG. 25, a first step of the dot product method is to place the quantitative data from the XRF spectrum of an unknown material into a one-dimensional array (a vector) of the net peak counts. Referring to FIG. 26, a second step of the dot product method is to normalize that vector (for example, by calculating a ratio of each of the net counts to a square root of the sum of squares of the net counts). A third step of the dot product method is to calculate the dot product of the normalized vector from the unknown material with a standard reference material vector, which has also been normalized. If the dot product result is 1, then the materials are the same. If the dot product is below a threshold value less than but near 1, then the unknown material is a different material than the standard reference material.

TABLE 2

| Normalized Vector of Unknown Material | Normalized Vector of Al Alloy 6013 | Multiplied Components |
|---|---|---|
| 0.003096171 | 0.003096171 | 9.58628E-06 |
| 0.72106393 | 0.72106393 | 0.519933191 |
| 0.002786554 | 0.002786554 | 7.76488E-06 |
| 0.009357318 | 0.009357318 | 8.75594E-05 |
| 0 | 0 | 0 |

TABLE 2-continued

| Normalized Vector of Unknown Material | Normalized Vector of Al Alloy 6013 | Multiplied Components |
|---|---|---|
| 0.172215937 | 0.172215937 | 0.029658329 |
| 0.206342627 | 0.206342627 | 0.04257728 |
| 0.63853376 | 0.63853376 | 0.407725362 |
| 0.000963253 | 0.000963253 | 9.27857E-07 |
|  | Dot Product | 1 |

The dot product is the sum of the multiplied components from each element in the array. As shown in Table 2, in this example, the sum of the multiplied components equals to 1. If this was a material analysis, and the first spectrum was from an unknown sample and the second spectrum was for aluminum alloy 6013, then the conclusion would be that the unknown sample is aluminum alloy 6013.

Referring to Table 3, when the dot product is calculated between aluminum alloys 6013 and 6022, the result is 0.79.

TABLE 3

| Normalized Vector of Al Alloy 6013 | Normalized Vector of Al Alloy 6022 | Multiplied Components |
|---|---|---|
| 0.003096171 | 0.00273983 | 8.48298E-06 |
| 0.72106393 | 0.986658319 | 0.711443725 |
| 0.002786554 | 0.004338064 | 1.20882E-05 |
| 0.009357318 | 0.004155408 | 3.88835E-05 |
| 0 | 0 | 0 |
| 0.172215937 | 0.051874108 | 0.008933548 |
| 0.206342627 | 0.140735916 | 0.029039819 |
| 0.63853376 | 0.060184925 | 0.038430106 |
| 0.000963253 | 0.01849385 | 1.78143E-05 |
|  | Dot Product | 0.79 |

Referring to Table 4, when the dot product is calculated between aluminum alloys 6013 and 6061, the result is 0.81.

TABLE 4

| Normalized Vector of Al Alloy 6013 | Normalized Vector of Al Alloy 6061 | Multiplied Components |
|---|---|---|
| 0.003096171 | 0.003375856 | 1.04522E-05 |
| 0.72106393 | 0.830723021 | 0.599004406 |
| 0.002786554 | 0.00225057 | 6.27134E-06 |
| 0.009357318 | 0.323819562 | 0.003030083 |
| 0 | 0.084546426 | 0 |
| 0.172215937 | 0.091523194 | 0.015761753 |
| 0.206342627 | 0.397638269 | 0.082049725 |
| 0.63853376 | 0.174794296 | 0.111612059 |
| 0.000963253 | 0.0288073 | 2.77487E-05 |
|  | Dot Product | 0.81 |

Therefore, consider an example in which the unknown sample to be identified happens to be aluminum alloy 6013. Using the dot product method, if such an unknown sample was compared to the three reference vectors for aluminum alloys 6013, 6022, and 6061, and if a threshold value of 0.9 was chosen, then one would be able to identify the unknown aluminum alloy as aluminum alloy 6013 and not either of the aluminum alloys 6022 and 6013.

The larger the differences between samples, the better the dot product method is to use in material separation, which is why the dot product method is able to distinguish between significantly different materials such as between brass, stainless steel, and aluminum. This method is problematic, however, when it comes to alloy identification as can be seen from the foregoing example as the dots product for comparing aluminum alloys 6013 and 6022 (i.e., 0.79) and the dots products for comparing aluminum alloys 6013 and 6061 (i.e., 0.81) are very similar in number. That is because highly relevant spectral information is lost in the calculation for the dot product.

For example, consider an exemplary task of trying to identify aluminum alloy 5086 separate from aluminum alloys 5182, 5052, and 5754. The dots products for each of these alloy comparisons are shown in FIGS. 30-31. The net counts for each of these aluminum alloys are shown in FIG. 32. The normalized vectors for each of these aluminum alloys were determined by calculating a ratio of each of the net counts to a square root of the sum of squares of the net counts.

Referring to FIG. 30, when the dot product is calculated between the normalized vectors of aluminum alloys 5086 and 5086, the result is 1. Referring to FIG. 30, when the dot product is calculated between the normalized vectors of aluminum alloys 5086 and 5052, the result is 0.95. Referring to FIG. 31, when the dot product is calculated between the normalized vectors of aluminum alloys 5086 and 5182, the result is 0.996. Referring to FIG. 31, when the dot product is calculated between the normalized vectors of aluminum alloys 5086 and 5454, the result is 0.981.

As can be seen, all of these dot products are very close to each other. These dot products are so close to each other that they are within the error margins of XRF measurements for XRF systems. Therefore, the dot product method cannot be reliably used to distinguish between individual aluminum alloys, especially those within a particular aluminum alloy series. The dot product method fails because this method is based on a singular value of the dot product and does not use the high quality spectral information that is preserved.

In contrast, embodiments of the present invention utilize an elemental composition signature ("ECS") technique, which preserves the spectral information from the spectrum, and then uses the normalized spectral information to compare to normalized standard references. The spectral data is not converted to a vector, and a dot product method is not performed. As a result, the ECS technique accounts for both qualitative and quantitative data, in addition to the errors, in XRF fluorescence measurements.

Within the ECS technique, in accordance with embodiments of the present invention, the raw XRF spectrum data is acquired from an irradiated sample (e.g., a metal alloy scrap piece). Then, the net peak areas are determined for each element in the spectrum. The net peak areas are then normalized in order to generate an ECS for that sample (e.g., by dividing each of the net counts for each element by the sum of all of the net counts). The resulting ECS is a table of numbers used to identify/classify the sample. The ECS quantifies the elemental concentrations for the irradiated sample, which is independent of shape, size, and distance of the sample from the XRF detector. In this fashion, irregular shapes and distances of samples, such as metal alloy scrap pieces, will still yield quantified results that can be used to identify/classify the sample (e.g., the alloy type). For example, with respect to identifying/classifying aluminum alloys, the ECS defines a unique property for each aluminum alloy, which exists independently of the size, shape, and distance of the aluminum alloy. Additionally, the ECS is a direct measurement of the elemental concentrations for each aluminum alloy that are defined by the Aluminum Association, validating the use of the ECS for aluminum alloy identification/classification.

Figure 27:
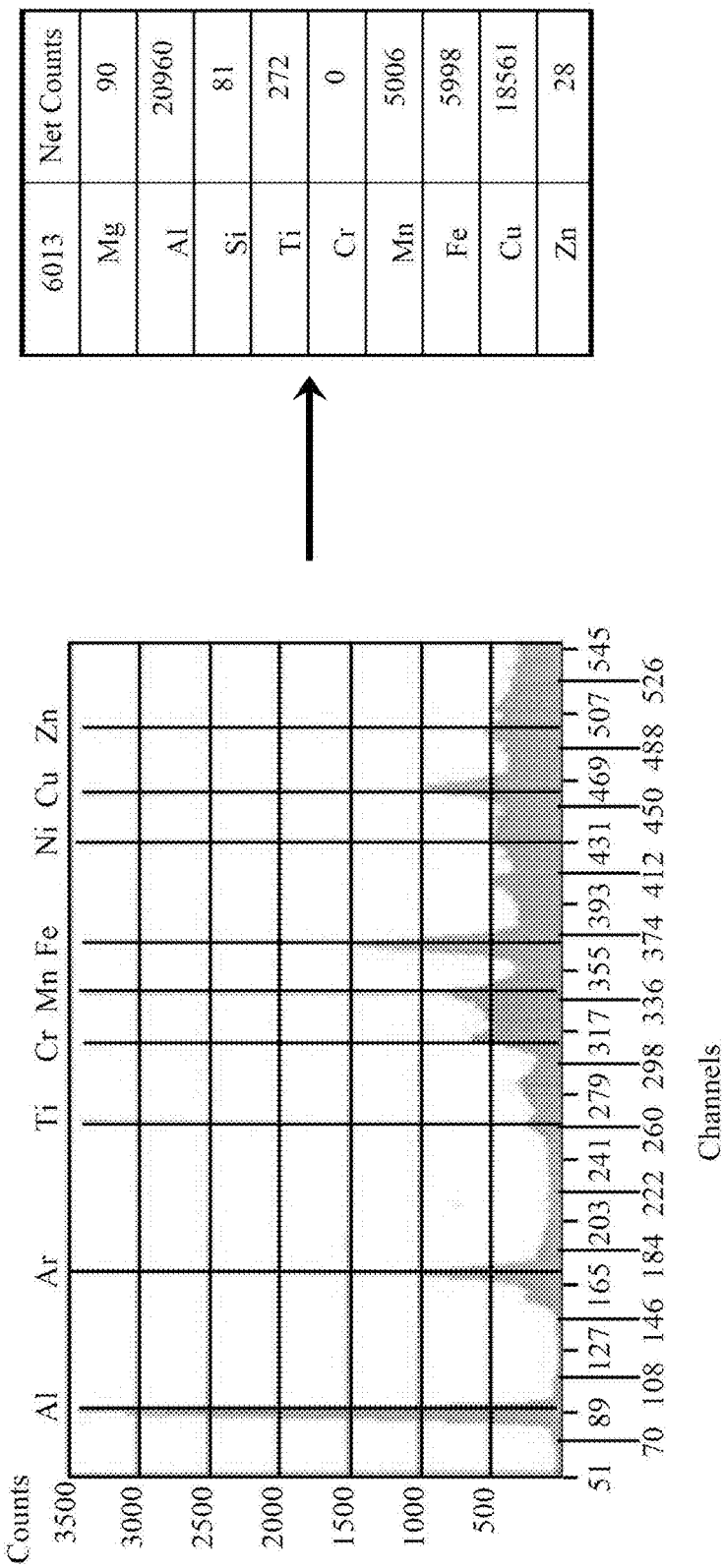
FIG. 27 shows a process for converting a spectrum into a vector of net counts for an exemplary material in accordance with embodiments of the present invention.
Figure 28:
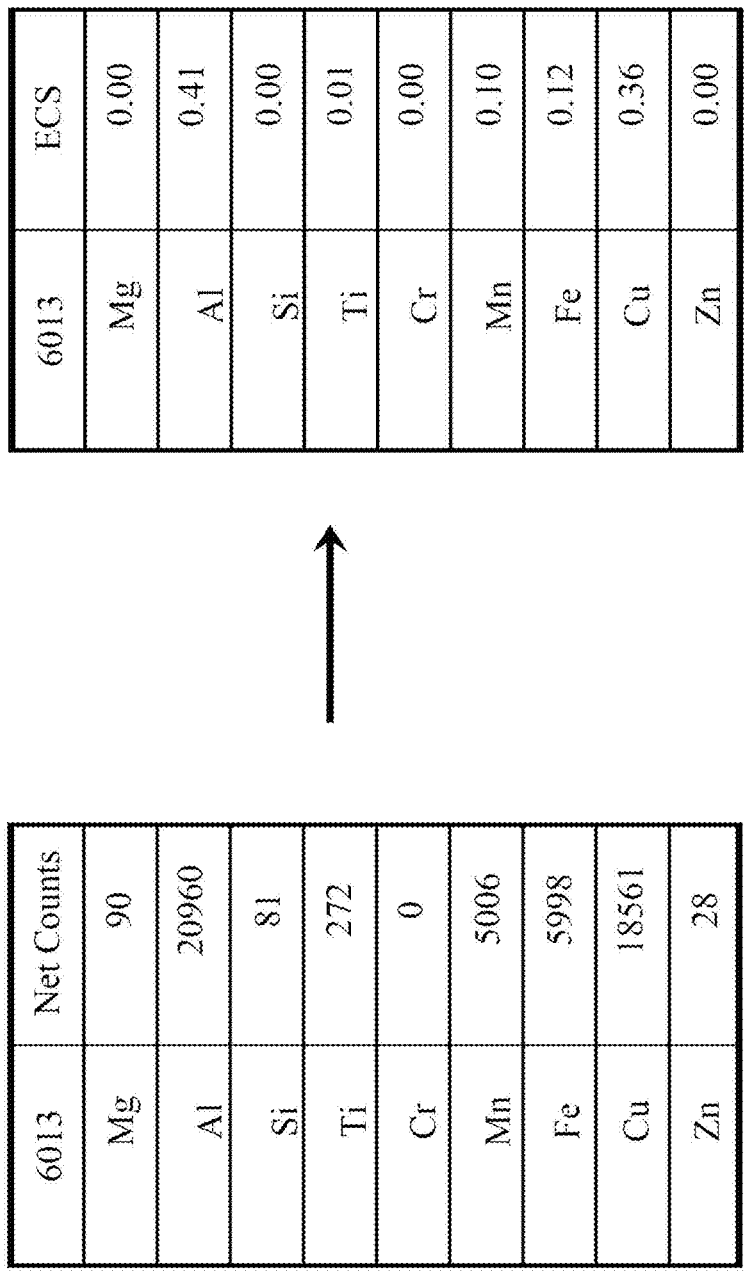
FIG. 28 shows a process for normalizing the vector of FIG. 27 for the exemplary material into an elemental composition signature ("ECS"), in accordance with embodiments of the present invention.

FIGS. 27-29 provide an example of an operation of an alloy identification/classification algorithm utilizing an ECS technique, configured in accordance with embodiments of the present invention. First, the raw XRF spectrum data of an unknown irradiated sample (e.g., metal alloy scrap piece) is acquired utilizing an XRF system, and the net counts determined for each of the elemental channels. These net counts are converted to an ECS for the unknown irradiated sample, which is a one-dimensional array. For purposes of illustration, assume that the unknown irradiated sample is composed of an aluminum alloy 6013. The raw XRF spectrum data and the ECS in this example are shown in FIG. 27. Next, the ECS of the unknown irradiated sample is normalized, as shown in FIG. 28. In this example, the ECS is normalized by dividing each of the net counts for each element by the sum of all of the net counts. However, embodiments of the present invention may normalize the ECS for the unknown samples and the standard references by taking the ratio of the net counts of each element with the net count of aluminum within the unknown sample or the standard reference(s), as the case may be.

Next, referring to FIG. 29, the normalized ECS of the unknown sample (e.g., metal alloy scrap piece) is compared to one or more normalized standard reference ECS's, each pertaining to a standard reference metal alloy, which have built-in ranges for error in XRF measurement. In this example, one of the standard reference ECS's pertains to aluminum alloy 6013, while the other standard reference ECS pertains to aluminum alloy 6022. If the ECS of the unknown sample falls within the ECS ranges of one of the standard reference metal alloys, then the unknown sample can be identified/classified. If the ECS of the unknown sample falls outside of the defined ECS ranges of a particular standard reference metal alloy, then the unknown metal alloy scrap piece is of a different alloy than that particular standard reference metal alloy.

In FIG. 29, the normalized ECS of the unknown sample is on the left and is compared to the normalized standard reference ECS's for the aluminum alloys 6013 and 6022. The comparison clearly shows that the unknown sample is aluminum alloy 6013 and not aluminum alloy 6022 based on their aluminum and copper content. Thus, it is clearly shown that the ECS technique is successful in identifying alloys because it preserves the quantitative and qualitative data.

For comparison of the ECS technique to the dot product method previously discussed with respect to FIGS. 30-31, consider the exact same dataset of XRF spectra for aluminum alloys 5052, 5086, 5182, and 5454. Utilizing these XRF spectra, the following example will utilize the ECS technique for determining alloys. FIG. 32 shows the four aluminum alloys 5052, 5086, 5182, and 5454 and their respective ECS values (e.g., the net counts normalized by determining the ratio of each net count to a sum of all of the net counts for that alloy).

As noted herein, a difference between the ECS technique and dot product method is that instead of using one value to identify the alloys, the ECS technique uses the individual information from all of the alloying elements to determine the alloy, which in this example are Mg, Si, Ti, Cr, Mn, Fe, Cu, and Zn. Based on the datasets in FIG. 32, an identification/classification algorithm, such as described herein with respect to FIGS. 7 and 22, can separate out these alloys which are within the errors of XRF measurement. The error measurements for each of the ECS values for these exemplary aluminum alloys are shown in FIG. 33. The error measurements associated with the various standard reference ECS disclosed herein can be user defined for each of the elements within a particular ECS. Since typical XRF systems have inherent errors in measurement as high as plus or minus 10-15%, with the best XRF systems claiming a plus or minus 5% error, such error measurements may be utilized for determining the error measurements for each of the ECS values utilized within embodiments of the present invention.

As a result of the utilization of the entire XRF spectrum as a dataset by the ECS technique, the differences between the ECS values for these four alloys can be readily seen. For example, the aluminum alloy 5052 is the only alloy with a Cr value of 0.09±0.02, which is much greater than the Cr values of the other three alloys. Additionally, the aluminum alloy 5454 is the only alloy with a Mn value of 0.28±0.02, which is much greater than the other three alloys. And, the aluminum alloy 5086 has a copper value of 0.04±0.01, while the aluminum alloy 5182 has a copper value of 0.00±0.01.

Therefore, an identification/classification sorting algorithm, which may be implemented within any of the embodiments of the present invention, to identify/classify an aluminum alloy of an unknown metal alloy scrap piece based on the aforementioned ECS values for the aluminum alloys 5052, 5086, 5182, and 5454 may be configured to perform the following determinations:

(a) For an unknown metal alloy scrap piece, if its determined ECS value for Cr is between 0.07 and 0.11, then the unknown metal alloy scrap piece can be identified/classified as aluminum alloy 5052;

(b) For an unknown metal alloy scrap piece, if its determined ECS value for Mn is between 0.26 and 0.30, then the unknown metal alloy scrap piece can be identified/classified as aluminum alloy 5454.

(c) For an unknown metal alloy scrap piece, if its determined ECS value for Cr is not between 0.07 and 0.11, and its determined ECS value for Mn is not between 0.26 and 0.30, but its determined ECS value for Cu is between 0.03 and 0.05, then the unknown metal alloy scrap piece can be identified/classified as aluminum alloy 5086, else the unknown metal alloy scrap piece can be identified/classified as aluminum alloy 5182.

Furthermore, the aforementioned normalization techniques for producing the ECS values can be enhanced to add sensitivity and discrimination to the sorting systems and methods disclosed herein.

Referring next to FIGS. 17-22, a system and process, configured in accordance with embodiments of the present invention, is described for classifying materials (e.g., metal alloy scrap pieces, such as aluminum alloys) utilizing x-ray fluorescence. Any of the embodiments of sorting systems (e.g., the sorting system 100 and the sorting system 300) described herein may be configured to utilize the system and process 2200 of FIG. 22 in order to classify materials (e.g., metal alloy scrap pieces) for sorting into separate bins based on the classification(s) determined by the system and process 2200. Additionally, materials sorting systems other than those described herein, including those well known in the art and those yet to be developed, may be configured to utilize the system and process 2200 of FIG. 22 in order to classify materials for sorting into separate bins based on the classification(s) determined by the system and process 2200. The system and process 2200 may be utilized within the process block 405 of FIG. 4 and/or the process block 706 of FIG. 7.

The system and process 2200 is configured to determine net peak areas for providing the net counts utilized to produce the ECS values for unknown samples (e.g., irradiated metal alloy scrap pieces as described herein) and the ECS values for standard reference materials (e.g., standard reference aluminum alloys, including those corresponding to the classifications published by the Aluminum Association).

Figure 17:
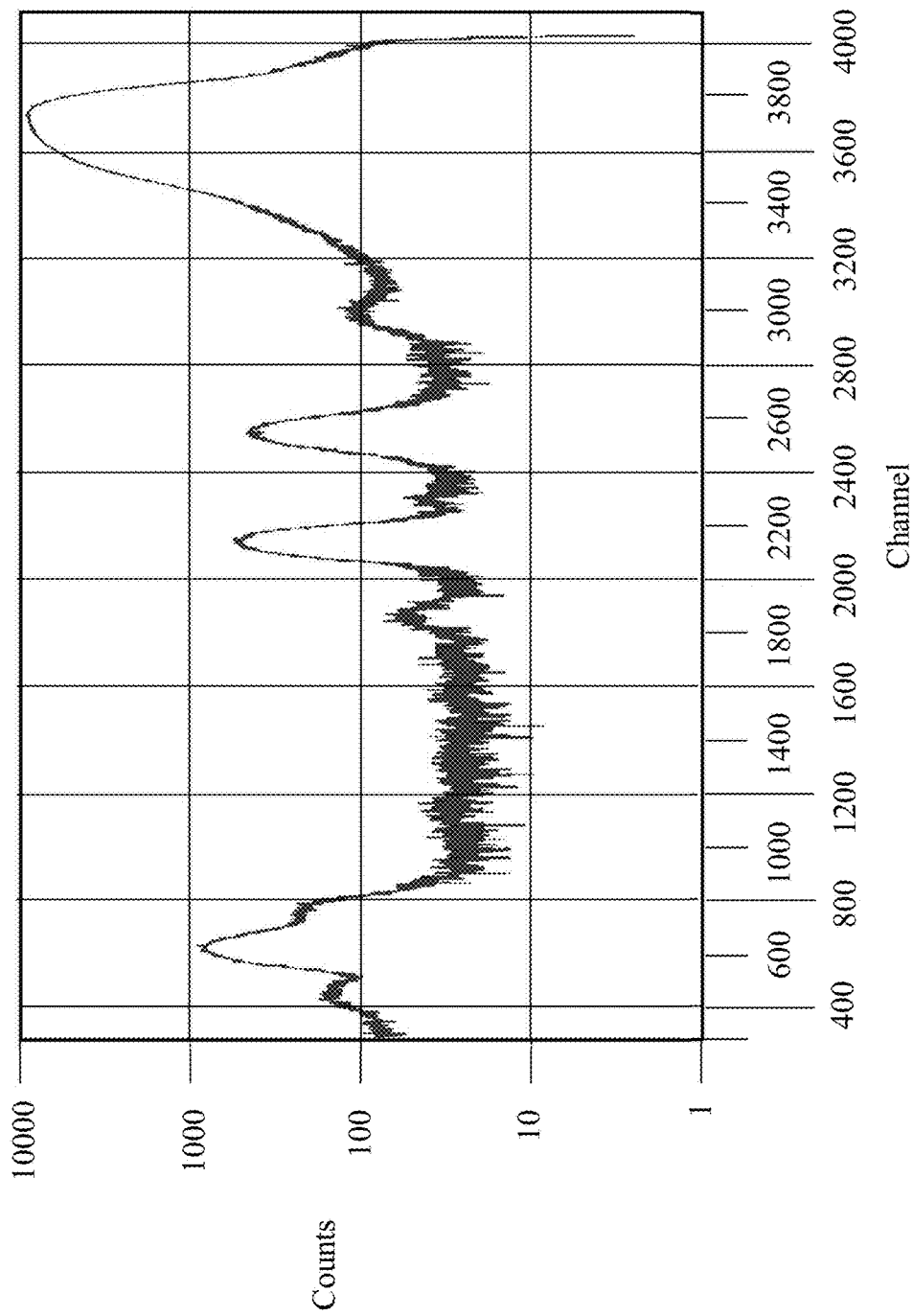
FIGS. 17-21 illustrate an example of a system and process for classifying materials as a function of their x-ray fluorescence.
Figure 18:
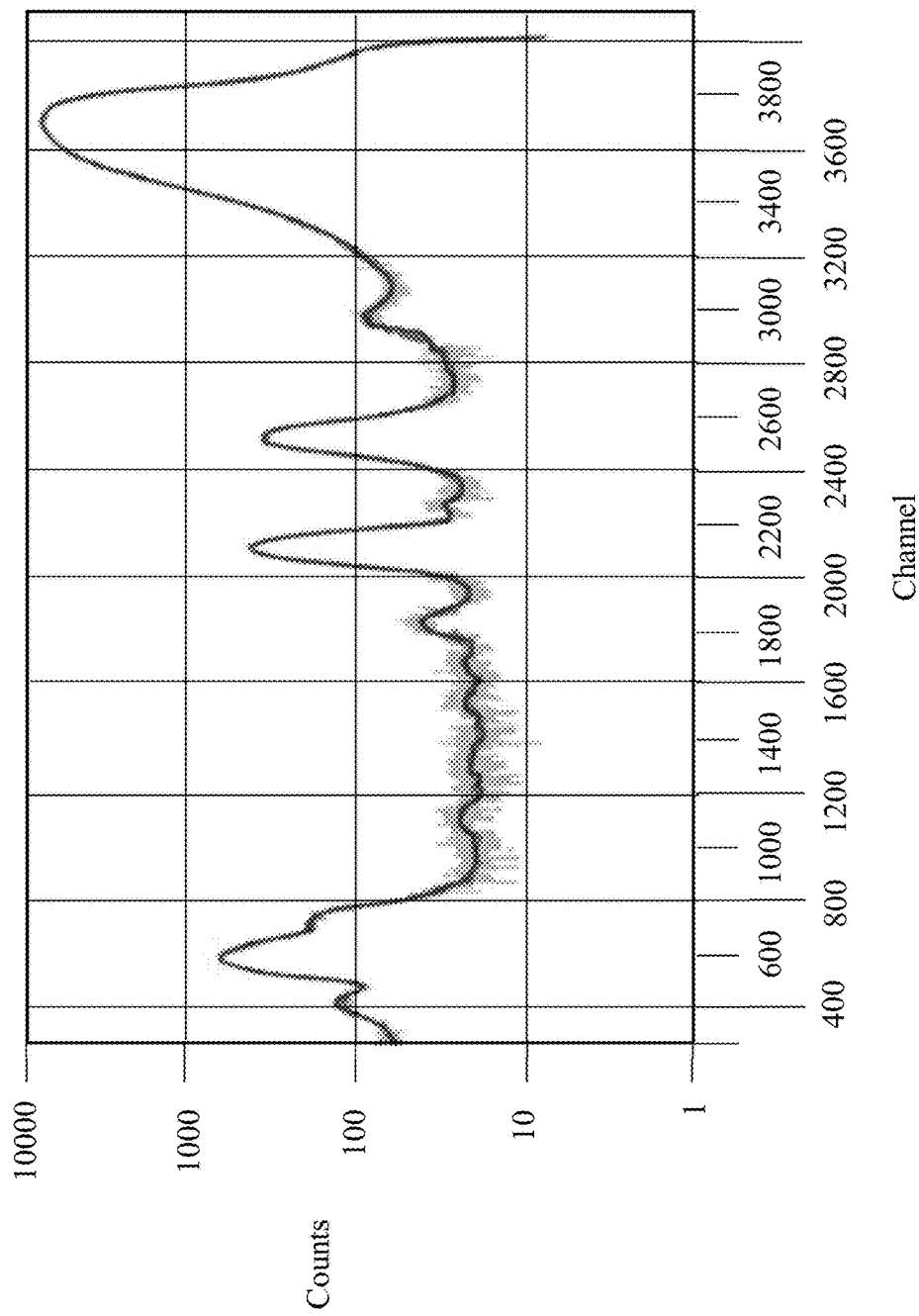
Figure 19:
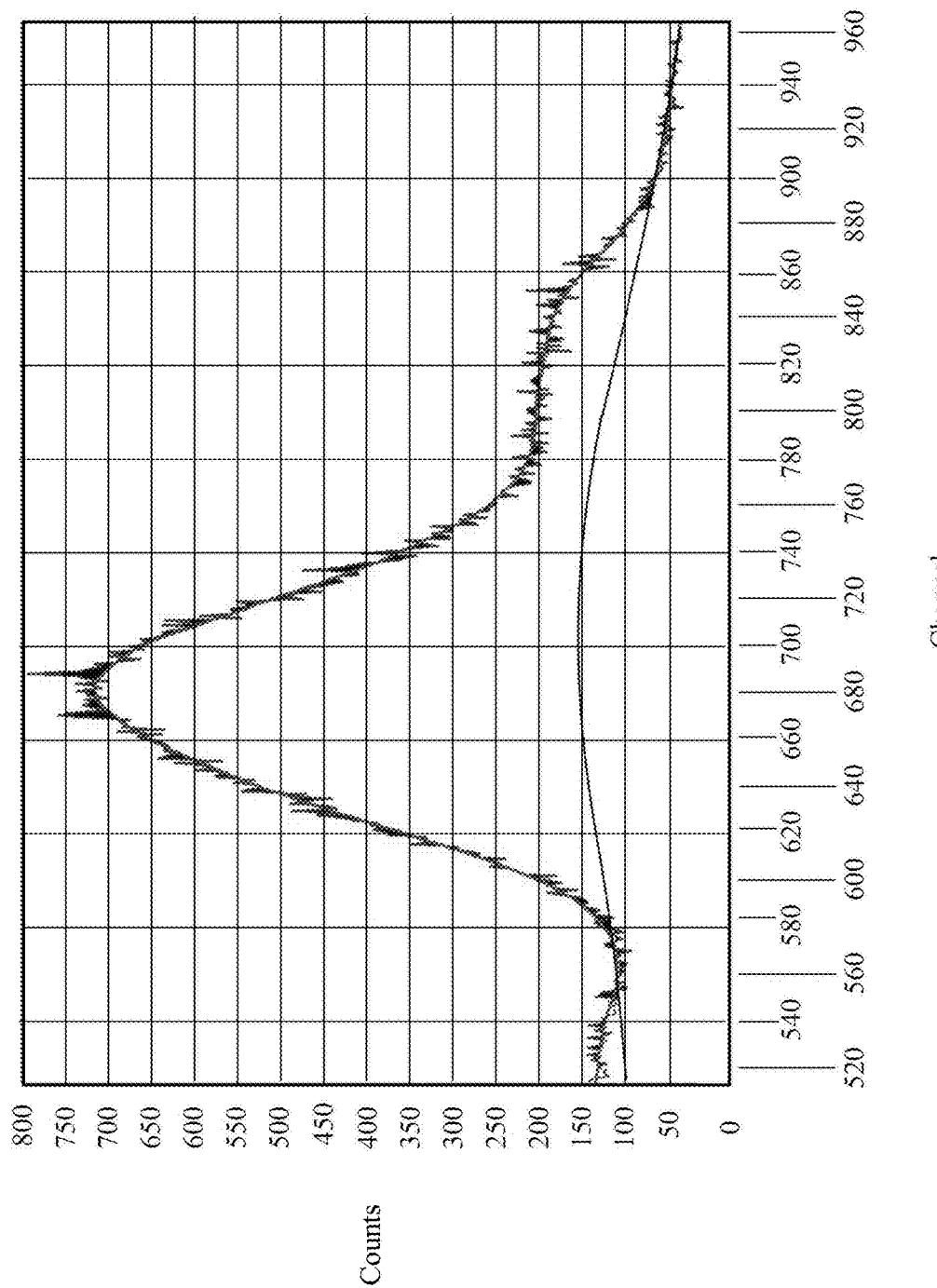
Figure 20:
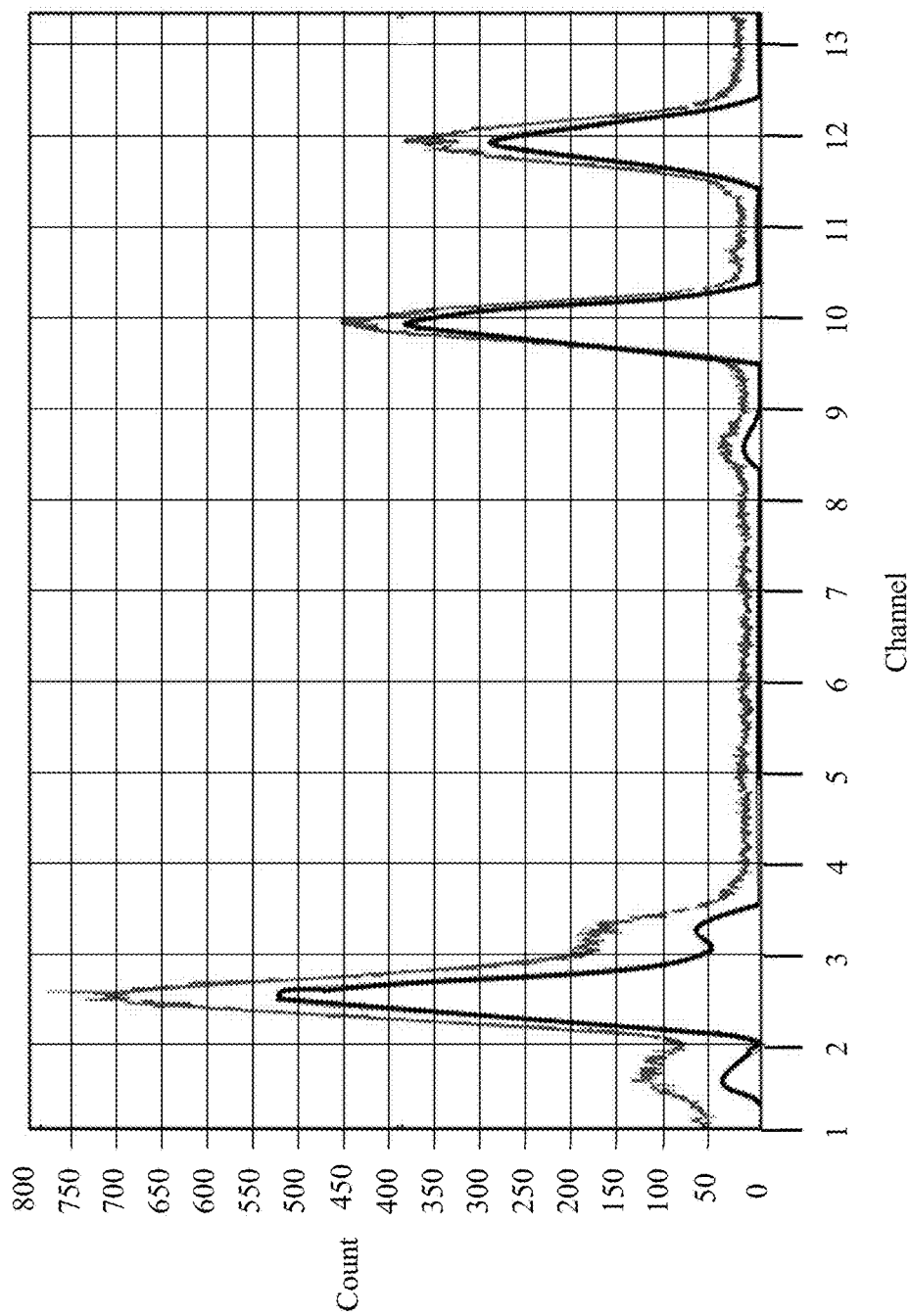
Figure 21:
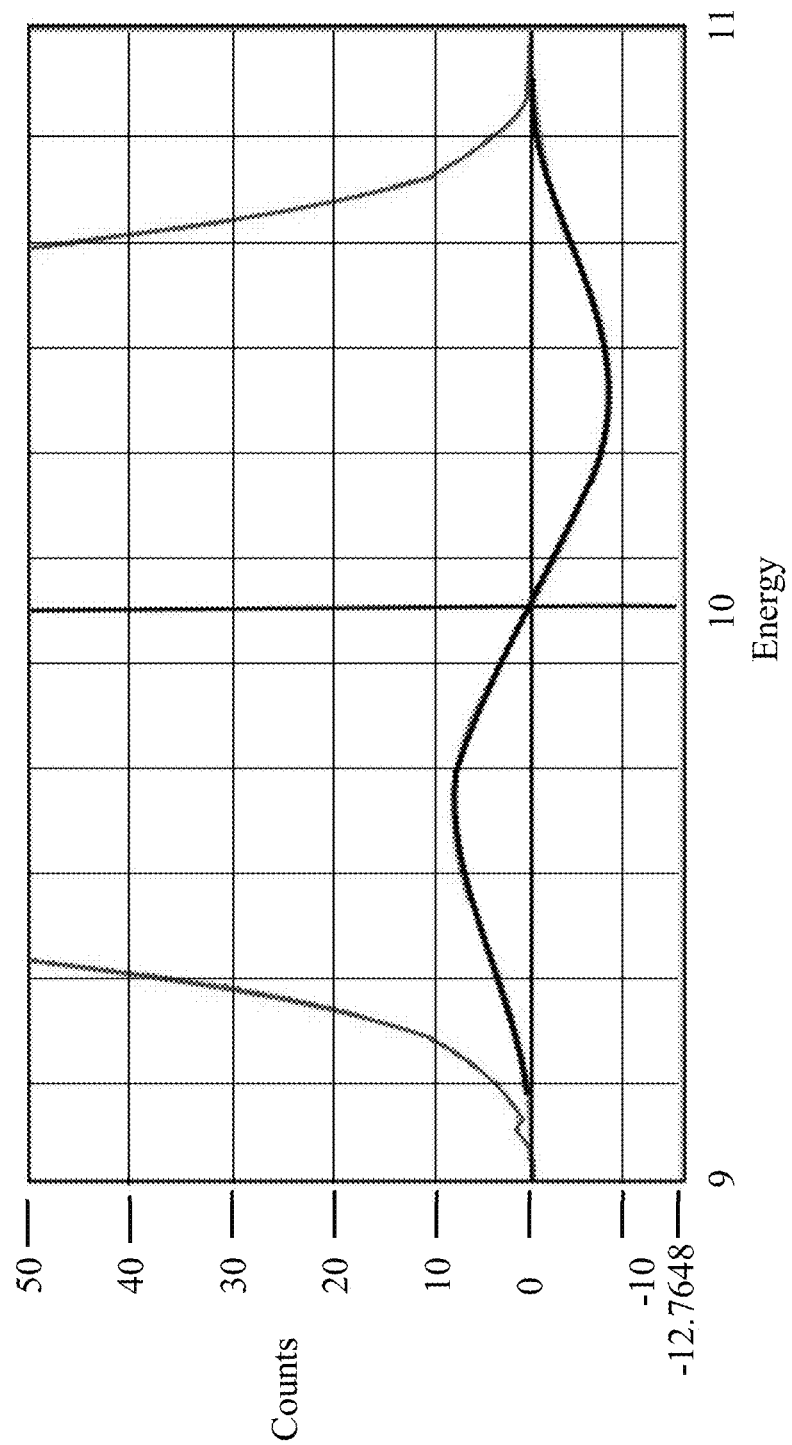

In process block 2201, the raw XRF spectrum data pertaining to an irradiated material (e.g., a metal alloy scrap piece) is received from the XRF detector(s). FIG. 17 illustrates an exemplary graph of such an XRF spectrum. In process block 2202, the square root of the raw XRF spectrum data may be produced to decrease the processing time needed for further calculations (e.g., the following process blocks). In process block 2203, a smoothing filter, such as a Savistsky-Golay filter or a least squares method, is applied to the data from the process block 2202. Referring to FIG. 18, such a smoothing filter plots a smooth curve of the raw XRF spectrum data (or the square root of the raw XRF spectrum data produced in the process block 2202). In FIG. 18, the raw XRF spectrum data is labeled as 1801, while the smoothed spectrum is labeled as 1802. In process block 2204, the peaks are stripped away by using mathematical formulas of moving averages in order to estimate the background counts. Referring to FIG. 19, a portion of the total XRF spectrum is represented to show the original XRF spectrum labeled as 1901, the smoothed spectrum labeled as 1902, and the estimated background labeled as 1903. In process block 2205, the estimated background is then subtracted from the smoothed spectrum in order to generate a spectrum that only includes the net peak areas. In FIG. 20, the raw spectrum data is labeled as 2001, while the final spectrum showing the produced net peak areas is labeled as 2002. In process block 2206, these final spectrum counts may then be squared to correspond to their original values (since the original data may have had their square roots calculated in process block 2202). In process block 2207, the derivative of this spectrum is taken in order to locate and determine the peak centers and edges for determining the peak widths in order to accurately determine the net peak area counts. In FIG. 21, the first derivative is labeled as 2101. The net peak area counts are then calculated based on the peak widths, such as described with respect to FIG. 27. In process block 2208, the normalized counts for each element are then used to determine the ECS values for the material, such as described with respect to FIG. 28. In process block 2209, the ECS values are then compared to the ECS values for one or more standard reference materials, such as described with respect to FIGS. 29 and 33. In process block 2210, the material is then identified/classified based on the results of the comparison(s) of the ECS's.

As has been described herein, embodiments of the present invention may be implemented to perform the various functions described for identifying, tracking, classifying, and sorting materials, such as metal alloy scrap pieces. Such functionalities may be implemented within hardware and/or software, such as within one or more data processing systems (e.g., the data processing system 3400 of FIG. 34), such as the previously noted computer system 107 and/or automation control system 108. Nevertheless, the functionalities described herein are not to be limited for implementation into any particular hardware/software platform. As will be appreciated by one skilled in the art, aspects of the present invention may be embodied as a system, method, and/or program product. Accordingly, aspects of the present invention may take the form of an entirely hardware embodiment, an entirely software embodiment (including firmware, resident software, micro-code, etc.), or embodiments combining software and hardware aspects that may all generally be referred to herein as a "circuit," "circuitry," "module," or "system." Furthermore, aspects of the present invention may take the form of a program product embodied in one or more computer readable storage medium(s) having computer readable program code embodied thereon. (However, any combination of one or more computer readable medium(s) may be utilized. The computer readable medium may be a computer readable signal medium or a computer readable storage medium.)

A computer readable storage medium may be, for example, but not limited to, an electronic, magnetic, optical, electromagnetic, infrared, biologic, atomic, or semiconductor system, apparatus, controller, or device, or any suitable combination of the foregoing, wherein the computer readable storage medium is not a transitory signal per se. More specific examples (a non-exhaustive list) of the computer readable storage medium may include the following: an electrical connection having one or more wires, a portable computer diskette, a hard disk, a random access memory ("RAM") (e.g., RAM 3420 of FIG. 34), a read-only memory ("ROM") (e.g., ROM 3435 of FIG. 34), an erasable programmable read-only memory ("EPROM" or flash memory), an optical fiber, a portable compact disc read-only memory ("CD-ROM"), an optical storage device, a magnetic storage device (e.g., hard drive 3431 of FIG. 34), or any suitable combination of the foregoing. In the context of this document, a computer readable storage medium may be any tangible medium that can contain or store a program for use by or in connection with an instruction execution system, apparatus, controller, or device. Program code embodied on a computer readable signal medium may be transmitted using any appropriate medium, including but not limited to wireless, wire line, optical fiber cable, RF, etc., or any suitable combination of the foregoing.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, controller, or device.

The flowchart and block diagrams in the figures illustrate architecture, functionality, and operation of possible implementations of systems, methods, processes, and program products according to various embodiments of the present invention. In this regard, each block in the flowcharts or block diagrams may represent a module, segment, or portion of code, which includes one or more executable program instructions for implementing the specified logical function(s). It should also be noted that, in some implementations, the functions noted in the blocks may occur out of the order noted in the figures. For example, two blocks shown in succession may, in fact, be executed substantially concurrently, or the blocks may sometimes be executed in the reverse order, depending upon the functionality involved.

Furthermore, the classification system and process of the present disclosure may also include a neural network whereby the system and process is capable of learning the identification/classifications of materials for then grouping unknown materials scanned by an XRF system into predefined groups.

Modules implemented in software for execution by various types of processors may, for instance, include one or more physical or logical blocks of computer instructions which may, for instance, be organized as an object, procedure, or function. Nevertheless, the executables of an identified module need not be physically located together, but may include disparate instructions stored in different locations which, when joined logically together, include the module and achieve the stated purpose for the module. Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices. The data may provide electronic signals on a system or network.

These program instructions may be provided to a processor and/or controller of a general purpose computer, special purpose computer, or other programmable data processing apparatus (e.g., controller) to produce a machine, such that the instructions, which execute via the processor of the computer or other programmable data processing apparatus, create means for implementing the functions/acts specified in the flowchart and/or block diagram block or blocks.

It will also be noted that each block of the block diagrams and/or flowchart illustrations, and combinations of blocks in the block diagrams and/or flowchart illustrations, can be implemented by special purpose hardware-based systems that perform the specified functions or acts, or combinations of special purpose hardware and computer instructions. For example, a module may be implemented as a hardware circuit including custom VLSI circuits or gate arrays, off-the-shelf semiconductors such as logic chips, transistors, controllers, or other discrete components. A module may also be implemented in programmable hardware devices such as field programmable gate arrays, programmable array logic, programmable logic devices, or the like.

Computer program code, i.e., instructions, for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network ("LAN") or a wide area network ("WAN"), or the connection may be made to an external computer (for example, through the Internet using an Internet Service Provider).

These program instructions may also be stored in a computer readable storage medium that can direct a computer, other programmable data processing apparatus, controller, or other devices to function in a particular manner, such that the instructions stored in the computer readable medium produce an article of manufacture including instructions which implement the function/act specified in the flowchart and/or block diagram block or blocks.

The program instructions may also be loaded onto a computer, other programmable data processing apparatus, controller, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

One or more databases may be included in a host for storing and providing access to data for the various implementations. One skilled in the art will also appreciate that, for security reasons, any databases, systems, or components of the present invention may include any combination of databases or components at a single location or at multiple locations, wherein each database or system may include any of various suitable security features, such as firewalls, access codes, encryption, de-encryption and the like. The database may be any type of database, such as relational, hierarchical, object-oriented, and/or the like. Common database products that may be used to implement the databases include DB2 by IBM, any of the database products available from Oracle Corporation, Microsoft Access by Microsoft Corporation, or any other database product. The database may be organized in any suitable manner, including as data tables or lookup tables.

Association of certain data (e.g., for each of the metal alloy scrap pieces processed by a sorting system described herein) may be accomplished through any data association technique known and practiced in the art. For example, the association may be accomplished either manually or automatically. Automatic association techniques may include, for example, a database search, a database merge, GREP, AGREP, SQL, and/or the like. The association step may be accomplished by a database merge function, for example, using a key field in each of the manufacturer and retailer data tables. A key field partitions the database according to the high-level class of objects defined by the key field. For example, a certain class may be designated as a key field in both the first data table and the second data table, and the two data tables may then be merged on the basis of the class data in the key field. In these embodiments, the data corresponding to the key field in each of the merged data tables is preferably the same. However, data tables having similar, though not identical, data in the key fields may also be merged by using AGREP, for example.

Reference is made herein to "configuring" a device, or a device configured to perform some function. It should be understood that this may include selecting predefined logic blocks and logically associating them, such that they provide particular logic functions, which includes monitoring or control functions. It may also include programming computer software-based logic of retrofit control device, wiring discrete hardware components, or a combination of any or all of the foregoing.

In the descriptions herein, numerous specific details are provided, such as examples of programming, software modules, user selections, network transactions, database queries, database structures, hardware modules, hardware circuits, hardware chips, controllers, etc., to provide a thorough understanding of embodiments of the invention. One skilled in the relevant art will recognize, however, that the invention may be practiced without one or more of the specific details, or with other methods, components, materials, and so forth. In other instances, well-known structures, materials, or operations may be not shown or described in detail to avoid obscuring aspects of the invention.

Figure 34:
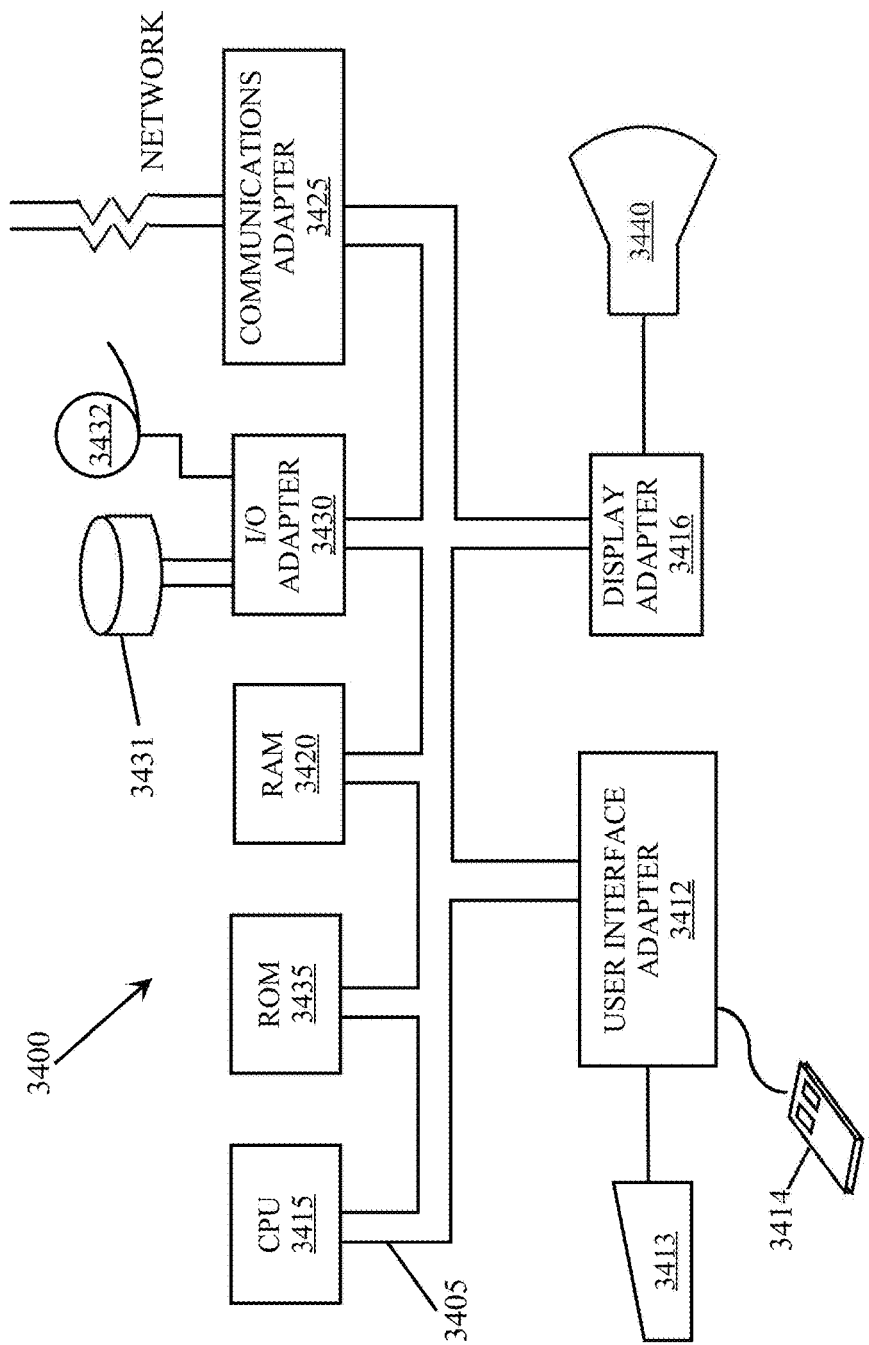
FIG. 34 illustrates a block diagram of a data processing system configured in accordance with embodiments of the present invention.

With reference now to FIG. 34, a block diagram illustrating a data processing ("computer") system 3400 is depicted in which aspects of embodiments of the invention may be implemented. The computer system 107 of FIG. 1 and/or a computer system for utilization in the sorting system 300 of FIG. 3 may be configured similarly as the computer system 3400. Computer system 3400 may employ a peripheral component interconnect ("PCI") local bus architecture. Although the depicted example employs a PCI bus, other bus architectures such as Accelerated Graphics Port ("AGP") and Industry Standard Architecture ("ISA") may be used, among others. Processor 3415, volatile memory 3420, and non-volatile memory 3435 may be connected to PCI local bus 3405 through PCI Bridge (not shown). The PCI Bridge also may include an integrated memory controller and cache memory for processor 3415. Additional connections to PCI local bus 3405 may be made through direct component interconnection or through add-in boards. In the depicted example, a communication (e.g., network (LAN)) adapter 3425, an I/O (e.g., small computer system interface ("SCSI") host bus) adapter 3430, and expansion bus interface (not shown) may be connected to PCI local bus 3405 by direct component connection. An audio adapter (not shown), a graphics adapter (not shown), and display adapter 3416 (coupled to a display 3440) may be connected to the PCI local bus 3405 (e.g., by add-in boards inserted into expansion slots).

The user interface adapter 3412 provides a connection for a keyboard 3413 and a mouse 3414, modem (not shown), and additional memory (not shown). The I/O adapter 3430 provides a connection for a hard disk drive 3431, a tape drive 3432, and CD-ROM drive (not shown).

An operating system may be run on processor 3415 and used to coordinate and provide control of various components within computer system 3400. In FIG. 34, the operating system may be a commercially available operating system. An object oriented programming system such as Java may run in conjunction with the operating system and provide calls to the operating system from Java programs or programs executing on system 3400. Instructions for the operating system, the object-oriented operating system, and programs may be located on non-volatile memory 3435 storage devices, such as a hard disk drive 3431, and may be loaded into volatile memory 3420 for execution by processor 3415.

Those of ordinary skill in the art will appreciate that the hardware in FIG. 34 may vary depending on the implementation. Other internal hardware or peripheral devices, such as flash ROM (or equivalent nonvolatile memory) or optical disk drives and the like, may be used in addition to or in place of the hardware depicted in FIG. 34. Also, the processes of the present invention may be applied to a multiprocessor computer system.

As another example, computer system 3400 may be a stand-alone system configured to be bootable without relying on some type of network communication interface, whether or not computer system 3400 includes some type of network communication interface. As a further example, computer system 3400 may be an embedded controller, which is configured with ROM and/or flash ROM providing non-volatile memory storing operating system files or user-generated data.

The depicted example in FIG. 34 and above-described examples are not meant to imply architectural limitations. Further, a computer program form of the present invention may reside on any computer readable storage medium (i.e., floppy disk, compact disk, hard disk, tape, ROM, RAM, etc.) used by a computer system. (The terms "computer," "system," "computer system," and "data processing system" may be used interchangeably herein.)

Reference throughout this specification to "an embodiment," "embodiments," or similar language means that a particular feature, structure, or characteristic described in connection with the embodiments is included in at least one embodiment of the present invention. Thus, appearances of the phrases "in one embodiment," "in an embodiment," "embodiments," "certain embodiments," "various embodiments," and similar language throughout this specification may, but do not necessarily, all refer to the same embodiment. Furthermore, the described features, structures, aspects, and/or characteristics of the invention may be combined in any suitable manner in one or more embodiments. Correspondingly, even if features may be initially claimed as acting in certain combinations, one or more features from a claimed combination can in some cases be excised from the combination, and the claimed combination can be directed to a sub-combination or variation of a sub-combination.

Benefits, advantages, and solutions to problems have been described above with regard to specific embodiments. However, the benefits, advantages, solutions to problems, and any element(s) that may cause any benefit, advantage, or solution to occur or become more pronounced may be not to be construed as critical, required, or essential features or elements of any or all the claims. Further, no component described herein is required for the practice of the invention unless expressly described as essential or critical.

Those skilled in the art having read this disclosure will recognize that changes and modifications may be made to the embodiments without departing from the scope of the present invention. It should be appreciated that the particular implementations shown and described herein may be illustrative of the invention and its best mode and may be not intended to otherwise limit the scope of the present invention in any way. Other variations may be within the scope of the following claims.

While this specification contains many specifics, these should not be construed as limitations on the scope of the invention or of what can be claimed, but rather as descriptions of features specific to particular implementations of the invention. Headings herein may be not intended to limit the invention, embodiments of the invention or other matter disclosed under the headings.

Herein, the term "or" may be intended to be inclusive, wherein "A or B" includes A or B and also includes both A and B. As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

The terminology used herein is for the purpose of describing particular embodiments only and is not intended to be limiting of the invention. As used herein, the singular forms "a," "an," and "the" may be intended to include the plural forms as well, unless the context clearly indicates otherwise.

The corresponding structures, materials, acts, and equivalents of all means or step plus function elements in the claims below may be intended to include any structure, material, or act for performing the function in combination with other claimed elements as specifically claimed.

As used herein with respect to an identified property or circumstance, "substantially" refers to a degree of deviation that is sufficiently small so as to not measurably detract from the identified property or circumstance. The exact degree of deviation allowable may in some cases depend on the specific context. As used herein, "significance" or "significant" relates to a statistical analysis of the probability that there is a non-random association between two or more entities. To determine whether or not a relationship is "significant" or has "significance," statistical manipulations of the data can be performed to calculate a probability, expressed as a "p value." Those p values that fall below a user-defined cutoff point are regarded as significant. In some embodiments, a p value less than or equal to 0.05, in some embodiments less than 0.01, in some embodiments less than 0.005, and in some embodiments less than 0.001, are regarded as significant. Accordingly, a p value greater than or equal to 0.05 is considered not significant.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a defacto equivalent of any other member of the same list solely based on their presentation in a common group without indications to the contrary.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of approximately 1 to approximately 4.5 should be interpreted to include not only the explicitly recited limits of 1 to approximately 4.5, but also to include individual numerals such as 2, 3, 4, and sub-ranges such as 1 to 3, 2 to 4, etc. The same principle applies to ranges reciting only one numerical value, such as "less than approximately 4.5," which should be interpreted to include all of the above-recited values and ranges. Further, such an interpretation should apply regardless of the breadth of the range or the characteristic being described.

Unless defined otherwise, all technical and scientific terms (such as acronyms used for chemical elements within the periodic table) used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

The invention claimed is:

1. A method for sorting a plurality of metal alloy pieces into at least a first sorted collection of metal alloy pieces having a first metal alloy composition and a second sorted collection of metal alloy pieces having a second metal alloy composition different from the first metal alloy composition, the method comprising:
determining an approximate length of each of the plurality of metal scrap pieces;
classifying a first one of the plurality of metal alloy pieces as having the first metal alloy composition as a function of the determined approximate length of the first one of the plurality of metal alloy pieces;
classifying a second one of the plurality of metal alloy pieces as having the second metal alloy composition as a function of the determined approximate length of the second one of the plurality of metal alloy pieces; and
sorting the first one of the plurality of metal alloy pieces from the second one of the metal alloy pieces in response to (1) classifying the first one of the plurality of metal alloy pieces as having the first metal alloy composition, and (2) classifying the second one of the plurality of metal alloy pieces as having the second metal alloy composition, wherein the determining the approximate length of each of the plurality of metal alloy pieces comprises measuring the approximate length of each of the plurality of metal alloys scrap pieces as they travel at a predetermined speed past a distance measuring device, wherein metal alloy compositions of the plurality of metal alloy pieces are classified as a result of acquired x-ray fluorescence ("XRF") detected from each of the plurality of metal alloy pieces using an XRF system.

2. The method as recited in claim 1, wherein the distance measuring device utilizes a light source to determine the approximate length of each of the plurality of metal alloy pieces.

3. The method as recited in claim 1, wherein the XRF system is configured to measure an XRF spectrum emitted from a particular one of each of the plurality of metal alloy pieces only for a time period determined as a function of the measured approximate length for the particular one of each of the plurality of metal alloy pieces, wherein the time period is determined as a function of the measured approximate length of the particular one of each of the plurality of metal alloy pieces and the predetermined speed so that only the XRF spectrum emitted from the particular one of each of the plurality of metal alloy pieces is measured and not from an environment surrounding the particular one of each of the plurality of metal alloy pieces, wherein the plurality of metal alloy pieces travel on a conveyor belt at the predetermined speed within a predetermined proximity to an x-ray beam emitted from the XRF system, wherein one or more x-ray detectors of the XRF system acquire the XRF spectrum comprising energy counts for a plurality of channels of x-rays fluoresced by each of the plurality of metal alloy pieces as they travel within a proximity of the x-ray beam emitted from the XRF system, wherein each of the plurality of channels represents a different element within each of the plurality of metal alloy pieces, wherein the energy counts for each of the plurality of channels are accumulated as running total energy counts for the plurality of metal alloy pieces, wherein the energy counts for each of the plurality of channels for the particular one of each of the plurality of metal alloy pieces is determined by subtracting the accumulated running total energy counts received by the x-ray detector for previously scanned metal alloy pieces from the accumulated running total energy counts received by the x-ray detector for the particular one of the plurality of metal alloy pieces on a per channel basis.

4. The method as recited in claim 3, further comprising:
normalizing a net peak area of each of the energy counts for each of the plurality of channels to generate an elemental composition signature for the first one of the plurality of metal alloy pieces; and
comparing the elemental composition signature for the first one of the plurality of metal alloy pieces on an element-by-element basis to one or more known elemental composition signatures, wherein the one or more known elemental composition signatures each correspond to a different aluminum alloy composition.

5. The method as recited in claim 4, wherein the first one of the plurality of metal alloy pieces is classified as having the first metal alloy composition when the elemental composition signature for the first one of the plurality of metal alloy pieces substantially matches with the known elemental composition signature corresponding to the first metal alloy composition.

6. The method as recited in claim 4, wherein the net peak area is determined by:
applying a smoothing filter to the XRF spectrum to produce a smooth curve plot of the XRF spectrum;
stripping away peaks of the smooth curve plot of the XRF spectrum to estimate background energy counts of the XRF spectrum; and
subtracting the estimated background energy counts from the smooth curve plot of the XRF spectrum to obtain final energy counts for each of the plurality of channels.

7. The method as recited in claim 1, wherein the XRF system comprises first and second separately energized x-ray sources linearly aligned within a single x-ray tube, wherein the first x-ray source is configured to emit x-rays towards a first singulated line of the plurality of metal alloy pieces, and wherein the second x-ray source is configured to emit x-rays towards a second singulated line of the plurality of metal alloy pieces, wherein the first and second singulated lines of metal alloy pieces travel substantially parallel to each other.

8. The method as recited in claim 4, wherein the metal alloy pieces are aluminum alloy scrap pieces.

9. The method as recited in claim 1, wherein the distance measuring device utilizes a laser light source to determine the approximate length of each of the plurality of metal alloy pieces.

10. A system for sorting metal alloys comprising:
a conveyor system configured to separate a plurality of received metal alloy pieces into first and second parallel singulated streams of the plurality of metal alloy pieces each travelling at a predetermined speed;
a distance measuring device configured to determine an approximate length for each of the plurality of metal alloy pieces within the first and second parallel singulated streams;
an XRF system configured to emit x-rays towards each of the plurality of metal alloy pieces within the first and second parallel singulated streams;
the XRF system configured to determine separate XRF spectra for each of the plurality of metal alloy pieces within the first and second parallel singulated streams only during time periods determined as a function of the approximate lengths and the relative predetermined speeds of each of the first and second parallel singulated streams;

circuitry configured to produce a plurality of spectra of net counts on a per channel basis for a plurality of channels each corresponding to a chemical element, wherein each of the plurality of spectra pertains to one of the plurality of metal alloy pieces;

circuitry configured to normalize each of the net counts to generate an elemental composition signature for each of the plurality of metal alloy pieces;

circuitry configured to compare each of the generated elemental composition signatures to one or more known elemental composition signatures, wherein the one or more known elemental composition signatures each correspond to one of a plurality of different standard reference metal alloy compositions, in order to classify each of the plurality of metal alloy pieces as corresponding to at least one of the plurality of different standard reference metal alloy compositions; and a sorting device configured to sort the plurality of metal alloy pieces into a plurality of receptacles as a function of their classified metal alloy composition.

11. The system as recited in claim 10, wherein the plurality of different standard reference metal alloy compositions fall within a same aluminum alloy series.

12. The system as recited in claim 10, wherein the XRF system comprises first and second separately energized x-ray sources linearly aligned within a single x-ray tube, wherein the first x-ray source is configured to emit x-rays towards the first parallel singulated stream of the plurality of metal alloy pieces, and wherein the second x-ray source is configured to emit x-rays towards the second parallel singulated stream of the plurality of metal alloy pieces.

13. The system as recited in claim 10, wherein first and second ones of the plurality of metal alloy pieces contain different aluminum alloys, wherein each of the plurality of different standard reference metal alloy compositions correspond to different standard reference aluminum alloy compositions, wherein the sorting device is configured so that a first one of the plurality of receptacles corresponds to a first one of the plurality of different standard reference aluminum alloy compositions, wherein the sorting device is configured so that a second one of the plurality of receptacles corresponds to a second one of the plurality of different standard reference aluminum alloy compositions, and wherein the sorting device is configured to sort the first one of the aluminum alloy pieces into the first one of the plurality of receptacles and the second one of the aluminum alloy pieces into the second one of the plurality of receptacles.

14. The system as recited in claim 10, wherein the plurality of different standard reference metal alloy compositions fall within a same Aluminum Association aluminum alloy series.

15. A system for sorting materials into separate groups, comprising:

a conveyor system configured to separate a plurality of materials into first and second parallel singulated streams of the plurality of materials each travelling at predetermined speeds;

an x-ray fluorescence ("XRF") system configured to emit x-rays towards each of the plurality of materials within the first and second parallel singulated streams, and to detect XRF from each of the plurality of materials, wherein the XRF system comprises first and second separately energized x-ray sources linearly aligned within a single x-ray tube, wherein the first x-ray source is configured to emit x-rays towards the first parallel singulated stream of the plurality of materials, and wherein the second x-ray source is configured to emit x-rays towards the second parallel singulated stream of the plurality of materials;

circuitry configured to produce a plurality of spectra of counts on a per channel basis for a plurality of channels each corresponding to a chemical element, wherein each of the plurality of spectra pertains to one of the plurality of materials;

circuitry configured to compare each of the plurality of spectra of counts to one or more known spectra of counts, wherein the one or more known spectra of counts each correspond to a different material composition, in order to classify a material composition for each of the plurality of materials; and a sorter configured to sort the plurality of materials into the separate groups as a function of their classified material composition.

16. The system as recited in claim 15, wherein the XRF system comprises:

the first and second separately energized x-ray sources linearly aligned within the single x-ray tube;

a first cathode having a first electron emitter positioned within a first grid assembly;

a second cathode having a second electron emitter positioned within a second grid assembly, wherein the first and second grid assemblies are linearly aligned with each other within the single x-ray tube, and wherein the first and second electron emitters are physically separated from each other so that they are operable to separately emit electrons towards separate portions of the anode bar;

an anode bar aligned in parallel to the first and second grid assemblies;

one or more insulator spacers configured to position the anode bar a predetermined distance from each of the first and second grid assemblies;

a first electrical feed-through configured to provide a first voltage potential to the anode bar; and a second electrical feed-through configured to provide a second voltage potential to the first and second cathodes.

17. The system as recited in claim 16, wherein the XRF system further comprises a cooling feed-through configured to permit passage of a cooling fluid from a source external to the x-ray tube through a cavity within the anode bar.

18. The system as recited in claim 15, wherein the system further comprises:

the conveyor system configured to separate the plurality of materials into the first and second parallel singulated streams of the plurality of materials, and into third and fourth parallel singulated streams of the plurality of materials, each travelling at predetermined speeds, wherein the first and second parallel singulated streams of the plurality of materials are adjacent to each other, and wherein the third and first parallel singulated streams of the plurality of materials are adjacent to each other, and wherein the second and fourth parallel singulated streams of the plurality of materials are adjacent to each other;

the XRF system configured to emit x-rays towards each of the plurality of materials within the first, second, third, and fourth parallel singulated streams, and to detect XRF from each of the plurality of materials, wherein the XRF system comprises the first and second separately energized x-ray sources linearly aligned within the single x-ray tube, and wherein the XRF system comprises third and fourth separately energized x-ray sources linearly aligned within the single x-ray tube with the first and second x-ray sources, wherein the first x-ray source is configured to emit x-rays towards the first parallel singulated stream of the plurality of materials, wherein the second x-ray source is configured to emit x-rays towards the second parallel singulated stream of the plurality of materials, wherein the third x-ray source is configured to emit x-rays towards the third parallel singulated stream of the plurality of materials, and wherein the fourth x-ray source is configured to emit x-rays towards the fourth parallel singulated stream of the plurality of materials; and the sorter configured to sort the first, second, third, and fourth parallel singulated streams of the plurality of materials into the separate groups as a function of their classified material compositions, wherein the sorter further comprises:

a first ejector device configured to eject one of the plurality of materials in the first parallel singulated stream from the conveyor system into a first bin associated with a first material composition classification;

a second ejector device configured to eject one of the plurality of materials in the second parallel singulated stream from the conveyor system into a second bin associated with a second material composition classification;

a third ejector device configured to eject one of the plurality of materials in the third parallel singulated stream from the conveyor system into a third bin associated with a third material composition classification; and a fourth ejector device configured to eject one of the plurality of materials in the fourth parallel singulated stream from the conveyor system into a fourth bin associated with a fourth material composition classification, wherein the first and second ejector devices are positioned downstream on the conveyor system relative to the third and fourth ejector devices.

19. The system as recited in claim 15, wherein the different material compositions fall within a same aluminum alloy series.

20. A method for sorting a plurality of metal alloy pieces into at least a first sorted collection of metal alloy pieces having a first metal alloy composition and a second sorted collection of metal alloy pieces having a second metal alloy composition different from the first metal alloy composition, the method comprising:

determining an approximate length of each of the plurality of metal scrap pieces;

classifying a first one of the plurality of metal alloy pieces as having the first metal alloy composition as a function of the determined approximate length of the first one of the plurality of metal alloy pieces;

classifying a second one of the plurality of metal alloy pieces as having the second metal alloy composition as a function of the determined approximate length of the second one of the plurality of metal alloy pieces; and sorting the first one of the plurality of metal alloy pieces from the second one of the metal alloy pieces in response to (1) classifying the first one of the plurality of metal alloy pieces as having the first metal alloy composition, and (2) classifying the second one of the plurality of metal alloy pieces as having the second metal alloy composition, wherein the first metal alloy composition is a first aluminum alloy composition, wherein the second metal alloy composition is a second aluminum alloy composition, and wherein the first and second aluminum alloy compositions are of different aluminum alloy compositions.

21. The method as recited in claim 20, wherein the first aluminum alloy composition and the second aluminum alloy composition fall within a same aluminum alloy series.

22. A method for sorting a plurality of metal alloy pieces into at least a first sorted collection of metal alloy pieces having a first metal alloy composition and a second sorted collection of metal alloy pieces having a second metal alloy composition different from the first metal alloy composition, the method comprising:

determining an approximate length of each of the plurality of metal scrap pieces;

classifying a first one of the plurality of metal alloy pieces as having the first metal alloy composition as a function of the determined approximate length of the first one of the plurality of metal alloy pieces and an acquired x-ray fluorescence ("XRF") detected from each of the first one of the plurality of metal alloy pieces using an XRF system;

classifying a second one of the plurality of metal alloy pieces as having the second metal alloy composition as a function of the determined approximate length of the second one of the plurality of metal alloy pieces and an acquired x-ray fluorescence detected from each of the second one of the plurality of metal alloy pieces using the XRF system; and sorting the first one of the plurality of metal alloy pieces from the second one of the metal alloy pieces in response to (1) classifying the first one of the plurality of metal alloy pieces as having the first metal alloy composition, and (2) classifying the second one of the plurality of metal alloy pieces as having the second metal alloy composition.

23. The method as recited in claim 22, wherein the first metal alloy composition is a first aluminum alloy composition, wherein the second metal alloy composition is a second aluminum alloy composition, and wherein the first and second aluminum alloy compositions are of different aluminum alloy compositions.

24. The method as recited in claim 23, wherein the first aluminum alloy composition and the second aluminum alloy composition fall within a same aluminum alloy series.

* * * * *